US012780828B2

(12) United States Patent
Zhang et al.

(10) Patent No.: US 12,780,828 B2
(45) Date of Patent: Nov. 3, 2026

(54) METHODS AND MODIFIED NUCLEOSIDES FOR TREATING CORONAVIRUS INFECTIONS

(71) Applicants: SOUTHERN UNIVERSITY OF SCIENCE AND TECHNOLOGY, Shenzhen (CN); SUN YAT-SEN UNIVERSITY, Guangzhou (CN)

(72) Inventors: Xumu Zhang, Shenzhen (CN); Deyin Guo, Shenzhen (CN); Guanguan Li, Shenzhen (CN); Liu Cao, Shenzhen (CN); Yingjun Li, Shenzhen (CN); Tiefeng Xu, Shenzhen (CN); Yanxi Ji, Shenzhen (CN); Qifan Zhou, Shenzhen (CN); Yujian Yang, Shenzhen (CN); Tiaozhen Zhu, Shenzhen (CN)

(73) Assignee: SOUTHERN UNIVERSITY OF SCIENCE AND TECHNOLOGY, Shenzhen (CN)

( * ) Notice: Subject to any disclaimer, the term of this patent is extended or adjusted under 35 U.S.C. 154(b) by 627 days.

(21) Appl. No.: 18/270,009

(22) PCT Filed: Sep. 15, 2021

(86) PCT No.: PCT/CN2021/118372
§ 371 (c)(1),
(2) Date: Jun. 28, 2023

(87) PCT Pub. No.: WO2022/142477
PCT Pub. Date: Jul. 7, 2022

(65) Prior Publication Data

US 2024/0317754 A1 Sep. 26, 2024

(30) Foreign Application Priority Data

Dec. 30, 2020 (CN) ......................... 202011613943.3
May 21, 2021 (CN) ......................... 202110562244.9

(51) Int. Cl.
*C07D 487/04* (2006.01)
*A61K 31/706* (2006.01)
*A61P 31/14* (2006.01)

(52) U.S. Cl.
CPC .......... *C07D 487/04* (2013.01); *A61K 31/706* (2013.01); *A61P 31/14* (2018.01)

(58) Field of Classification Search
None
See application file for complete search history.

(56) References Cited

U.S. PATENT DOCUMENTS 7,973,013 B2 7/2011 Cho et al.
8,318,682 B2 11/2012 Butler et al.
9,457,039 B2 10/2016 Girijavallabhan et al.
10,251,904 B2 4/2019 Clarke et al.
10,682,368 B2 6/2020 Perron et al.
10,695,357 B2 6/2020 Chun et al.
10,696,679 B2 6/2020 Mackman et al.
2017/0037078 A1 2/2017 Coats et al.
2017/0334941 A1 11/2017 Coats et al.
2020/0277321 A1 9/2020 Beigelman et al.

FOREIGN PATENT DOCUMENTS

CN 110330540 A 10/2019
CN 111135184 A 5/2020
CN 111961057 A 11/2020
CN 112778310 A 5/2021
CN 113185519 A 7/2021
CN 113354684 A 9/2021
WO WO-2017049060 A1 * 3/2017 .............. A61P 31/12
WO WO-2019053696 A1 * 3/2019 ............. C07H 19/23
WO 2021257569 12/2021

OTHER PUBLICATIONS

International Search Report of PCT/CN2021/118372 dated Dec. 22, 2021.
Written Opinion of PCT/CN2021/118372 dated Dec. 22, 2021.
English Translation of CN 112778310.
English Translation of CN 113185519.
English Translation of CN 113354684.
English Translation of CN 111961057.
English Translation of CN 111135184.
English Translation of CN 110330540.
Wei, D., et al., "Potency and pharmacokinetics of GS-441524 derivatives against SARS-CoV-2," Bioorganic & Medicinal Chemistry, Aug. 11, 2021, vol. 46, pp. 1-12.
Li, J. , et al. , "Tissue-Specific Protcomics Analysis of Anti-COVID-19 Nucleoside and Nucleotide Prodrug-Activating Enzymes Provides Insights into the Optimization of Prodrug Design and Pharmacotherapy Strategy," Pharmacol. Transl. Sci., Apr. 1, 2021, vol. 4, pp. 870-887.

(Continued)

*Primary Examiner* — Patrick T Lewis
(74) *Attorney, Agent, or Firm* — OPENPTO US LLC; Yuhao Liang

(57) ABSTRACT

Provided are methods for treating coronavirus infections by administering modified nucleosides, ester and amino acid ester prodrugs of nucleoside, their pharmaceutically acceptable salts, and drug combination thereof, of Formula (I). The compounds, combination, and methods provided are particularly useful for preventing, mitigating, or treating coronavirus infections or cytopathic effects resulting from the replication or reproduction of coronaviruses and their variants, including SARS-CoV-2.

(I)

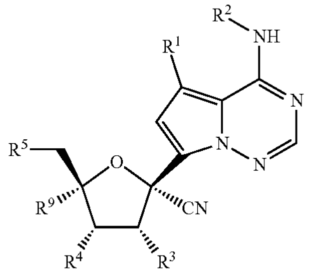

15 Claims, 4 Drawing Sheets

(56) References Cited

OTHER PUBLICATIONS

Misr, M. R., et al., "Preparation and biological evaluation of 1'-cyano-2'-methyl pvrimidinc nucleosides as HCV NS5B polymerase inhibitors," Bioorganic & Medicinal Chemistry Letters, May 22, 2014, Vol. 24, pp. 3092-3095.
Siegel, D., et al., "Discovery and Synthesis of a Phosphoramidate Prodrug of a Pyrrolo[2, 1-f ][triazin-4-amino] Adenine C-Nucleoside (GS-5734) for the Treatment of Ebola and Emerging Viruses," J. Med. Chem., Jan. 26, 2017, vol. 60, pp. 1648-1661.
Cho, A., et al., "Discovery of the First C-Nucleoside HCV Polymerase Inhibitor (GS-6620) with Demonstrated Antiviral Response in HCV Infected," J. Med. Chem., Apr. 2, 2013, vol. 57, pp. 1812-1825.
Cho, A. et al., "Synthesis and antiviral activity of a series of 1'-substituted 4-aza-7, 9-dideazaadenosine C-nucleosides," Bioorganic & Medicinal Chemistry Letters, Mar. 8, 2012, vol. 22, pp. 2705-2707.
European Communication pursuant to Article 94(3) EPC of the corresponding European Application issued on Feb. 20, 2026.

* cited by examiner

METHODS AND MODIFIED NUCLEOSIDES FOR TREATING CORONAVIRUS INFECTIONS

CROSS REFERENCE TO RELATED APPLICATIONS

This is a U.S. national stage application of the International Patent Application No. PCT/CN2021/118372, filed Sep. 15, 2021, which claims the benefit of priority from Chinese Application No. 202011613943.3, filed Dec. 30, 2020, and Chinese Application No. 202110562244.9, filed May 21, 2021; all of which are incorporated by reference herein in their entirety.

FIELD OF THE INVENTION

The invention generally relates to methods and compounds for treating coronavirus infections, particularly methods and nucleosides for treating SARS-CoV-2 infections or infections caused by SARS-CoV-2 variants.

BACKGROUND OF THE INVENTION

Severe acute respiratory syndrome coronavirus 2 (SARS-CoV-2, previously called 2019-nCoV) is an enveloped, positive-sense, single-stranded RNA virus. It belongs to the genus β coronavirus. Similar to SARS-associated coronavirus (SARS-CoV) and the Middle East Respiratory Syndrome Coronavirus (MERS-CoV), the SARS-CoV-2 genome encodes non-structural proteins including 3-chymotrypsin-like protease (3CLPro), papain-like protease (PL-Pro), helicase, methyltransferases, and RNA-dependent RNA polymerase (RdRp), as well as structural proteins such as spike glycoproteins and accessory proteins. The spike protein of SARS-CoV-2 binds angiotensin-converting enzyme 2 (ACE2) on host respiratory epithelial cells to initiate entry and then release the viral RNA into the cytoplasm. The open reading frame at the 5'-terminal 2/3 region of viral RNA (ORF1A/B) encodes polyproteins (PP1a and PP1ab), which play an essential role in the process of viral replication. PP1a and PP1ab can be cleaved by PLPro and 3CLPro to produce non-structural proteins, including RdRp and helicase for viral transcription and replication. At present, these four proteins, including S-protein, 3CLPro, PLPro, and RdRp, that are involved in viral entry, reproduction, and transcription process, respectively, are the most attractive targets for the development of antiviral drugs.

The Delta variant of SARS-CoV-2, also known as B.1.617.2, is classified as a "variant of concern" by World Health Organization (WHO). Scientists believe that the Delta variant is more transmissible and probably increases SARS-CoV-2 pathogenicity. The viral load of the Delta variant is 1260 times higher than the original SARS-CoV-2, which may cause more severe disease. Though more than 2.76 billion vaccine doses have been administered worldwide, it remains a concern about the vaccine efficacy against the SARS-CoV-2 variant, especially the Delta variant.

The UK is the first country to grant emergency use of the COVID-19 vaccine developed by Pfizer and BioNTech on Dec. 2, 2020. With the rapid spread of the mutated Delta variant is the major source of uncertainty of the vaccine effectiveness. In addition, the storage of COVID-19 vaccine usually requires very low temperature, such as a range of −80° C. to −60° C. for the Pfizer and BioNTech vaccine, which brings great inconvenience to its wide use.

Remdesivir is currently the only drug approved by the U.S. Food and Drug Administration (FDA) for COVID-19. Remdesivir is an adenosine analog prodrug originally developed by Gilead as an anti-Ebola drug. As an inhibitor of RdRp, remdesivir exhibited anti-SARS-CoV-2 activity at the cell level; however, the data from clinical trials showed that remdesivir did not significantly reduce mortality in humans. As the dose used in clinical trials was close to the safe dose, some side effects were reported with concerns in patients receiving remdesivir.

According to the applicant's previous study on remdesivir and its metabolite GS-441524 (Li, et al., J. Med. Chem. 2020), it was found that GS-441524 produced a better antiviral effect than remdesivir in mice. GS-441524 exhibited a better safety profile, although it has a similar mechanism of action, as compared to remdesivir. Accordingly, the applicant has applied for a patent (application number or patent number 202011000517.2) describing the drug application of GS-441524 in the prevention, mitigation and/or treatment for SARS-CoV-2 infections.

The pharmacokinetic profile of GS-441524 demonstrated a low bioavailability, and it could only be administrated by iv injection. Therefore, it would be essential to develop less toxic nucleoside derivatives or prodrugs of GS-441524 that can be taken orally to control the SARS-CoV-2 pandemic.

SUMMARY OF THE INVENTION

In one aspect, the invention provides nucleoside derivatives of the Formula (I), or a pharmaceutically acceptable salt thereof:

(I)

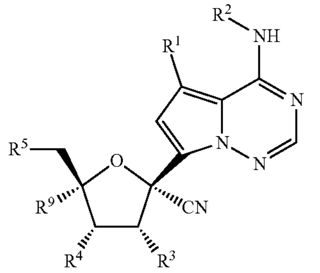

$R^1$ is H, D, F, or Cl;

$R^2$, $R^3$, $R^4$, $R^5$ are independently selected from H, D, halogen, $R^6$, $R^7$, OH, —$OR^6$, —$OR^7$, —$NH_2$, —$NHR^6$, —$NHR^7$, —$NR^7R^8$, SH, —$SR^7$, —$SSR^7$, $SeR^7$, L-amino acid ester, or D-amino acid ester;

$R^6$ is selected from —C(═O)$R^7$, —C(═O)O$R^7$, —C(═O)NH$R^7$, —C(═O)N$R^7R^8$, —$CH_2$OC(═O)O$R^7$, —$CH_2$OC(═O)NH$R^7$, —$CH_2$OC(═O)N$R^7R^8$, —C(═O)S$R^7$, —C(═S)$R^7$, —S(═O)$R^7$ or —S(═O)$_2R^7$;

$R^7$ and $R^8$ are independently selected from a substituted or non-substituted $C_1$-$C_{10}$ alkyl, a substituted or non-substituted $C_3$-$C_{10}$ cycloalkyl, a substituted or non-substituted $C_3$-$C_{10}$ cycloalkenyl, a substituted or non-substituted $C_3$-$C_{10}$ cycloalkynyl, a substituted or non-substituted $C_2$-$C_{10}$ enyl, a substituted or non-substituted $C_2$-$C_{10}$ alkynyl, a substituted or non-substituted $C_6$-$C_{20}$ aryl, a substituted or non-substituted $C_3$-$C_{20}$ heterocyclyl, a substituted or non-substituted $C_6$-$C_{20}$ aralkyl, or a deuterium substitute of any of them;

$R^9$ is H or F.

Another aspect of the invention provides a pharmaceutical composition comprising the compound of Formula (I), or a nucleoside derivative, a prodrug, or a pharmaceutically acceptable salt thereof to a subject in need thereof.

In another aspect, the invention provides a method of preventing, mitigating or treating coronavirus infections or cytopathic effects resulting from the replication or reproduction of coronavirus variants comprising administrating an effective amount of the compound of Formula (I), or a nucleoside derivative, a prodrug, or a pharmaceutically acceptable salt thereof, or a pharmaceutical composition comprising the compound of Formula (I) to a subject in need thereof.

DETAILED DESCRIPTION OF EXEMPLARY EMBODIMENTS

Compounds

Figure 1:
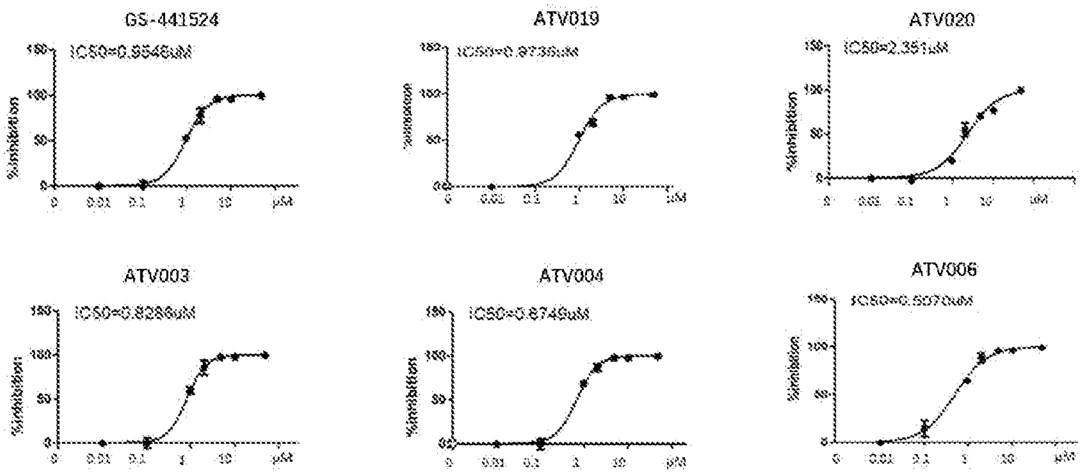
FIG. 1 shows the dose-dependent anti-SARS-CoV-2 effect of compounds GS-441524, ATV003, ATV004, ATV006, ATV019, and ATV020 on the HEK293T cell-based replicon system.

In a first aspect are provided compounds of Formula (I) or a pharmaceutically acceptable salt thereof. Embodiments of Formula (I) include the following descriptions of $R^1$, $R^2$, $R^3$, $R^4$, $R^5$, $R^6$, $R^7$, $R^8$, and $R^9$, and any combinations thereof.

An embodiment herein comprises a compound of Formula (I) or a pharmaceutically acceptable salt thereof, (I)

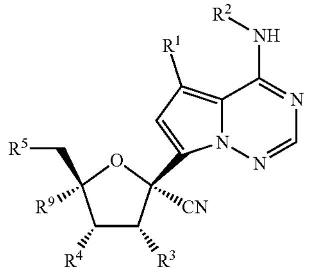

wherein:

$R^1$ is H, D, F, or $C_1$;

$R^2$, $R^3$, $R^4$, $R^5$ are independently selected from H, D, halogen, $R^6$, $R^7$, OH, $—OR^6$, $—OR^7$, $—NH_2$, $—NHR^6$, $—NHR^7$, $—NR^7R^8$, SH, $—SR^7$, $—SSR^7$, $SeR^7$, L-amino acid ester, or D-amino acid ester;

$R^6$ is selected from $—C(═O)R^7$, $—C(═O)OR^7$, $—C(═O)NHR^7$, $—C(═O)NR^7R^8$, $—CH_2OC(═O)OR^7$, $—CH_2OC(═O)NHR^7$, $—CH_2OC(═O)NR^7R^8$, $—C(═O)SR^7$, $—C(═S)R^7$, $—S(═O)R^7$ or $—S(═O)_2R^7$;

$R^7$ and $R^8$ are independently selected from a substituted or non-substituted $C_1$-$C_{10}$ alkyl, a substituted or non-substituted $C_3$-$C_{10}$ cycloalkyl, a substituted or non-substituted $C_3$-$C_{10}$ cycloalkenyl, a substituted or non-substituted $C_3$-$C_{10}$ cycloalkynyl, a substituted or non-substituted $C_2$-$C_{10}$ enyl, a substituted or non-substituted $C_2$-$C_{10}$ alkynyl, a substituted or non-substituted $C_6$-$C_{20}$ aryl, a substituted or non-substituted $C_3$-$C_{20}$ heterocyclyl, a substituted or non-substituted $C_6$-$C_{20}$ aralkyl, or a deuterium substitute of any of them;

$R^9$ is H or F.

A further embodiment comprises a compound of Formula (I), or a pharmaceutically acceptable salt thereof, as described above, wherein the substituted or non-substituted $C_1$-$C_{10}$ alkyl is selected from the group consisting of a substituted or non-substituted $C_1$-$C_5$ alkyl, a substituted or non-substituted $C_2$-$C_4$ alkyl, a substituted or non-substituted $C_2$-$C_3$ alkyl.

Also provided is an embodiment comprising a compound of Formula (I) or a pharmaceutically acceptable salt thereof, as described above, wherein the substituted or non-substituted $C_3$-$C_{10}$ cycloalkyl is selected from the group consisting of a substituted or non-substituted $C_3$-$C_6$ cycloalkyl, a substituted or non-substituted $C_4$-$C_{10}$ cycloalkyl, a substituted or non-substituted $C_4$-$C_8$ cycloalkyl, a substituted or non-substituted $C_4$-$C_6$ cycloalkyl, a substituted or non-substituted $C_5$-$C_6$ cycloalkyl.

Also provided is an embodiment comprising a compound of Formula (I) or a pharmaceutically acceptable salt thereof, as described above, wherein the substituted or non-substituted $C_3$-$C_{10}$ cycloalkenyl is selected from the group consisting of a substituted or non-substituted $C_3$-$C_{10}$ cycloalkenyl, a substituted or non-substituted $C_4$-$C_{10}$ cycloalkenyl, a substituted or non-substituted $C_4$-$C_8$ cycloalkenyl, a substituted or non-substituted $C_4$-$C_6$ cycloalkenyl, a substituted or non-substituted $C_5$-$C_6$ cycloalkenyl.

Also provided is an embodiment comprising a compound of Formula (I) or a pharmaceutically acceptable salt thereof, as described above, wherein the substituted or non-substituted $C_3$-$C_{10}$ cycloalkynyl is selected from the group consisting of a substituted or non-substituted $C_3$-$C_{10}$ cycloalkynyl, a substituted or non-substituted $C_4$-$C_{10}$ cycloalkynyl, a substituted or non-substituted $C_4$-$C_8$ cycloalkynyl, a substituted or non-substituted $C_4$-$C_6$ cycloalkynyl, a substituted or non-substituted $C_5$-$C_6$ cycloalkynyl.

Also provided is an embodiment comprising a compound of Formula (I) or a pharmaceutically acceptable salt thereof, as described above, wherein the substituted or non-substituted $C_6$-$C_{20}$ aryl is selected from the group consisting of a substituted or non-substituted $C_6$-$C_{12}$ aryl, a substituted or non-substituted $C_6$-$C_{10}$ aryl.

Also provided is an embodiment comprising a compound of Formula (I) or a pharmaceutically acceptable salt thereof, as described above, wherein the substituted or non-substituted $C_3$-$C_{20}$ heterocyclyl is selected from the group consisting of a substituted or non-substituted $C_4$-$C_{10}$ heterocyclyl, a substituted or non-substituted $C_4$-$C_6$ heterocyclyl, a substituted or non-substituted $C_4$-$C_8$ heterocyclyl.

Also provided is an embodiment comprising a compound of Formula (I) or a pharmaceutically acceptable salt thereof, as described above, wherein the heteroatoms of the substituted or non-substituted $C_3$-$C_{20}$ heterocyclyl are nitrogen or oxygen atom.

Also provided is an embodiment comprising a compound of Formula (I) or a pharmaceutically acceptable salt thereof, as described above, wherein the number of the heteroatom in the substituted or non-substituted $C_3$-$C_{20}$ heterocyclyl is 1 or 2.

Also provided is an embodiment comprising a compound of Formula (I) or a pharmaceutically acceptable salt thereof, as described above, wherein the substituted group is selected from the group consisting of methyl, ethyl, phenyl, indole, pyrrole, amino, halogen, sulfhydryl, and thiol-methyl substitution.

Also provided is an embodiment comprising a compound of Formula (I) or a pharmaceutically acceptable salt thereof, as described above, wherein $R^2$ is H, OH, or —$R^6$.

Also provided is an embodiment comprising a compound of Formula (I) or a pharmaceutically acceptable salt thereof, as described above, wherein $R^2$ is H.

Also provided is an embodiment comprising a compound of Formula (I) or a pharmaceutically acceptable salt thereof, as described above, wherein $R^2$ is OH.

Also provided is an embodiment comprising a compound of Formula (I) or a pharmaceutically acceptable salt thereof, as described above, wherein $R^2$ is —$R^6$.

Also provided is an embodiment comprising a compound of Formula (I) or a pharmaceutically acceptable salt thereof, as described above, wherein $R^9$ is H or F.

Also provided is an embodiment comprising a compound of Formula (I) or a pharmaceutically acceptable salt thereof, as described above, wherein $R^9$ is H.

Also provided is an embodiment comprising a compound of Formula (I) or a pharmaceutically acceptable salt thereof, as described above, wherein $R^9$ is F.

Also provided is an embodiment comprising a compound of Formula (I) or a pharmaceutically acceptable salt thereof, as described above, wherein $R^3$ and $R^4$ is OH.

Also provided is an embodiment comprising a compound of Formula (I) or a pharmaceutically acceptable salt thereof, as described above, wherein $R^1$ is H, F, or D.

Also provided is an embodiment comprising a compound of Formula (I) or a pharmaceutically acceptable salt thereof, as described above, wherein $R^1$ is H.

Also provided is an embodiment comprising a compound of Formula (I) or a pharmaceutically acceptable salt thereof, as described above, wherein $R^1$ is F.

Also provided is an embodiment comprising a compound of Formula (I) or a pharmaceutically acceptable salt thereof, as described above, wherein $R^1$ is D.

Also provided is an embodiment comprising a compound of Formula (I) or a pharmaceutically acceptable salt thereof, as described above, wherein $R^5$ is selected from —$OR^6$, L-amino acid ester, or D-amino acid ester.

Also provided is an embodiment comprising a compound of Formula (I) or a pharmaceutically acceptable salt thereof, as described above, wherein $R^5$ is selected from —$OR^6$.

Also provided is an embodiment comprising a compound of Formula (I) or a pharmaceutically acceptable salt thereof, as described above, wherein $R^5$ is selected from L-amino acid ester, or D-amino acid ester;

Also provided is an embodiment comprising a compound of Formula (I) or a pharmaceutically acceptable salt thereof, as described above, wherein $R^5$ is selected from the amino acid esters synthesized from the presented nucleosides and L or D-amino acid, including histidine (His), isoleucine (Ile), leucine (Leu), lysine (Lys), methionine (Met), phenylalanine (Phe), threonine (Thr), tryptophan (Trp), valine (Val), Arginine (Arg), cysteine (Cys), glutamine (Gln), glycine (Gly), proline (Pro), serine (Ser), tyrosine (Tyr), alanine (Ala), asparagine (Asn), aspartic acid (Asp), glutamic acid (Glu), and selenocysteine (Sec).

Also provided is an embodiment comprising a compound of Formula (I) or a pharmaceutically acceptable salt thereof, as described above, wherein $R^1$ is H, D or F; $R^2$ is H, OH or —$R^6$; $R^3$ and $R^4$ are OH; $R^5$ is —$OR^6$, L-amino acid ester, or D-amino acid ester; $R^6$ is —C(═O)$R^7$; $R^9$ is H or F.

Also provided is an embodiment comprising a compound of Formula (I) or a pharmaceutically acceptable salt thereof, as described above, wherein the compound of Formula (I) is selected from the compound of Formula (II):

(II)

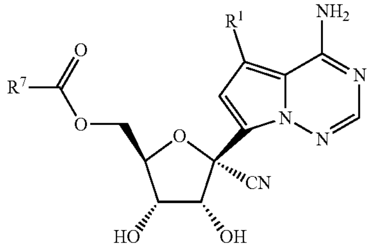

Also provided is an embodiment comprising a compound of Formula (I) or a pharmaceutically acceptable salt thereof, as described above, wherein $R^7$ is selected from the group consisting phenyl, 2-propyl, methyl, ethyl, —CH2CF3, 1-propyl, 1-butyl, 2-methyl-1-propyl, 2-butyl, 2-methyl-2-propyl, 1-amyl, 3-amyl, 2-methyl-2-butyl, 3-methyl-2-butyl, 3-methyl-1-butyl, 2-methyl-1-butyl, 1-hexyl, 2-hexyl, 3-hexyl, 2-methyl-2-amyl, 3-methyl-2-amyl, 4-methyl-2-amyl, 3-methyl-3-amyl, 2-methyl-3-amyl, 2, 3-dimethyl-2-butyl, 3, 3-dimethyl-2-butyl, 3, 3-dimethyl-2-butyl, octyl, naphthalene, tetrahydro-2H-pyranyl and 1-methylpiperidyl; preferably, the $R^7$ is selected from cyclopropyl, cyclobutyl, cyclopentyl, cyclohexyl, cycloheptyl and cyclooctyl.

Also provided is an embodiment comprising a compound of Formula (I) or a pharmaceutically acceptable salt thereof, as described above, wherein $R^7$ is selected from cyclopropyl, cyclobutyl, cyclopentyl, cyclohexyl, cycloheptyl, or cyclooctyl.

Some of the embodiments described above comprising a compound of Formula (I), or a pharmaceutically acceptable salt thereof, suitable compounds include the following:

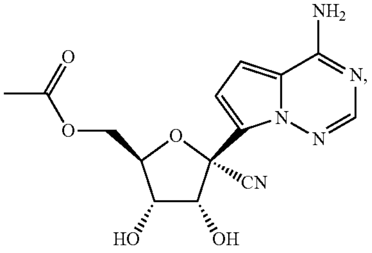

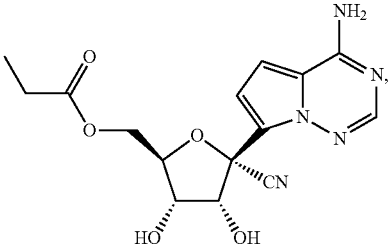

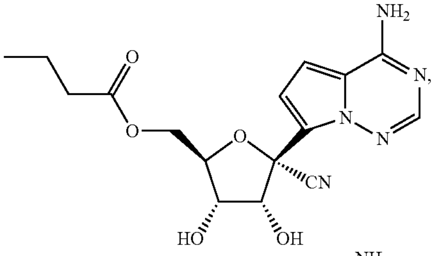

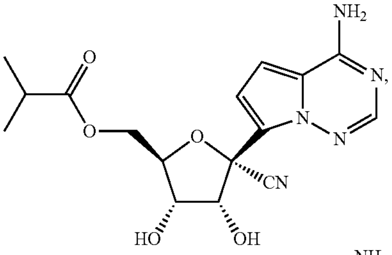

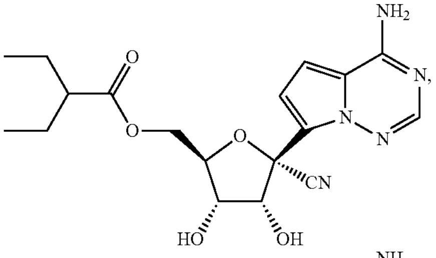

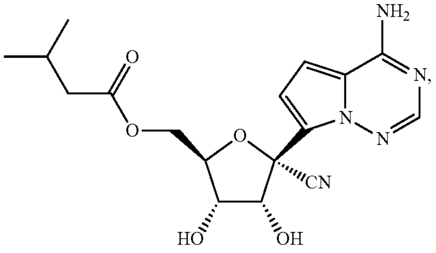

-continued

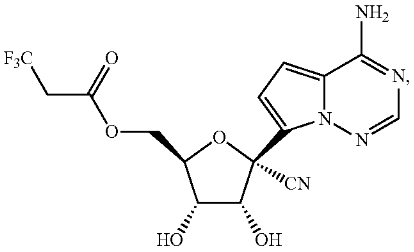

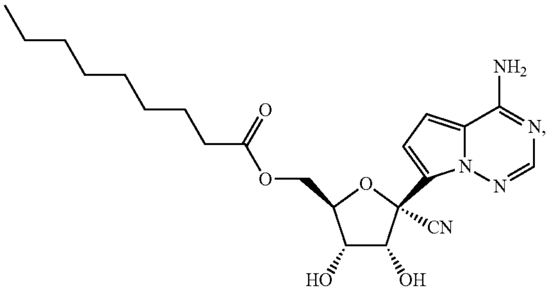

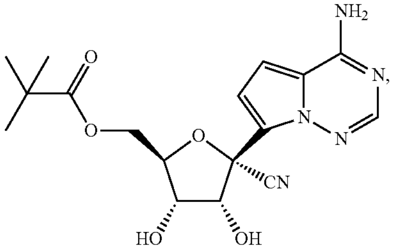

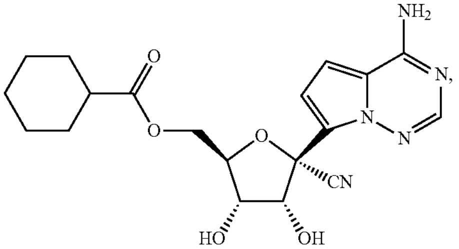

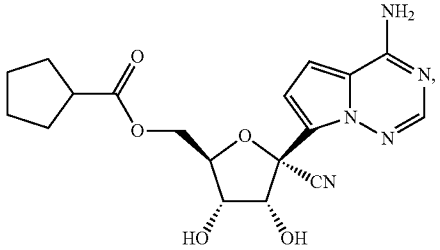

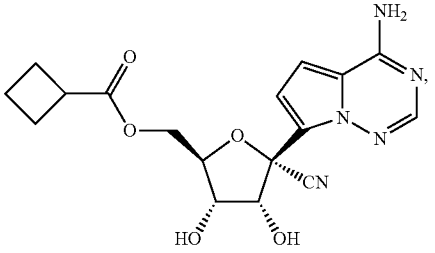

-continued
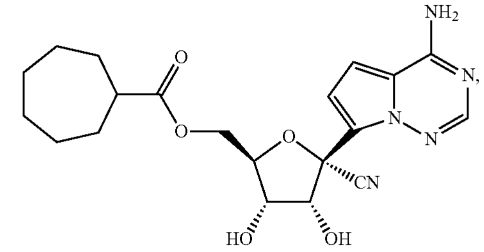
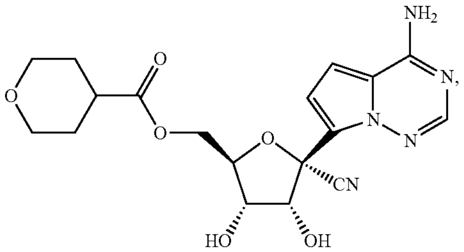
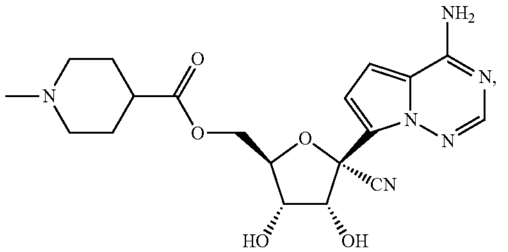
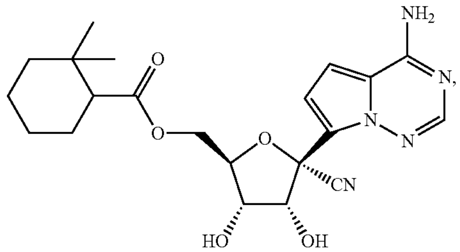
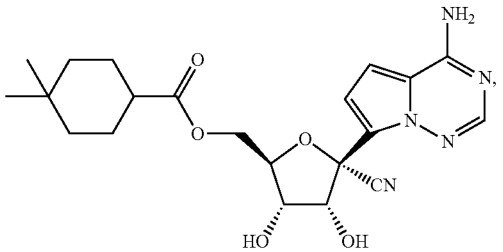
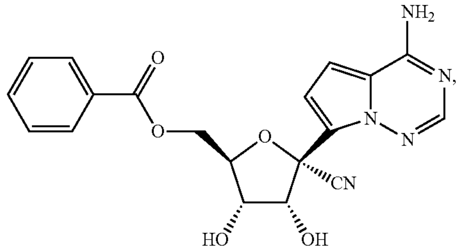
-continued
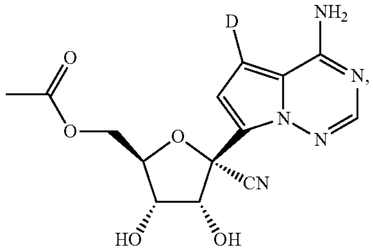
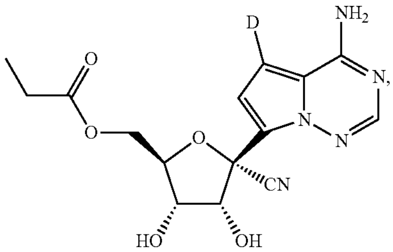
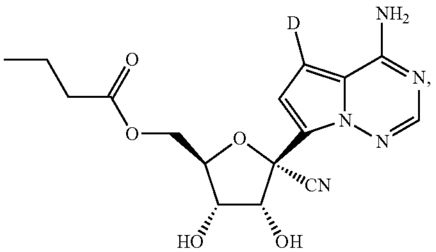
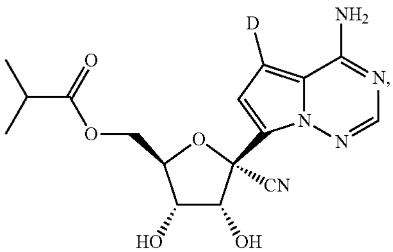
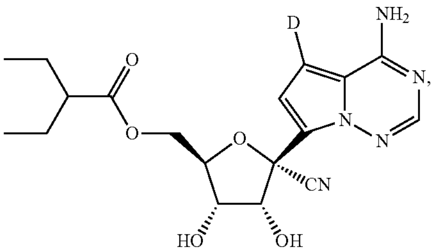
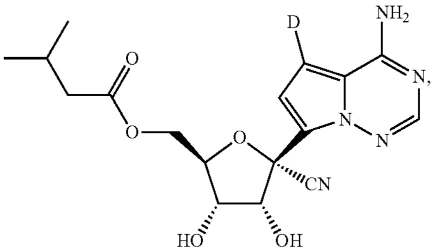

-continued
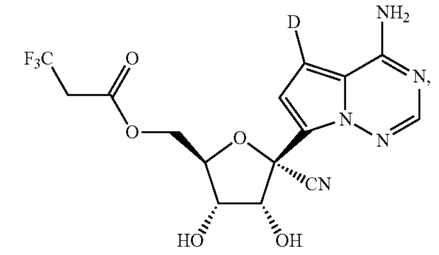
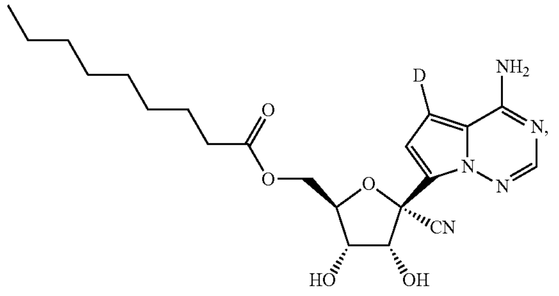
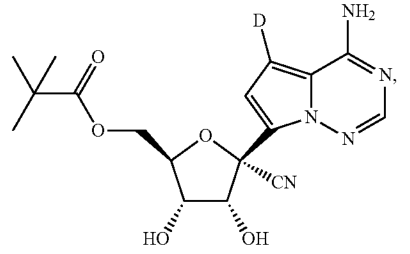
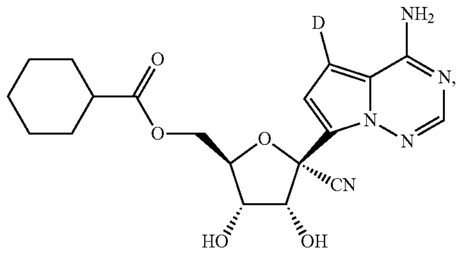
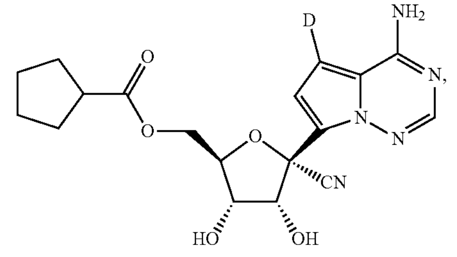
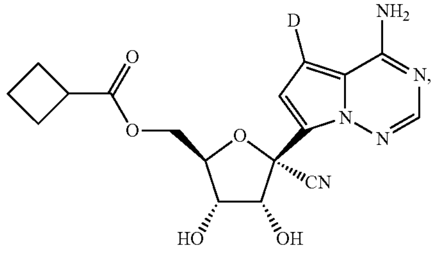
-continued
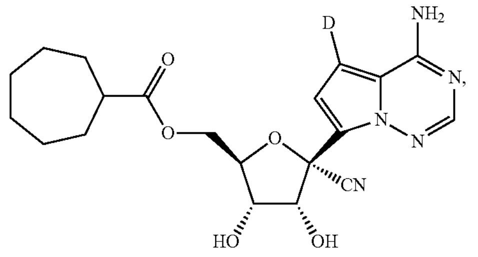
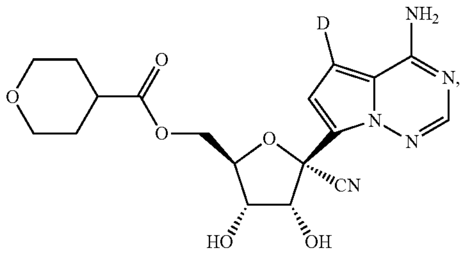
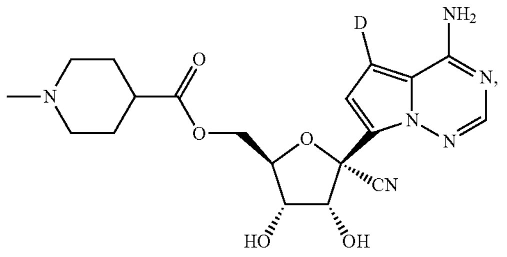
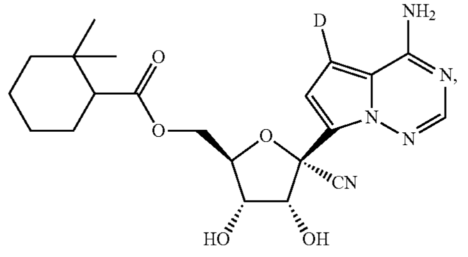
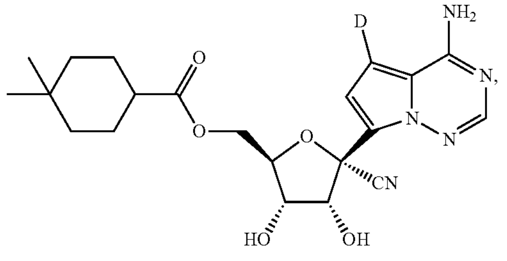
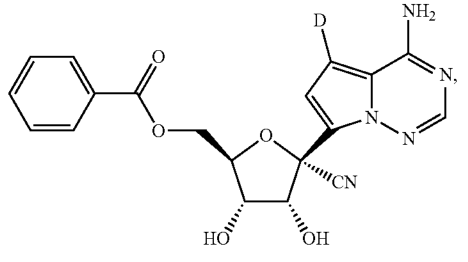

-continued
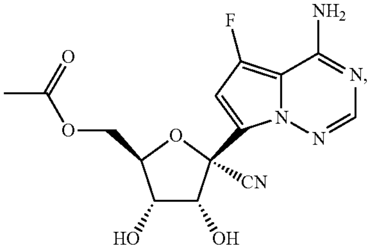
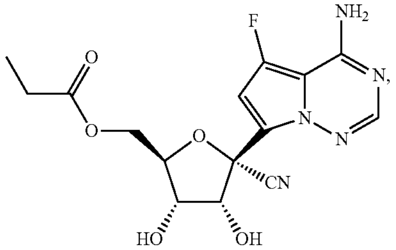
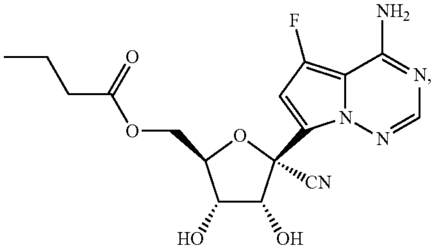
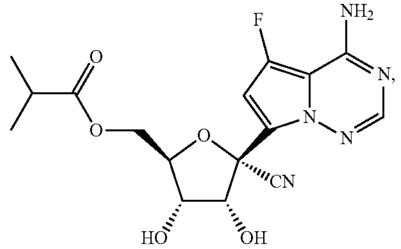
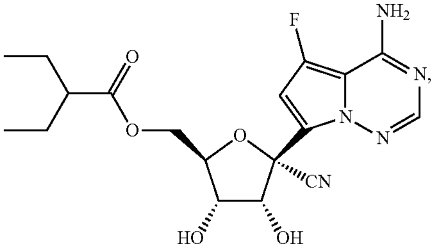
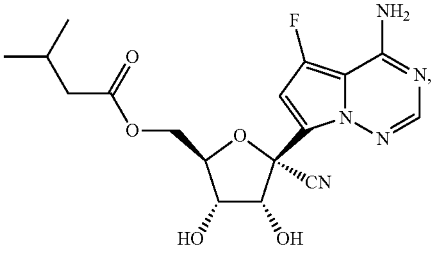
-continued
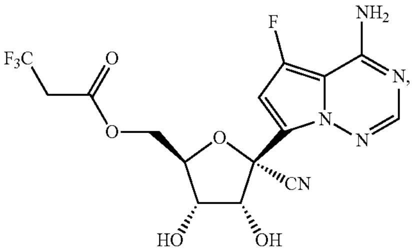
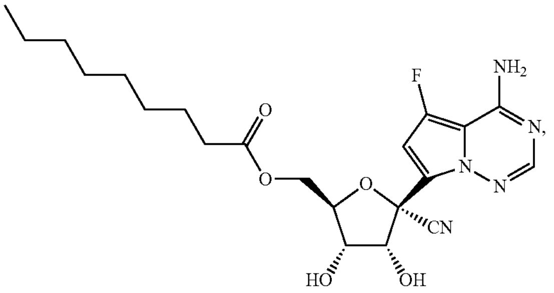
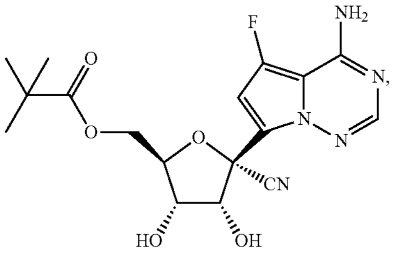
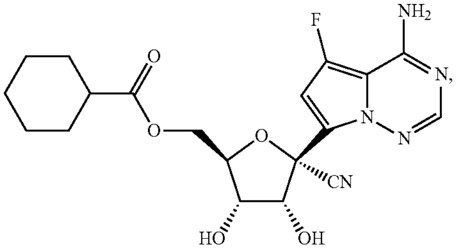
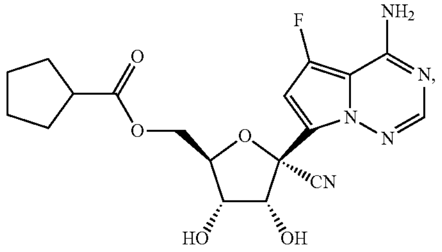
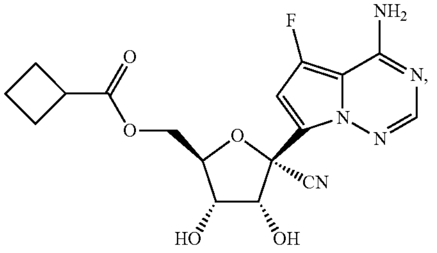

-continued
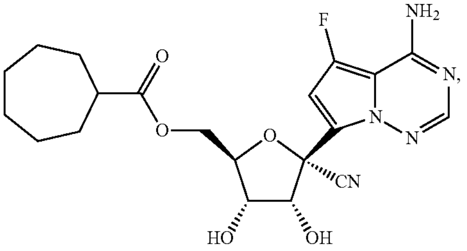
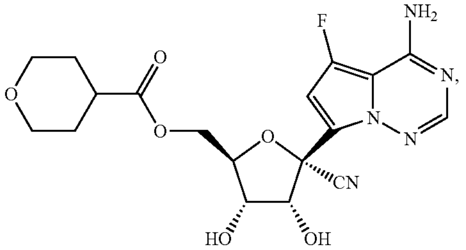
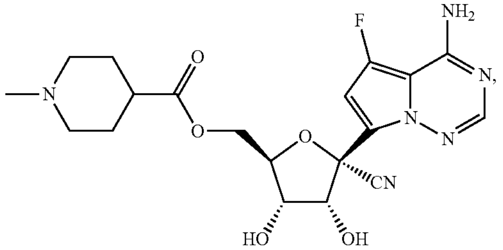
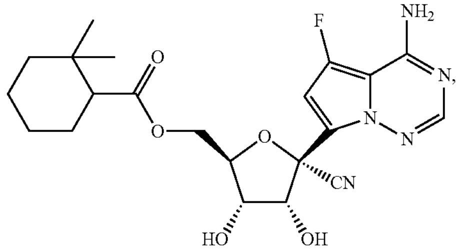
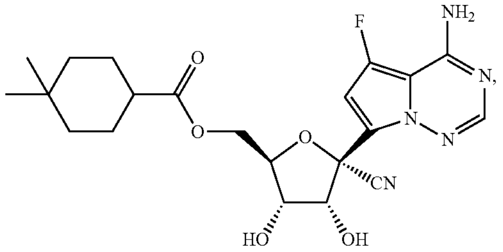
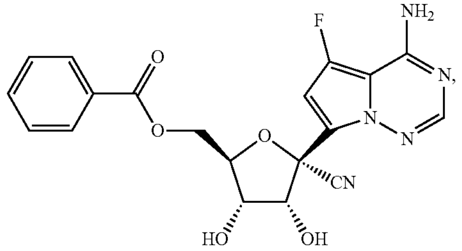
-continued
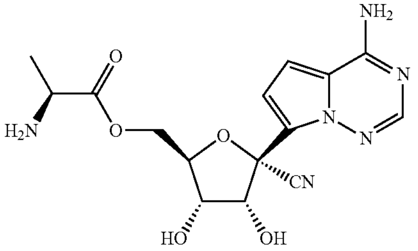
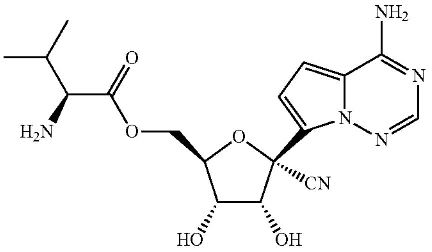
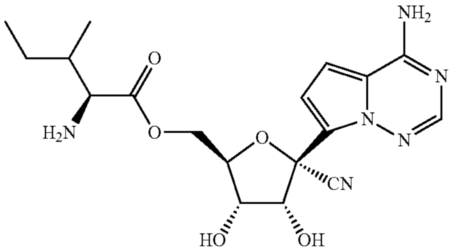
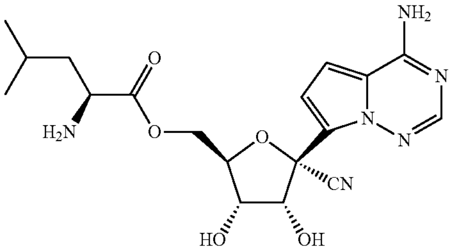
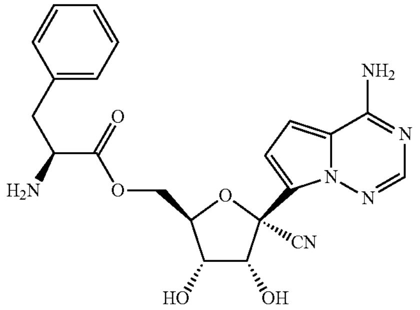
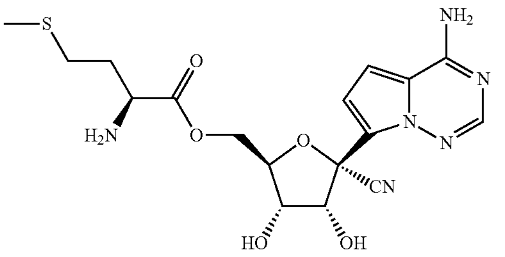

-continued
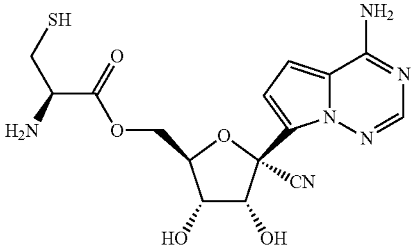
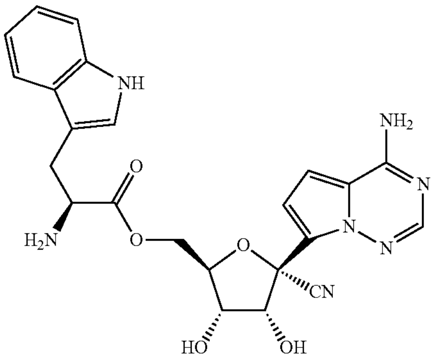
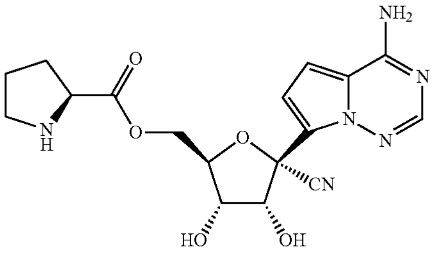
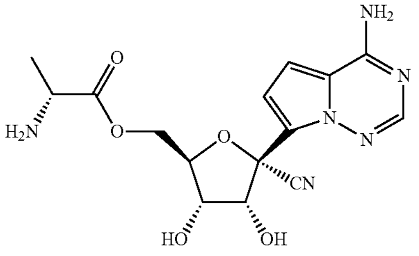
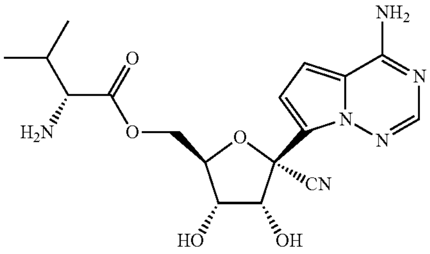
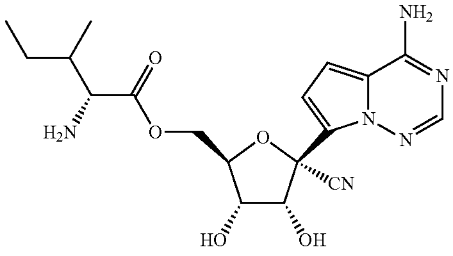
-continued
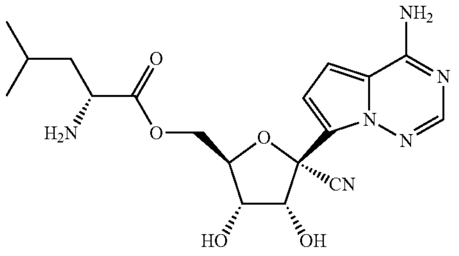
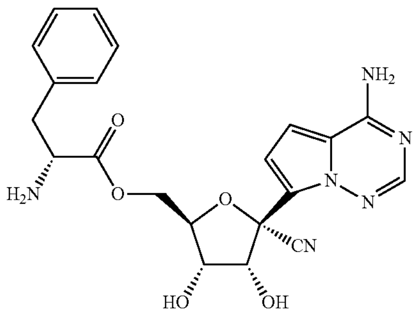
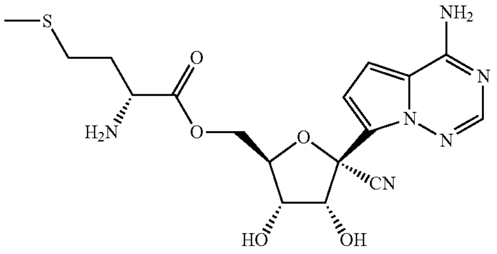
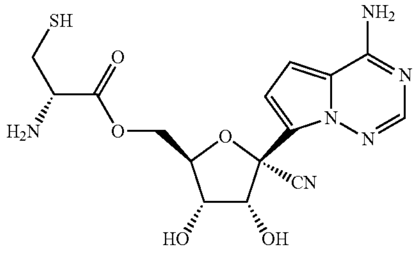
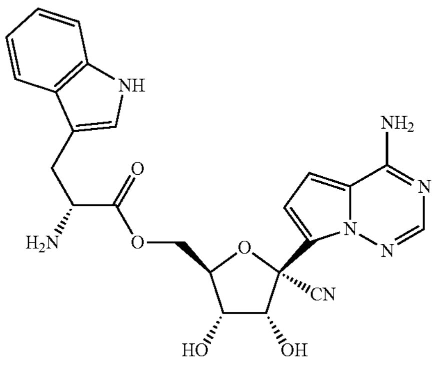
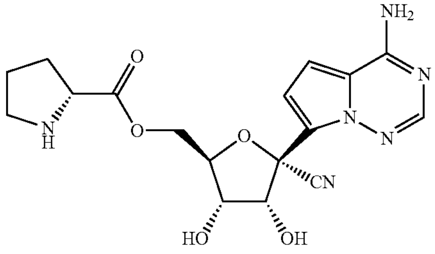

Some of the more preferred embodiments described above comprising a compound of Formula (I), or a pharmaceutically acceptable salt thereof, suitable compounds are selected from the following:

ATV006

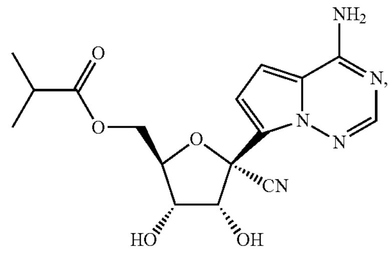

ATV013

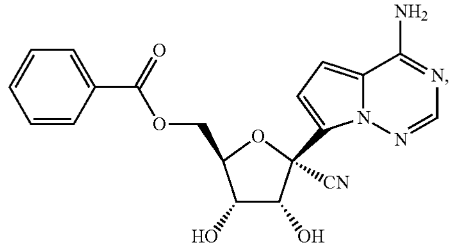

ATV014

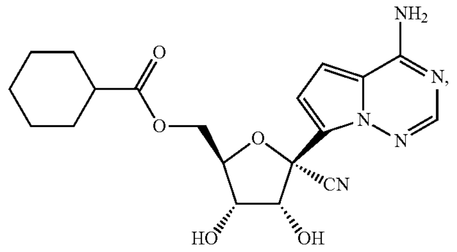

ATV015

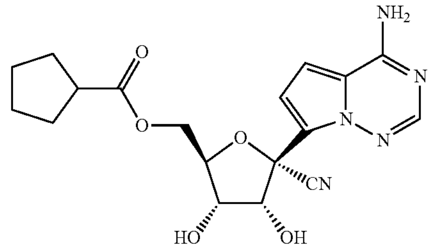

Some of the embodiments described above comprising a compound of Formula (I), or a pharmaceutically acceptable salt thereof, the compound below is not included:

GS-441524

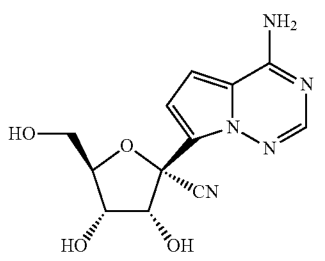

Also provided is an embodiment comprising a compound of Formula (I) or a pharmaceutically acceptable salt thereof, as described above, or a pharmaceutically acceptable form thereof, wherein the pharmaceutically acceptable form of the compound includes racemates, enantiomers, tautomers, polymorphs, pseudo polymorphs, amorphous forms, hydrates, and solvates.

In another aspect are provided pharmaceutical compositions compromising administrating an effective amount of a nucleoside derivative, prodrugs of Formula (I), or a pharmaceutically acceptable salt thereof to a subject in need thereof.

The pharmaceutical compositions, according to the present invention, include a pharmaceutically acceptable carrier or excipient.

The dosage formulation of pharmaceutical compositions according to the present invention include a pill, a tablet, a cream, an emulsion, a gel, a suspension, a lyophilized agent, a powder, a capsule, a sustained-release agent, a granule, an aerosol, a liquid, and a combination of any thereof.

The pharmaceutical compositions, according to the present invention, include traditional Chinese medicine and/or western medicine.

Western medicine in the pharmaceutical compositions according to the present invention includes at least one of apilimod, R 82913 (CAS: 126347-69-1), DS-6930 (CAS: 1242328-82-0), ONO 5334 (CAS: 1242328-82-0), oseltamivir phosphate, Hanfangchin A, clofazimine, astemizole, recombinant human angiotensin-converting enzyme 2, or favipiravir and/or their pharmaceutically acceptable salts.

In another aspect, the invention provides applications of the described compounds or pharmaceutical compositions.

The invention provides a method of preparing products for preventing, mitigating, or treating coronavirus infections or cytopathic effects resulting from the replication or reproduction of coronavirus variants comprising administering an effective amount of any compound, a pharmaceutically acceptable salt thereof, or the pharmaceutical composition described above to a subject in need thereof.

The invention provides a method of preventing, mitigating, or treating coronavirus infections or cytopathic effects resulting from the replication or reproduction of coronavirus variants comprising administering an effective amount of any compound, a pharmaceutically acceptable salt thereof, or the pharmaceutical composition described above to a subject in need thereof.

In another embodiment, the infections according to the present invention include fever, cough, sore throat, pneumonia, acute respiratory infection, severe acute respiratory infection, hypoxic respiratory failure, acute respiratory distress syndrome, sepsis, or septic shock.

The invention provides a method of preparing products for detecting the coronavirus and its homologous variants comprising administering an effective amount of any compound, a pharmaceutically acceptable salt thereof, or the pharmaceutical composition described above to a subject in need thereof.

The invention provides a method of detecting the coronavirus and its homologous variants comprising administering an effective amount of any compound, a pharmaceutically acceptable salt thereof, or the pharmaceutical composition described above to a subject in need thereof.

In another embodiment, the coronavirus according to the present invention includes MHV-A59, HCoV-229E, HCoV-OC43, HCoV-NL63, HCoV—HKU1, SARS-CoV, MERS-CoV, SARS-CoV-2, murine hepatitis virus, feline infectious peritonitis virus, canine coronavirus, bovine coronavirus, avian infectious bronchitis virus, or porcine coronavirus.

In another embodiment, the SARS-CoV-2, according to the present invention, includes SARS-CoV-2 and its variants.

In another embodiment, the SARS-CoV-2 variants according to the present invention include the Alpha (B.1.1.7), Beta (B.1.351, B.1.351.2, B.1.351.3), Delta (B.1.617.2, AY.1, AY.2, AY.3), and Gamma (P.1, P.1.1, P.1.2), Eta (B.1.525), Theta (P.3), Kappa (B.1.617.1), Lambda (C.37) variants and all of the above sub-lineages.

The compound or its pharmaceutically acceptable salt thereof, according to the present invention, is provided to human or non-human animals.

In another embodiment, the non-human animal subject, according to the present invention, includes bovine, equine, sheep, pig, canine, cat, rodent, primate, bird, or fish.

BENEFICIAL EFFECTS

The invention has the following technical effects as compared to the prior art:

The compounds or their pharmaceutically acceptable salts thereof, according to the present invention, exhibited good antiviral activity against SARS-CoV-2 (B.1) and MHV-A59. These compounds effectively inhibited the viral replication and/or reproduction on HEK293 cells and Vero E6 cells, especially for the SARS-CoV-2 variants including delta (B.1.617.2) and Beta (B.1.351) with low toxicity.

Compounds ATV006 and ATV014 both have significant inhibitory effects for SARS-CoV-2 replicon on HEK293T cells, with lower $IC_{50}$ values and higher antiviral activity, as compared to GS-441524 and intermediate 5 of remdesivir. The antiviral activity against SARS-CoV-2 variants of ATV006 and ATV014 is 3-4 times greater than GS-441524, and the $IC_{50}$ value of ATV014 was lower than 0.34 μM, indicating both compounds exhibited inhibitory effects against SARS-CoV-2 variants in cell level and in animal models.

Moreover, ATV006 and ATV014 both have excellent pharmacokinetic properties, significantly improved bioavailability, and druggable potential. The bioavailability of ATV006 in Sprague-Dawley rats and cynomolgus monkeys was 79% and 30%, respectively. The bioavailability of ATV014 in Sprague-Dawley rats was 49%.

The compounds or their pharmaceutically acceptable salts thereof, according to the present invention, have simple structures, easy synthetic routes, and are conducive to production and distribution.

The preparation method of the compounds or their pharmaceutically acceptable salts thereof according to the present invention are easy operation and is conducive to industrial production.

In addition, compound ATV014 showed promising antiviral activity against SARS-CoV-s and its variants, and its anti-SARS-CoV-2 activity was twice that of GS-441524, which indicated that ATV006 could effectively inhibit the replication and/or reproduction of the virus in cells. ATV006 was able to protect mice from MHV-A59 infection and increased the survival rate at low dosage (2 mg/kg); it exhibited an excellent antiviral effect in a dose-dependent manner at a medium dose (5 mg/kg-50 mg/kg).

Definitions

The term "coronavirus" refers to various RNA-containing spherical viruses of the family coronaviridae, including but not limited to SARS-CoV-2, MERS-CoV, and SARS-CoV. Coronaviruses can be spread between animals and people. The term "corona," which is from a Latin root meaning crown or ring of light, refers to the shape of the virus under a microscope.

The term "SARS-CoV-2" refers to the newly-emerged coronavirus, which was identified as the cause of a severe outbreak in 2019. SARS-CoV-2 has also been known as 2019-nCoV. It binds via the viral spike protein to the human host cell receptor angiotensin-converting enzyme 2 (ACE2). The spike protein also binds to and is cleaved by TMPRSS2, which activates the spike protein for membrane fusion of the virus.

The term "COVID-19" refers to a specific illness related to the current epidemic. COVID-19 is an acronym provided by the World Health Organization and stands for "coronavirus disease 2019," referring to the year the virus was first detected. The name of the virus is SARS-CoV-2.

The term "SARS-CoV-2 variant," as used herein, is synonymous with 'mutant' and refers to a nucleic acid or amino acid sequence which differs in comparison to the corresponding wild-type sequence of SARS-CoV-2. SARS-CoV-2 variants include, but are not limited to, the "Variants of Concern (VOC)," "Variants of interest (VOI)," and the variant under monitoring as the WHO proposed labels for global SARS-CoV-2 variants to be used alongside the scientific nomenclature in communications about variants to the public on May 31, 2021. This list includes variants on WHO's global list of VOC and VOI, and is updated as WHO's list changes. The SARS-CoV-2 variants include, but are not limited to, VOC and VOI, such as Alpha (B.1.1.7), Beta (B.1.351, B.1.351.2, B.1.351.3), Delta (B.1.617.2, AY.1, AY.2, AY.3), and Gamma (P.1, P.1.1, P.1.2), Eta (B.1.525), Theta (P.3), Kappa (B.1.617.1), Lambda (C.37) and the variants under monitoring.

The term "B.1" refers to a SARS-CoV-2 strain (B.1, hCoV-19/CHN/SYSU-IHV/2020 strain, Accession ID on GISAID: EPI_ISL_444969) was isolated from a sputum sample from a woman admitted to the Eighth People's Hospital of Guangzhou.

The term "coronavirus infection" or "CoV infection," as used herein, refers to infection with a coronavirus such as SARS-CoV-2, MERS-CoV, or SARS-CoV. The term includes coronavirus respiratory tract infections, often in the lower respiratory tract. Symptoms can include high fever, dry cough, shortness of breath, pneumonia, gastrointestinal symptoms such as diarrhea, organ failure (kidney failure and renal dysfunction), septic shock, and death in severe cases.

The term "a compound of Formula (I)" refers to the compound of Formula (I) or a pharmaceutically acceptable salt thereof, or a pharmaceutically acceptable form thereof, and the pharmaceutically acceptable form of the compound includes racemates, enantiomers, tautomers, polymorphs, pseudo polymorphs, amorphous forms, hydrates, and solvates.

The term "V/V" refers to the volume ratio.

The term "$IC_{50}$" refers to the half-maximal inhibitory concentration.

The term "room temperature" refers to the ambient temperature, ranging from approximately 10° C.-40° C. In some embodiments, "room temperature" refers to a temperature ranging from about 20° C. to about 30° C.; in other embodiments, "room temperature" refers to a temperature ranging from approximately 25° C. to approximately 30° C.; in some embodiments, "room temperature" refers to 10° C., 15° C., 20° C., 25° C., 30° C., 35° C., 40° C., etc.

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modem Methods of Organic Synthesis, 3rd Edition, Cambridge University Press, Cambridge, 1987; the entire contents of each of which are incorporated herein by reference.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl. Some non-limiting examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$, 1-heptyl, 1-octyl, and the like.

The term "cycloalkyl" as used herein refers to nonaromatic, saturated or partially unsaturated cyclic, bicyclic, tricyclic, or polycyclic hydrocarbon groups having 3 to 12 carbons (e.g., 3, 4, 5, 6, or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl, and norbornenyl.

The terms "alkyl" and the prefix "alk-" are inclusive of both straight-chain and branched saturated carbon chain.

The term "alkenyl" refers to a straight or branched hydrocarbon chain having one or more double bonds, the carbon-carbon $sp^2$ double bond. Examples of alkenyl groups include, but are not limited to, allyl, propenyl, 2-butenyl, 3-hexenyl, and 3-octenyl groups. One of the double bond carbons may optionally be the point of attachment of the alkenyl substituent. An alkenyl group may be optionally substituted. Unless otherwise specified, alkylene groups contain 2-12 carbon atoms. In some embodiments, alkylene groups contain 2-10 carbon atoms. In other embodiments, alkylene groups contain 2-6 carbon atoms. Some non-limiting examples of alkyl groups include, but are not limited to ethylene or vinyl ($-CH{=}CH_2$), allyl ($-CH_2CH{=}CH_2$), cyclopentenyl ($-C_5H_7$), and 5-hexenyl ($-CH_2CH_2CH_2CH_2CH_2CH{=}CH_2$).

The term "cycloalkenyl," as used herein, refers to a monovalent or divalent group of 3 to 8 carbon atoms derived from a saturated cycloalkyl having at least one double bond. Cycloalkenyl groups can be monocyclic or polycyclic. One methylene (—CH2-) group of the cycloalkenyl can be replaced, by a divalent C3-6 cycloalkyl, by a divalent heterocycle, or by a divalent aryl group. Cycloalkenyl groups can be independently substituted by halogen, nitro groups, cyano groups, —OC1-6 alkyl groups, —SC1-6 alkyl groups, —C1-6 alkyl groups, —C2-6 alkenyl groups, —C2-6 alkynyl groups, ketone groups, aldehyde groups, amino groups, C3-8 cycloalkyl groups or hydroxyl groups.

The term "alkynyl" refers to a straight or branched monovalent hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted. Preferably, the alkynyl group contains 2 to 10 carbon atoms, 2 to 8 carbon atoms, and more preferably 2 to 6 carbon atoms. Examples include, but are not limited to, ethynyl (—C≡CH), propargyl ($-CH_2C{\equiv}CH$), propynyl (—C≡C—CH3), and the like.

The term "cycloalkynyl," as used herein, refers to a monovalent carbocyclic group having one or two carbon-carbon triple bonds and having from eight to twelve carbons, unless otherwise specified. Cycloalkynyl may include one transannular bond or bridge. Non-limiting examples of cycloalkynyl include cyclooctynyl, cyclononynyl, cyclodecynyl, and cyclodecadiynyl. The cycloalkynyl group may be unsubstituted or substituted (e.g., optionally substituted cycloalkynyl) as defined for cycloalkyl.

The term "aryl" refers to an aromatic monocyclic, bicyclic, or tricyclic hydrocarbon ring system, wherein any ring atom capable of substitution can be substituted (e.g., with one or more substituents). Preferably, the aryl group contains 6 to 20 carbon atoms, 6 to 14 carbon atoms, and more preferably 6 to 10 carbon atoms. Examples of aryl moieties include, but are not limited to, phenyl, naphthyl, and anthracenyl. The aryl radicals are optionally substituted independently with one or more substituents described herein.

The term "arylalkyl" refers to an alkyl moiety in which an alkyl hydrogen atom is replaced with an aryl group. Arylalkyl includes groups in which more than one hydrogen atom has been replaced with an aryl group. Preferably, the arylalkyl group contains 7 to 20 carbon atoms, alkyl moiety contains 1 to 6 carbon atoms, and aryl moiety contains 6 to 14 carbon atoms. Examples of arylalkyl groups include, but are not limited to, benzyl, 2-phenyl ethyl-1-, naphthyl methyl, 2-naphthyl ethyl-1-, naphthyl benzyl, 2-naphthyl phenyl ethyl-1-, and analogs. Aryl alkyl groups may contain from 7 to 20 carbon atoms, for example, the alkyl part is 1 to 6 carbon atoms, and the aryl part is 6 to 14 carbon atoms.

The "heterocycle" or "heterocyclyl" used in this article include, as examples, but are not limited to those described in the following: Paquette, Leo A.: Principles of Modern Heterocyclic Chemistry (W. A. Benjamin, New York, 1968), especially Chapter1, 3, 4, 6, 7, and 9: The Chemistry of Heterocyclic Compounds, A Series of Monographs^ (John Wiley & Sons, New York, 1950-present), in particular, volumes 13, 14, 16, 19 and 28 and J. Am. Chem. Soc. (1960) 82,5566. In some embodiments of the present invention, a "heterocyclyl" includes a "carbon ring" as defined herein, in which one or more (e.g., 1, 2, 3, or 4) carbon atoms have been replaced by heterocyclic atoms (e.g., O, N or S). The term "heterocycle" or "heterocyclyl" includes saturated, partially a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclic groups can contain fused rings, which are rings that share one or more common atoms. Substituted heterocyclic groups include, for example, heterocyclic groups that are substituted by any substituent, including a carbonyl group disclosed here. Examples of heterocycles include, but are not limited to, pyridine, piperidine, thiazole, tetrahydrothiophene, sulfur oxide tetrahydrothiophene, pyrimidine, furan, thiophene, pyrrole, pyrazole, imidazole, tetrazole, coumarone, sulfur, naphthalene, indole, indole ene, quinoline, isoquinoline, benzene, imidazole, piperidine, 4-piperidine ketone, pyrrolidine, 2-pyrrolidone, pyrroline, tetrahydrofuran, quinoline, decahydroquinoline, octahydroisoquinoline, acridine (azacyclo-octane), triazine, 6H-1, 2, 5-thiadiazinyl, 2H, 6H-1, 5,2-2 thiazine base, thiophene, thiamethoxam anthracene, pyran, coumarone, xanthene, flavin-phenol, thiazole, pyrazine, pyridazine, indole, indazole, purine, phthalein, nalidixic, quinazoline, pteridine, carbazole, acridine, pyrimidine, phenazine, phenothiazine, cefuroxime, oxazine, imidazole, imidazoline, pyrazole, pyrazole, piperazine, quinine, morpholine, benzotriazole, benzene, hydroxy indole, benzene, and oxazoline.

The term "heterocyclyl" or "heterocyclic" as used herein refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclic groups can contain fused rings, which are rings that share one or more common atoms. Examples of the heterocyclic group include, but are not limited to, oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl, indolinyl, 1,2,3,4-tetrahydroisoquinolinyl, 1,3-benzodioxolyl, 2-oxa-5-azabicyclo[2.2.1]hept-5-yl. Some non-limited examples of heterocyclyl wherein —CH2- group replaced by —C(O)— moiety is 2-oxopyrrolidinyl, oxo-1,3-thiazolidinyl, 2-piperidinonyl, 3,5-dixoxpiperidinyl and pyrimidinedionyl. Some non-limited examples of heterocyclyl wherein the ring sulfur atom is oxidized is sulfolanyl, 1,1-dioxo-thiomorpholinyl. The heterocyclic group is optionally substituted with one or more substituents described herein.

In one embodiment, heterocyclyl can be 4-7 membered heterocyclyl, which refers to a saturated or partially unsaturated monocyclic ring containing 4-7 ring atoms, of which at least one ring atom is selected from nitrogen, sulfur, and oxygen, and of which may, unless otherwise specified, be carbon or nitrogen linked, and of which a —CH2- group can optionally be replaced by a —C(═O)— group. Ring sulfur atoms may be optionally oxidized to form S-oxides. Ring nitrogen atoms maybe optionally oxidized to form N-oxides. Examples of 4-7 membered heterocyclyl include, but are not limited to, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl, homopiperazinyl, homopiperidinyl, oxepanyl, thiepanyl, oxazepinyl, diazepinyl, thiazepinyl. Some non-limited examples of heterocyclyl wherein —CH2- group is replaced by —C(═O)— moiety are 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized is sulfolanyl, 1,1-dioxo-thiomorpholinyl. The 4-7 membered heterocyclyl is optionally substituted with one or more substituents described herein.

In another embodiment, heterocyclyl groups may be 4-membered heterocyclyl, which refers to a saturated or partially unsaturated monocyclic ring containing 4 ring atoms, of which at least one ring atom is selected from nitrogen, sulfur, and oxygen, and which may, unless otherwise specified, be carbon or nitrogen linked, and of which a —CH2- group can optionally be replaced by a —C(═O)— group. Ring sulfur atoms may be optionally oxidized to form S-oxides. Ring nitrogen atoms can be optionally oxidized to form N-oxides. Examples of 4-membered heterocyclyl include, but are not limited to, azetidinyl, oxetanyl, thietanyl. The 4-membered heterocyclyl is optionally substituted with one or more substituents described herein.

In another embodiment, heterocyclyl may be a 5-membered heterocyclyl, which refers to a saturated or partially unsaturated monocyclic ring containing five ring atoms, of which at least one ring atom is selected from nitrogen, sulfur, and oxygen, and of which may, unless otherwise specified, be carbon or nitrogen linked, and of which a —CH2- group can optionally be replaced by a —C(═O)— group. Ring sulfur atoms may be optionally oxidized to form S-oxides. Ring nitrogen atoms can be optionally oxidized to form N-oxides. Examples of 5-membered heterocyclyl include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl. Some non-limited examples of heterocyclyl wherein —CH2- group is replaced by —C(═O)— moiety are 2-oxopyrrolidinyl, oxo-1,3-thiazolidinyl. A non-limited example of heterocyclyl wherein the ring sulfur atom is oxidized is sulfolanyl. The 5-membered heterocyclyl is optionally substituted with one or more substituents described herein.

In still another embodiment, heterocyclyl may be a 6-membered heterocyclyl, which refers to a saturated or partially unsaturated monocyclic ring containing 6 ring atoms, of which at least one ring atom is selected from nitrogen, sulfur and oxygen, and of which may, unless otherwise specified, be carbon or nitrogen linked, and of which a —CH2- group can optionally be replaced by a —C(═O)— group. Ring sulfur atoms may be optionally oxidized to form S-oxides. Ring nitrogen atoms can be optionally oxidized to form N-oxides. Examples of 6 membered heterocyclyl include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, thioxanyl, dithianyl. Some non-limited examples of heterocyclyl wherein —CH2- group is replaced by —C(═O)— moiety are 2-piperidinonyl, 3,5-dixoxpiperidinyl and pyrimidinedionyl. A non-limited example of heterocyclyl wherein the ring sulfur atom is oxidized 1,1-dioxo-thiomorpholinyl. The 6-membered heterocyclyl is optionally substituted with one or more substituents described herein.

In yet another embodiment, heterocyclyl refers to a 7-12 membered heterocyclyl, which refers to a saturated or partially unsaturated spiro or fused bicyclic ring containing 7-12 ring atoms, of which at least one ring atom is selected from nitrogen, sulfur and oxygen, and of which may, unless otherwise specified, be carbon or nitrogen linked, and of which a —CH2- group can optionally be replaced by a —C(═O)— group. Ring sulfur atoms may be optionally oxidized to form S-oxides. Ring nitrogen atoms can be optionally oxidized to form N-oxides. Examples of 7-12 membered heterocyclyl include, but are not limited to, indolinyl, 1,2,3,4-tetrahydroisoquinolinyl, 1,3-benzodioxolyl, 2-oxa-5-azabicyclo[2.2.1]hept-5-yl. The 7-12 membered heterocyclyl is optionally substituted with one or more substituents described herein.

The terms "fused bicyclic ring," "fused cyclic," "fused bicyclic," and "fused cycles" are used interchangeably to refer to a monovalent or multivalent saturated or partially unsaturated fused ring system, which refers to a bicyclic ring system that is not aromatic. Such a system may contain isolated or conjugated unsaturation, but not aromatic or heteroaromatic rings in its core structure (but may have aromatic substitution thereon).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P, and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines, benzofuran, benzothiophene, and purines.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C═O), phosphonate, sulfinyl, sulfonyl, sulfonate, sulfonamino, sulfonamido, thioamido, thiol, thioxo (e.g., C═S), and ureido. In embodiments, substituents on a group are independently any one single or any combination of the aforementioned substituents. In embodiments, a substituent may itself be substituted with any one of the above substituents.

The terms "halo" or "halogen" refer to halogen atoms selected from F, $C_1$, Br, I, At, and Ts.

The term "haloalkyl" as used herein refers to an alkyl in which one or more hydrogen atoms are replaced with a halogen and includes alkyl moieties in which all hydrogens have been substituted with halogens (e.g., perfluoroalkyl such as $CF_3$).

The term "azido" or "$N_3$" refers to an azide moiety. This radical may be attached, for example, to a methyl group to form azidomethane (methyl azide, $MeN_3$); or attached to a phenyl group to form phenyl azide ($PhN_3$).

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "n membered," where n is an integer, typically describes the number of ring-forming atoms in a moiety where the number of ring-forming atoms is n. For example, piperidinyl is an example of a six membered heterocycloalkyl, and 1,2,3,4-tetrahydro-naphthalene is an example of a ten membered cycloalkyl group.

The term "unsaturated" refers to a moiety having one or more units of unsaturation.

The term "heteroatom" refers to one or more of oxygen, sulfur, nitrogen, phosphorus, or silicon, including any oxidized form of nitrogen, sulfur, or phosphorus; the quaternized form of any basic nitrogen; or substitutable nitrogen of a heterocyclic ring, for example, N (as in 3,4-dihydro-2H-pyrrolyl), NH (as in pyrrolidinyl) or NR (as in N-substituted pyrrolidinyl).

The term "hydroxy" refers to an —OH radical. The term "alkoxy" refers to an —O-alkyl radical. The term "aryloxy" refers to an —O-aryl radical. The term "haloalkoxy" refers to an —O-haloalkyl radical.

The above substituents may be abbreviated herein; for example, the abbreviations Me, Et, and Ph represent methyl, ethyl, and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with a permitted valence of the atoms and the substituents, such that the selections and substitutions result in a stable compound, e.g., which does not spontaneously undergo transformation such as by rearrangement, cyclization, elimination, etc.

In the context of treating a disorder, the term "effective amount" as used herein refers to an amount of the compound or a composition comprising the compound which is effective, upon single or multiple dose administrations to a subject, in treating a cell or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

The compound, according to Formula (I) or its pharmacologically acceptable salt, may exist as different polymorphs or pseudo polymorphs.

As used herein, "polymorph" refers to crystalline forms having the same chemical composition but different spatial arrangements of the molecules, atoms, and/or ions forming the crystal.

The term "pseudopolymorph" refers to a hydrate of a compound. In other words, it is a crystal form that incorporates a stoichiometric amount of water.

The term "polymorphic" or "polymorphism" is defined as the possibility of at least two different crystalline arrangements for the same chemical molecule.

The compound, according to Formula (I) or its pharmacologically acceptable salt, may also exist as an amorphous solid.

The term "amorphous," as used herein, means lacking a characteristic crystal shape or crystalline structure.

The term "amorphous" or "amorphous form" is intended to mean that the substance, component, or product in question is not substantially crystalline as determined, for instance, by XRPD or where the substance, component, or product in question, for example, is not birefringent or cubic when viewed using a polarized light microscope. In certain embodiments, a sample comprising an amorphous form of a substance may be substantially free of other amorphous forms and/or crystalline forms. This definition also applies when the crystal size is less than 2 nanometers. An amorphous form of the invention may be established by using additives, including solvents.

A "pharmaceutically acceptable salt" refers to the organic or inorganic salts of a compound disclosed herein. Pharmaceutically acceptable salts are well known in the art. For example, S. M. Berge et al., describe pharmaceutically acceptable salts in detail in J. Pharmaceutical Sciences, 66: 1-19, 1977, incorporated herein by reference. Examples of pharmaceutically acceptable, non-toxic salts include, but are not limited to, salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid or malonic acid.

Other pharmaceutically acceptable salts include adipate, alginate, ascorbate, aspartate, benzenesulfonate, benzoate, bisulfate, borate, butyrate, camphorate, camphor sulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal (for instance, $Na^+$, $Li^+$, $K^+$, $Ca^{+2}$, and $Mg^{+2}$), ammonium, and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate, and aryl sulfonate.

For therapeutic purposes, the salts of the active ingredients of the compounds according to the present invention are physiologically acceptable, i.e. they are salts derived from physiologically acceptable acids or bases; however, salts that are not physiologically acceptable acids or bases may also be used, for example, in the preparation or purification of physiologically acceptable compounds. All salts, whether derived from physiologically acceptable acids or bases, are within the scope of the present invention.

"Stereoisomers" refers to compounds that have an identical chemical constitution but differ with regard to the arrangement of the atoms or groups in space. Stereoisomers include enantiomer, diastereomers, conformer (rotamer), geometric (cis/trans) isomer, atropisomer, etc.

"Chiral" refers to molecules that have the property of non-superimposability of the mirror image partner, while the term "achiral" refers to molecules that are superimposable on their mirror image partner.

"Enantiomers" refers to two stereoisomers of a compound that are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties, or biological activities. Mixtures of diastereomers may separate under high-resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example, the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents or resolved using conventional techniques. If the compound contains a double bond, the substituent may be E or Z configuration. If the compound contains a disubstituted cycloalkyl, the cycloalkyl substituent may have a cis- or trans configuration.

Any resulting mixtures of stereoisomers can be separated on the basis of the physicochemical differences of the constituents into the pure or substantially pure geometric isomers, enantiomers, diastereomers, for example, by chromatography and/or fractional crystallization.

The term "tautomer" or "tautomeric form" refers to structural isomers of different energies which are interconvertible via a low energy barrier. Where tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by the reorganization of some of the bonding electrons. A specific example of keto-enol tautomerization is the interconversion of pentane-2,4-dione and 4-hydroxy-pent-3-en-2-one tautomers. Another example of tautomerization is phenol-keto tautomerization. A specific example of phenol-keto tautomerization is the interconversion of pyridin-4-ol and pyridin-4(1H)-one tautomer. Unless otherwise stated, all tautomeric forms of the compounds disclosed herein are within the scope of the invention.

A compound, according to the present invention, can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

The term "prodrug" refers to a compound that is transformed in vivo into a compound of formula (I). Such a transformation can be effected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example, those phosphates resulting from the phosphorylation of an OH group on the parent compound. The prodrug can be used to enhance solubility, absorption, and lipophilicity to optimize drug delivery, bioavailability, and drug efficacy. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, each of which is incorporated herein by reference.

As used herein, the term "treat," "treating," or "treatment" of any disease or disorder refers in one embodiment to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter, including those which may not be discernible by the patient. In yet another embodiment, "treat," "treating," or "treatment" refers to modulating the disease or disorder, either physically (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder.

Compounds according to the present invention include compounds that differ only in the presence of one or more isotopically enriched atoms. For example, compounds may have the present structures except for the replacement of hydrogen by deuterium or tritium or the replacement of a carbon by a $^{13}C$- or $^{14}C$-enriched carbon.

In the present invention, m represents micromoles per liter; mmol is millimoles per liter; equiv. stands for equivalent.

Evaluation of Anti-SARS-CoV-2 Activity for the Test Compounds

Another aspect of the present invention relates to a method for the evaluation of the test compounds for their antiviral activity SARS-CoV-2, including steps for treating samples suspected or confirmed to be positive for SARS-CoV-2 using the compounds described in the present invention.

Compounds according to the present invention can be used as an anti-SARS-CoV-2 agent or its intermediate or have the applications as described below. The anti-SARS-CoV-2 compound binds to a position on a surface or in a cavity that is a unique geometry of SARS-CoV-2. Compounds can bind to SARS-CoV-2 with a varying degree of reversibility. Compounds with a mainly irreversible binding are ideal candidates for the method of the present invention. Once labeled, compositions with a nearly irreversible binding can be used as probes for the detection of SARS-CoV-2. Thus, the invention relates to a method for detecting SARS-CoV-2 in specimens suspected or confirmed to be positive for SARS-CoV-2, which includes the following steps: treating a suspected specimen with a composition containing a compound from presented invention bound to a marker and observe the effect from the sample on the activity of markers. Suitable markers are well known in the field of diagnostics, including stable free radicals, fluorophores, radioisotopes, enzymes, chemiluminescent groups, and chromogens. The compounds, according to the present invention, are labeled in a conventional manner using functional groups, such as hydroxyl, carboxyl, sulfhydryl, or amino.

In the context of the invention, a specimen suspected or confirmed to be positive for SARS-CoV-2 includes natural or artificial materials, such as living organisms; tissue or cell cultures; biological samples, such as biomaterial samples (blood, serum, urine, cerebrospinal fluid, tears, sputum, saliva, tissue samples, etc.); laboratory samples; samples of food, water or air; sample of biological products such as cell extracts, especially recombinant cell extracts for the synthesis of required glycoproteins, etc. Typically, the sample would be suspected or confirmed to be positive for SARS-CoV-2, often a pathogen, such as the SARS-CoV-2. Samples can be contained in any medium, including water and organic solvents/water mixtures. Samples include living organisms, such as humans, and artificial materials, such as cell cultures.

The treatment step of the invention includes adding a composition of the invention to the sample or a precursor of the composition to the sample. The add steps include any of the methods described above.

If needed, any methods, including direct or indirect detection of SARS-CoV-2, can be used for the observation of the antiviral activity of the compounds according to the present invention. The detection methods for SARS-CoV-2 include quantitative, qualitative, and semi-quantitative methods.

Screening of Anti-SARS-CoV-2 Composition

The compounds, according to the present invention, are particularly useful for preventing, mitigating, or treating human or non-human animal SARS-CoV-2 infections. The cell-based assays should be the primary screening tool for anti-SARS-CoV-2 compounds for humans.

The composition according to the present invention is screened for compounds with anti-SARS-CoV-2 activity by any conventional technique for evaluating the antiviral activity. In the context of the present invention, the composition with anti-SARS-CoV-2 activity is typically first screened, followed by testing its in vivo antiviral activity. Combinations with Ki value in vitro (inhibition constant) less than approximately $5\times10^{-6}$ M and preferably less than approximately $1\times10^{-7}$ M are preferred for further application in vivo. Useful in vitro screening has been described in detail in the published literature and some examples according to the present invention describe appropriately in vitro assays.

Pharmaceutical Preparations

The compounds, according to the present invention, are prepared from conventional carriers and excipients. Although the active ingredients can be administered individually, it is preferable to make them into pharmaceutical preparations. The preparation according to the present invention, whether for veterinary or human use, contains at least one of the active ingredients as defined above and one or more acceptable carriers, and optionally contains other therapeutic ingredients, in particular those additional therapeutic ingredients disclosed herein. The carrier must be "acceptable," meaning that it is compatible with other components in the product and is biologically harmless to its recipient.

Preparation includes the suitable routes above. The preparation can be conveniently prepared in unit dosage form by any method known to the pharmaceutical field. The technology and agents are generally available at Remington's Pharmaceutical Sciences (Mack Publishing Co., Easton, Pa.). Such methods include steps for mixing the active ingredient with a carrier constituting one or more auxiliary components. In general, pharmaceutical preparations are made as follows: by mixing the active ingredient with a liquid carrier or a finely dispersed solid carrier or both to ensure a uniform mixture, and then, if necessary, forming the product.

The invention further provides a veterinary composition comprising at least one of the active ingredients as defined above and an acceptable veterinary carrier for such use.

An acceptable veterinary carrier is a substance used for veterinary composition purposes, which can be a solid, liquid, or gaseous substance that is inert or acceptable in the field of veterinary medicine and is compatible with the active ingredient. The veterinary compositions can be administered orally, parenterally, or by any other route required.

Route of Administration

One or more compounds, according to the present invention (referred to herein as active ingredients), are administered by any appropriate route for the condition being treated. An appropriate route of administration includes oral, rectal, nasal, pulmonary, local (including buccal and sublingual), and extragastrointestinal (including subcutaneous, intramuscular, intravenous, intradermal, intrathecal, and epidural). The preferred route may vary according to the patient's condition. The compounds, according to the present invention, have the advantages that they can be administered orally.

Compound Metabolites

In vivo metabolites of the compounds described herein also fall within the scope of the present invention to the extent that such products are novel and not obvious in relation to the prior art. These metabolites can be produced from the compound according to the present invention by oxidation, reduction, hydrolysis, amidation, esterification, etc., primarily as a result of enzymatic processes. The present invention, therefore, provides the novel and non-obvious metabolites produced by sufficient exposure to mammals over a period of time. Such products are typically identified as following steps:

the preparation of a compound of the present invention that is radiologically labeled (e.g., $^{14}C$ or $^{3}H$) then apply to an animal, such as a rat, mouse, guinea pig, monkey, or human being, at a detectable dose (e.g., greater than approximately 0.5 mg/kg) gastroenterically for a sufficient time (typically, approximately 30 seconds to 30 hours) to allow metabolism to occur, then isolate its products from urine, blood, or other biological samples. The structure of the metabolites was determined by MS or NMR analysis as described in the literature. In general, metabolites are analyzed in the same way as conventional drug metabolism studies as known in the field.

Formulations and methods for determining the in vitro gastrointestinal stability of compounds are known. The compound, according to this invention, is defined as a stable substance in the gastrointestinal tract, where less than approximately 50 molar percentage of the protected groups are metabolized in intestinal or gastric fluid substitutes after incubation at 37° C. for 1 h. It should be noted that a stable compound in the gastrointestinal tract might also be hydrolyzed in the body. The prodrugs, according to the present invention, are typically stable in the digestive system, but they usually hydrolyze to the parent drug in the digestive cavity, liver, or other metabolic organs or in cells.

The dose and methods of using compounds of Formula (I), its prodrug, or its pharmaceutically acceptable salt for different patients depend on many factors, including the patient's age, weight, gender, health condition, nutritional status, drug activity, time course, metabolic rate, the severity of the illness, and the subjective judgment of the physician. The effective dose of the active ingredient depends, at a minimum, on the nature of the disease to be treated, toxicity (whether the compound is used to prevent or treat viral infection), method of delivery, and drug formulation will be determined by clinicians using routine dose escalation studies. Doses can be expected from about 0.0001 to 100 mg/kg body weight per day; typically, about 0.01 to 10 mg/kg; more typically, about 0.01 to 5 mg/kg; the most typically, about 0.05 to 0.5 mg/kg. For example, for adults weighing approximately 70 kg, the candidate daily dose will be in the range of 1 mg to 1,000 mg, preferably 5 mg to 500 mg, and can be in the form of a single dose or multiple doses.

All the above dosage forms can be prepared according to the conventional methods in the field of pharmacy.

The methods may include administering to a subject in need thereof a compound or composition as described herein.

The following non-limiting examples are intended to be purely illustrative of some aspects and embodiments and show specific experiments that were carried out in accordance with the disclosure.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Acronyms |
|---|---|
| ACN | Acetonitrile |
| DCC | Dicyclohexylcarbodiimide |
| DCM | Dichloromethane |
| DMAP | 4-Dimethylaminopyridine |
| EA | Ethyl acetate |
| EDMA | N,N-Dimethylethylamine |
| MeOH | Methanol |
| PE | Petroleum ether |
| RDV | remdesivir |
| rt | Room temperature |
| TEA | Triethylamine |
| TLC | Thin layer chromatography |
| THF | Tetrahydrofuran |

In the present invention, compound structures are represented by the abbreviations of some compounds:

TABLE 2

List of abbreviations and acronyms.

| Abbreviations | Compound structure |
|---|---|
| GS-441524 | 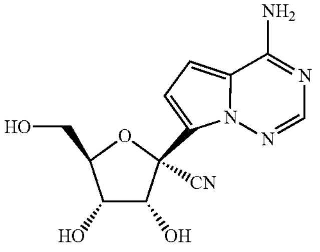 [SMILES: N#C[C@@]1(c2ccc3c(N)ncnn23)O[C@H](CO)[C@@H](O)[C@H]1O] |

TABLE 2-continued

List of abbreviations and acronyms.

| Abbreviations | Compound structure |
|---|---|
| Intermediate 5 of RDV | 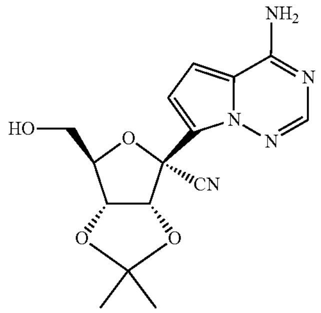 [SMILES: CC1(C)O[C@H]2[C@@H](O1)[C@](C#N)(c1ccc3c(N)ncnn13)O[C@@H]2CO] |

Example 1. (2R,3R,4R,5R)-2-cyano-2-(4-isobutyramidopyrrolo[2,1-f][1,2,4]triazin-7-yl)-5-((isobutyryloxy)methyl)tetrahydrofuran-3,4-diyl bis(2-methylpropanoate) (ATV001

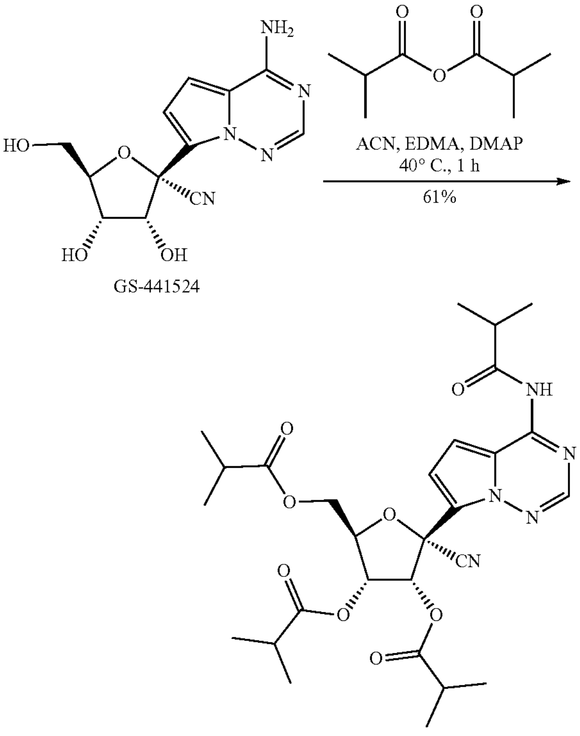

GS-441524

ATV001

To a suspension of GS-441524 (594 mg, 2 mmol), 4-dimethylaminopyridine (50 mg, 0.4 mmol), EDMA (1.2 mL, 11 mmol) in ACN (10 mL) was added isobutyric anhydride (1.66 mL, 10 mmol). The mixture was stirred at 40° C. for 1 h. The mixture was concentrated under reduced pressure to give a crude mixture, which was then purified by silica gel column chromatography (MeOH/DCM: V/V=5/95), affording compound ATV001 as a colorless sticky liquid (624 mg, 61%). HPLC retention time: 3.319 min (water/ACN=10/90; flow rate 1 mL/min; wavelength: 254 nm). $^1$H NMR (400 MHz, $CDCl_3$) δ 9.33 (s, 1H), 8.21 (s, 1H), 7.34 (d, J=4.9 Hz, 1H), 7.06 (d, J=4.9 Hz, 1H), 6.23 (d, J=5.8 Hz, 1H), 5.51 (dd, J=5.8, 4.3 Hz, 1H), 4.67 (q, J=4.0 Hz, 1H), 4.41 (qd, J=12.3, 3.9 Hz, 2H), 3.19 (dt, J=13.4, 6.7 Hz, 1H), 2.74-2.62 (m, 2H), 2.56 (dq, J=14.0, 7.0 Hz, 1H), 1.35-1.10 (m, 24H); $^{13}C$ NMR (101 MHz, $CDCl_3$) δ 177.46, 176.45, 175.76, 174.98, 151.38, 145.87, 123.21, 118.26, 114.91, 113.27, 106.29, 81.60, 76.86, 71.97, 70.54, 62.56, 36.01, 33.85, 33.84, 33.74, 19.13, 19.11, 18.91, 18.85, 18.81, 18.70, 18.67, 18.54.

Example 2. (2R,3R,4R,5R)-2-(4-acetamidopyrrolo[2,1-f][1,2,4]triazin-7-yl)-5-(acetoxymethyl)-2-cyanotetrahydrofuran-3,4-diyl diacetate (ATV002)

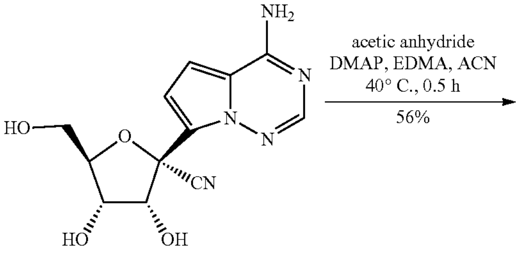

GS-441524

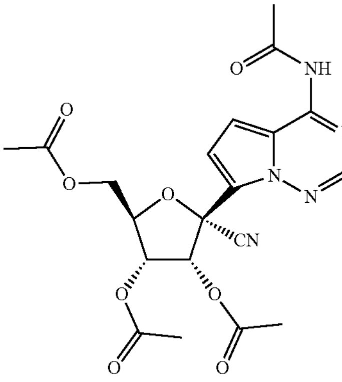

ATV002

To a suspension of GS-441524 (594 mg, 2 mmol), 4-dimethylaminopyridine (50 mg, 0.4 mmol), EDMA (1.2 mL, 11 mmol) in ACN (10 mL) was added acetic anhydride (1 mL, 10.6 mmol). The mixture was stirred at 40° C. for 0.5 h. The mixture was concentrated under reduced pressure to give a crude mixture, which was then purified by silica gel column chromatography (MeOH/DCM: V/V=5/95), affording compound ATV002 as a white solid (518 mg, 56% yield). HPLC retention time: 2.162 min (water/ACN=10/90; flow rate 1 mL/min; wavelength 254 nm). $^{1}H$ NMR (400 MHz, $CDCl_3$) δ 9.16 (s, 1H), 8.23 (s, 1H), 7.21 (d, J=4.8 Hz, 1H), 7.11 (d, J=4.8 Hz, 1H), 6.25 (d, J=5.9 Hz, 1H), 5.56-5.41 (m, 1H), 4.65 (dd, J=8.5, 4.7 Hz, 1H), 4.47 (dd, J=12.3, 3.6 Hz, 1H), 4.34 (dd, J=12.3, 4.9 Hz, 1H), 2.63 (s, 3H), 2.19 (s, 3H), 2.17 (s, 3H), 2.09 (s, 3H); $^{13}C$ NMR (101 MHz, $CDCl_3$) δ 172.03, 170.43, 169.84, 169.03, 151.01, 146.16, 122.96, 117.82, 114.85, 114.01, 103.74, 81.00, 77.21, 71.79, 70.60, 62.58, 26.12, 20.76, 20.53, 20.51.

Example 3. (2R,3R,4R,5R)-5-(acetoxymethyl)-2-(4-aminopyrrolo[2,1-f][1,2,4]triazin-7-yl)-2-cyanotetrahydrofuran-3,4-diyl diacetate (ATV003)

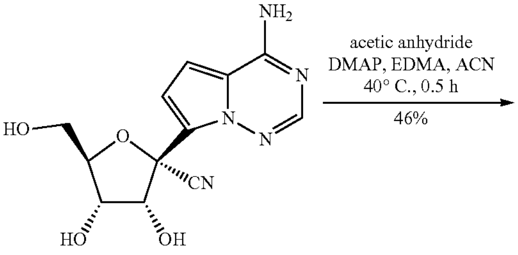

GS-441524

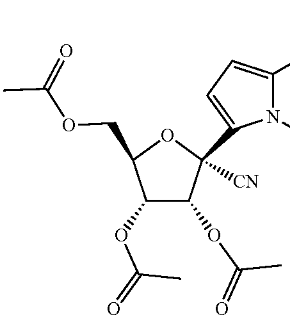

ATV003

To a suspension of GS-441524 (594 mg, 2 mmol), 4-dimethylaminopyridine (50 mg, 0.4 mmol), EDMA (1.2 mL, 11 mmol) in ACN (10 mL) was added acetic anhydride (1 mL, 10.6 mmol). The mixture was stirred at 40° C. for 0.5 h. The mixture was concentrated under reduced pressure to give a crude mixture, which was then purified by silica gel column chromatography (MeOH/DCM: V/V=5/95), affording compound ATV003 as a white solid (384 mg, 46%). HPLC retention time: 2.157 min (water/ACN=10/90; flow rate 1 mL/min; wavelength 254 nm). $^{1}H$ NMR (400 MHz, $CDCl_3$) δ 7.94 (s, 1H), 6.92 (d, J=4.6 Hz, 1H), 6.61 (d, J=4.7 Hz, 1H), 6.30 (d, J=5.9 Hz, 3H), 5.61-5.43 (m, 1H), 4.63 (dd, J=8.7, 4.9 Hz, 1H), 4.49 (dd, J=12.2, 3.7 Hz, 1H), 4.34 (dd, J=12.2, 5.1 Hz, 1H), 2.18 (s, 3H), 2.16 (s, 3H), 2.08 (s, 3H); $^{13}C$ NMR (101 MHz, $CDCl_3$) δ 170.55, 169.91, 169.16, 155.54, 147.39, 121.63, 117.23, 115.28, 112.61, 100.23, 80.85, 77.48, 71.90, 70.67, 62.67, 20.77, 20.55.

Example 4. (2R,3R,4R,5R)-2-(4-aminopyrrolo[2,1-f][1,2,4]triazin-7-yl)-2-cyano-5-((isobutyryloxy)methyl)tetrahydrofuran-3,4-diyl bis(2-methylpropanoate) (ATV004)

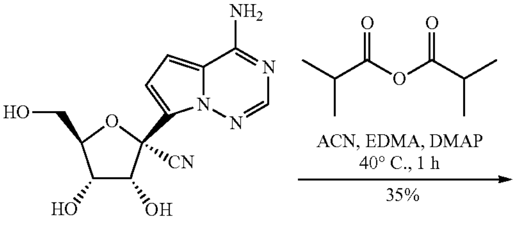

GS-441524

-continued

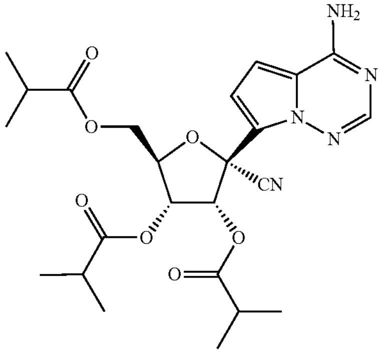

ATV004

To a suspension of GS-441524 (594 mg, 2 mmol), 4-dimethylaminopyridine (50 mg, 0.4 mmol), EDMA (1.2 mL, 11 mmol) in ACN (10 mL) was added isobutyric anhydride (1.66 mL, 10 mmol). The mixture was stirred at 40° C. for 1 h. The mixture was concentrated under reduced pressure to give a crude mixture, which was then purified by silica gel column chromatography (MeOH/DCM: V/V=5/95), affording compound ATV004 as a colorless sticky liquid (410 mg, 35%). HPLC retention time: 2.767 min (water/ACN=10/90; flow rate 1 mL/min; wavelength 254 nm). $^{1}$H NMR (400 MHz, $CDCl_3$) δ 7.89 (s, 1H), 6.86 (d, J=4.7 Hz, 1H), 6.70 (d, J=4.7 Hz, 1H), 6.28 (d, J=5.9 Hz, 1H), 5.53 (dd, J=5.7, 4.4 Hz, 1H), 4.65 (q, J=4.1 Hz, 1H), 4.42 (qd, J=12.3, 4.1 Hz, 2H), 2.75-2.51 (m, 3H), 1.32-1.10 (m, 18H); $^{13}$C NMR (101 MHz, $CDCl_3$) δ 176.58, 175.85, 175.11, 155.65, 146.56, 122.08, 117.09, 115.34, 112.03, 101.09, 81.50, 77.04, 71.99, 70.63, 62.66, 33.85, 33.82, 33.74, 18.96, 18.82, 18.78, 18.69, 18.67, 18.54.

Example 5. (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (Compound 5)

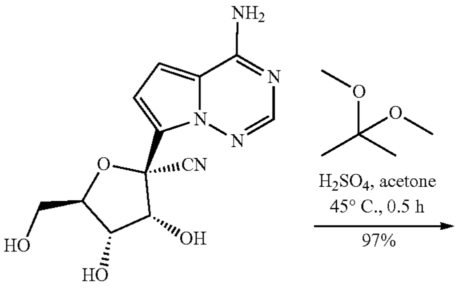

GS-441524

-continued

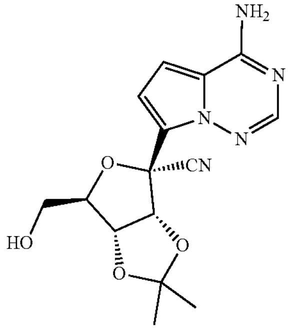

5

To a suspension of GS-441524 (5.62 g, 19.3 mmol) in acetone (30 mL) was added 2,2-dimethoxypropane (11.5 mL, 92.6 mmol), and then conc. $H_2SO_4$ (1.34 mL, 25.1 mmol) was added dropwise at room temperature. The mixture was stirred at 45° C. After 0.5 h, the reaction was completed as monitored by TLC. The mixture was neutralized with saturated $NaHCO_3$ and then concentrated under reduced pressure. The residue was extracted with EA (100 mL×3). The combined organic extracts were washed with water and brine, dried with anhydrous $Na_2SO_4$, filtered, and concentrated in vacuo to give the crude product, which was purified by silica gel column chromatography (PE/EA: V/V=1/2), affording compound 5 as a white solid (6.20 g, 97%). $^{1}$H NMR (400 MHz, Chloroform-d) δ 7.95 (s, 1H), 7.11 (d, J=4.7 Hz, 1H), 6.69 (dd, J=4.8, 2.4 Hz, 1H), 5.77 (s, 2H), 5.42 (d, J=6.6 Hz, 1H), 5.24 (dd, J=6.6, 2.4 Hz, 1H), 4.67 (q, J=1.9 Hz, 1H), 3.99 (dd, J=12.5, 1.9 Hz, 1H), 3.84 (dd, J=12.5, 1.7 Hz, 1H), 1.81 (s, 3H), 1.40 (s, 3H).

Example 6. pentyl (7-((2R,3R,4R,5R)-2-cyano-3,4-bis(((pentyloxy)carbonyl)oxy)-5-((((pentyloxy)carbonyl)oxy)methyl)tetrahydrofuran-2-yl)pyrrolo[2,1-f][1,2,4]triazin-4-yl)carbamate (Compound 6)

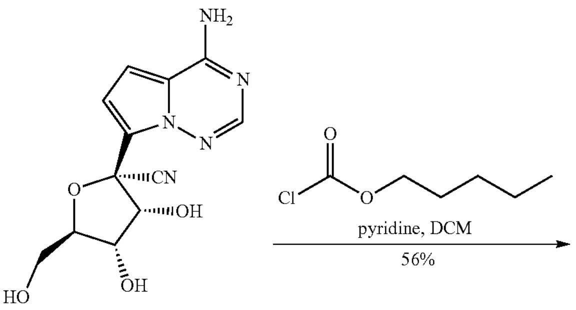

GS-441524

-continued

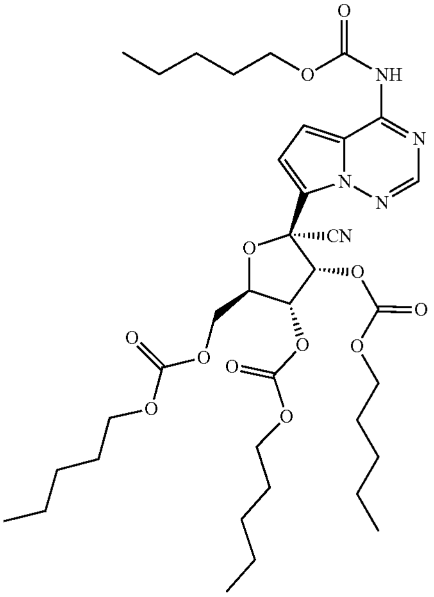

6

To a suspension of GS-441524 (50 mg, 0.17 mmol) in DCM (2.5 mL) and pyridine (80.7 mg, 1.02 mmol) was added n-amyl chloroformate (107.5 mg, 0.71 mmol) at 0° C. under argon. The mixture was warmed up to rt and stirred for additional 3 h. The reaction was monitored by TLC until completion. The crude solid was collected in vacuo, then was purified by chromatography on silica gel (n-hexane/EA: V/V=10:1), affording compound 6 as a colorless liquid (71.7 mg, 56% yield). $^{1}$H NMR (400 MHz, Chloroform-d) δ 9.00 (s, 1H), 8.27 (s, 1H), 7.39 (d, J=4.9 Hz, 1H), 7.17 (d, J=5.0 Hz, 1H), 6.12 (d, J=5.8 Hz, 1H), 5.38 (t, J=5.9 Hz, 1H), 4.69 (q, J=4.6 Hz, 1H), 4.57 (dd, J=12.1, 3.4 Hz, 1H), 4.40 (dd, J=12.1, 4.7 Hz, 1H), 4.28 (t, J=6.8 Hz, 2H), 4.23-4.07 (m, 6H), 1.85-1.60 (m, 8H), 1.36 (ddp, J=14.4, 7.0, 3.5 Hz, 16H), 1.02-0.83 (m, 12H); $^{13}$C NMR (101 MHz, Chloroform-d) δ 154.8, 154.0, 153.5, 151.7, 151.5, 146.0, 122.7, 117.7, 114.2, 114.1, 107.0, 79.9, 77.3 (d, J=24.5 Hz), 74.6, 72.8, 69.5, 69.2, 68.7, 66.9, 65.1, 28.3, 28.2, 28.1, 28.1, 27.8, 27.7, 27.6, 27.6, 22.2, 13.9 (d, J=4.4 Hz).

Example 7. Pentyl (7-((2R,3R,4S,5R)-2-cyano-3,4-dihydroxy-5-(hydroxymethyl)tetrahydrofuran-2-yl)pyrrolo[2,1-f][1,2,4]triazin-4-yl)carbamate (ATV005)

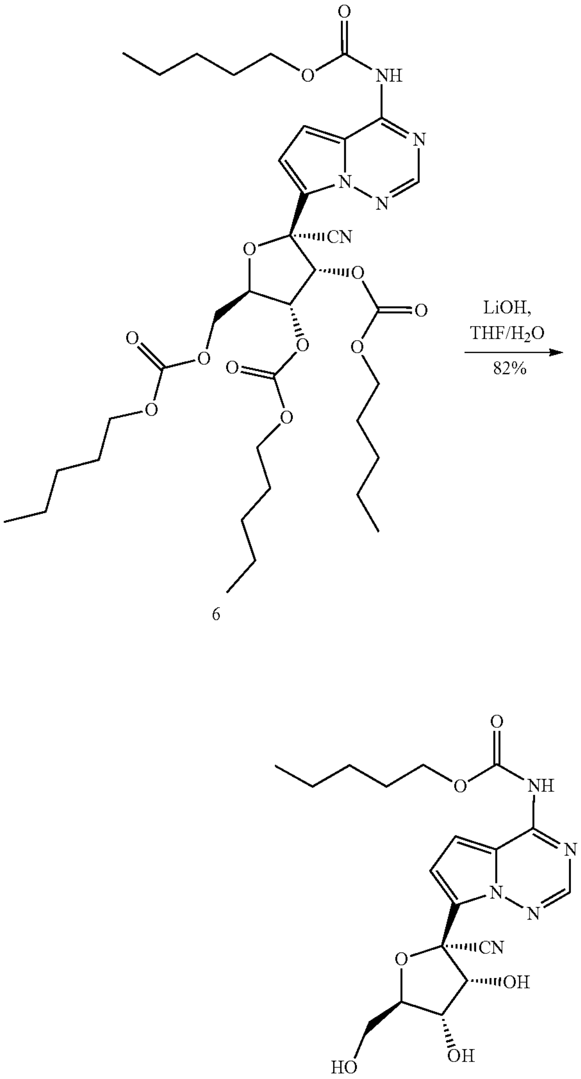

6

ATB005

To a solution of compound 6 (58.3 mg, 0.078 mmol) in THF (2 mL) and water (1 mL) was added lithium hydroxide (18.7 mg, 0.78 mmol). The reaction was stirred at rt for 6 h and was monitored by TLC analysis. After completion, the solvent was removed under reduced pressure and the residue was purified by chromatography on silica gel (3-10% MeOH in DCM) to afford compound ATV005 as a white solid (32.7 mg, 82%). HPLC retention time: 2.173 min (water/ACN=10/90; flow rate 1 mL/min; wavelength 254 nm). $^{1}$H NMR (400 MHz, Methanol-d4) δ 8.20 (s, 1H), 7.25 (d, J=4.7 Hz, 1H), 7.15 (d, J=4.8 Hz, 1H), 4.82 (d, J=7.4 Hz, 2H), 4.26 (t, J=6.6 Hz, 3H), 4.15 (t, J=5.5 Hz, 1H), 3.87 (dd, J=12.4, 3.1 Hz, 1H), 3.74 (dd, J=12.4, 4.4 Hz, 1H), 1.82-1.69 (m, 2H), 1.49-1.36 (m, 4H), 0.95 (t, J=6.9 Hz, 3H); $^{13}$C NMR (101 MHz, Methanol-d4) δ 153.5, 153.2, 147.3, 127.0, 118.6, 117.6, 114.3, 104.6, 87.2, 81.2, 75.6, 71.8, 67.3, 62.7, 29.6, 29.1, 23.4, 14.3.

Example 8. ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyrate (Compound 7)

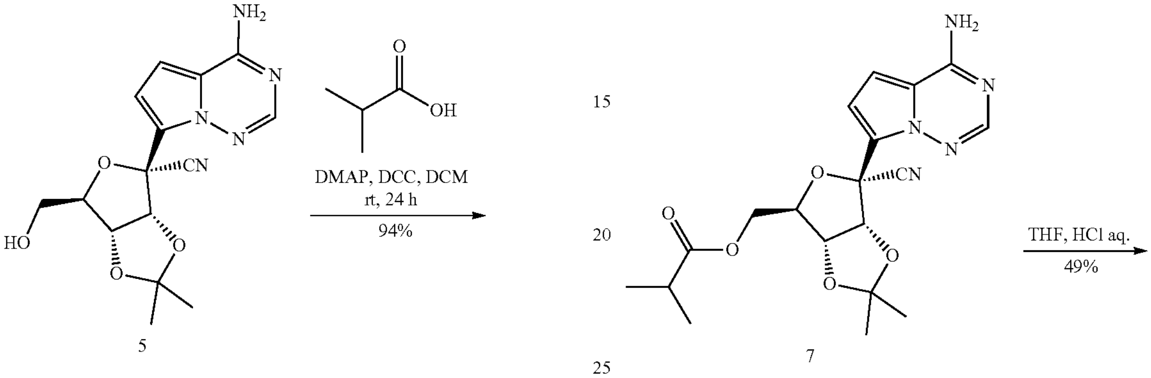

5

7

To a solution of compound 5 (1.50 g, 4.5 mmol), isobutyric acid (0.42 mL, 4.5 mmol), 4-dimethylaminopyridine (55.40 mg, 0.45 mmol) in DCM (15 mL) was added dicyclohexylcarbodiimide (1.02 g, 4.9 mmol). The mixture was stirred at rt for 24 h. The suspension was filtered and the filtrate was washed with 30 mL of saturated solution of $Na_2CO_3$ and then with 30 mL of an aqueous solution of citric acid (20% w/v). The organic layer was dried with $Na_2SO_4$ and the solvent was removed under reduced pressure. The products were purified by column chromatography (PE/EA=1:1). Compound 7 was isolated as a white solid (1.71 g, 94% yield). $^1H$ NMR (400 MHz, $CDCl_3$) δ (ppm): 7.99 (s, 1H), 6.99 (d, J=4.6 Hz, 1H), 6.62 (d, J=4.6 Hz, 1H), 5.72 (br, 2H), 5.49 (d, J=6.8 Hz, 1H), 4.93-4.90 (dd, J=6.8 Hz, 4.3 Hz, 1H), 4.61-4.58 (q, J=4.4 Hz, 1H), 4.44-4.26 (m, 2H), 2.61-2.50 (m, 1H), 1.77 (s, 3H), 1.42 (s, 3H), 1.17-1.14 (q, J=3.8 Hz, 6H); $^{13}C$ NMR (100 MHz, $CDCl_3$) δ (ppm): 176.7, 155.2, 147.3, 123.5, 117.2, 116.7, 115.6, 112.6, 100.0, 83.8, 83.0, 82.0, 81.4, 63.1, 33.8, 26.4, 25.6, 18.9.

Example 9. ((2R,3S,4R,5R)-5-(4-aminopyrrolo[2,1-f][1,2,4]triazin-7-yl)-5-cyano-3,4-dihydroxytetrahydrofuran-2-yl)methyl isobutyrate (ATV006)

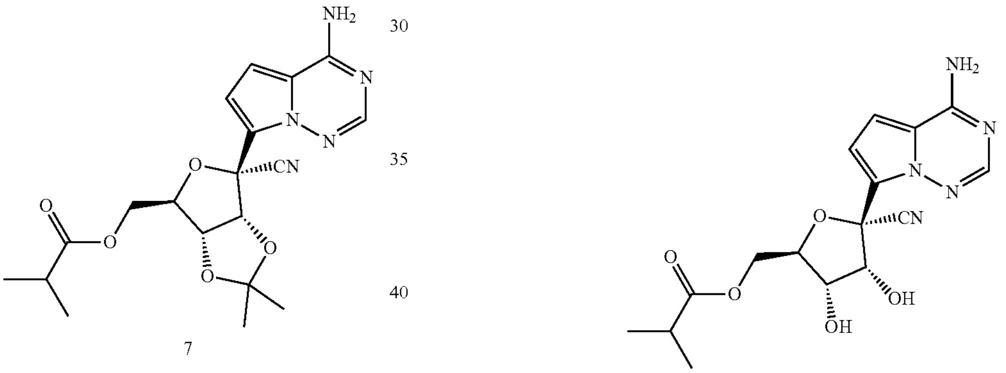

7

ATV006

Compound 7 (1.50 g, 3.7 mmol) was dissolved in 37% hydrochloric acid aqueous solution (3 mL) and THF (15 mL). After stirring for 6 h, pH was adjusted to 8 with $Na_2CO_3$, the solvent was removed in vacuo, and the residue was purified by silica gel column chromatography (PE/EA: V/V=1/3), affording compound ATV006 as a white solid (0.66 g, 49% yield). HPLC retention time: 2.036 min (water/ACN=10/90; flow rate 1 mL/min; wavelength 254 nm). $^1H$ NMR (600 MHz, DMSO-d6) δ: 7.93 (s, 1H), 7.89 (br, 2H), 6.92 (d, J=4.3 Hz, 1H), 6.81 (d, J=4.3 Hz, 1H), 6.32 (d, J=5.9 Hz, 1H), 5.38 (d, J=5.7 Hz, 1H), 4.7 (t, J=5.2 Hz, 1H), 4.32-4.30 (m, 1H), 4.25-4.22 (m, 1H), 4.19-4.16 (m, 1H), 3.98-3.95 (q, J=5.6 Hz, 1H), 2.55-2.50 (m, 1H), 1.06-1.05 (dd, J=6.8 Hz, 1.8 Hz, 6H); $^{13}C$ NMR (150 MHz, DMSO-d6) δ: 176.4, 156.1, 148.4, 124.0, 117.4, 117.0, 110.7, 101.3, 81.7, 79.5, 74.5, 70.6, 63.4, 33.6, 19.2, 19.1.

Example 10. ((2R,3S,4R,5R)-5-(4-aminopyrrolo[2,1-f][1,2,4]triazin-7-yl)-5-cyano-3,4-dihydroxytetrahydrofuran-2-yl)methyl acetate (ATV007)

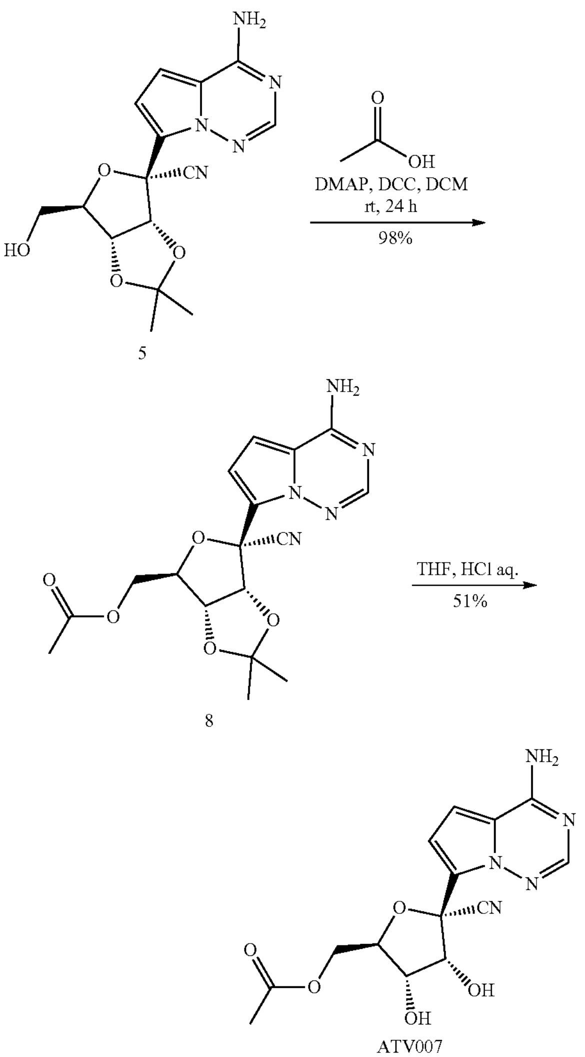

5

8

ATV007

Compound 8 was prepared by the general procedure for compound 7 as described in example 8 with acetic acid instead of isobutyric acid. Compound 8 was obtained as a white solid (1.78 g, 98%).

Compound ATV007 was prepared by the general procedure for compound ATV006 as described in example 9 with compound 8 as the starting material instead of compound 7. Compound ATV007 was obtained as a white solid (0.68 g, 51% yield). HPLC purity 98.74% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.89 (t, J=5.0 Hz, 2H), 4.87 (s, 1H), 4.43-4.41 (dd, J=12 Hz, 2.8 Hz, 1H), 4.37-4.34 (m, 1H), 4.30-4.27 (m, 1H), 4.13 (t, J=5.7 Hz, 1H), 2.03 (s, 3H); $^{13}$C NMR (150 MHz, $CD_3OD$) δ (ppm): 171.0, 155.8, 146.9, 124.2, 116.6, 116.2, 110.7, 101.1, 81.9, 80.2, 74.1, 70.7, 63.1, 19.3.

Example 11. ((2R,3S,4R,5R)-5-(4-aminopyrrolo[2,1-f][1,2,4]triazin-7-yl)-5-cyano-3,4-dihydroxytetrahydrofuran-2-yl)methyl propionate (ATV008)

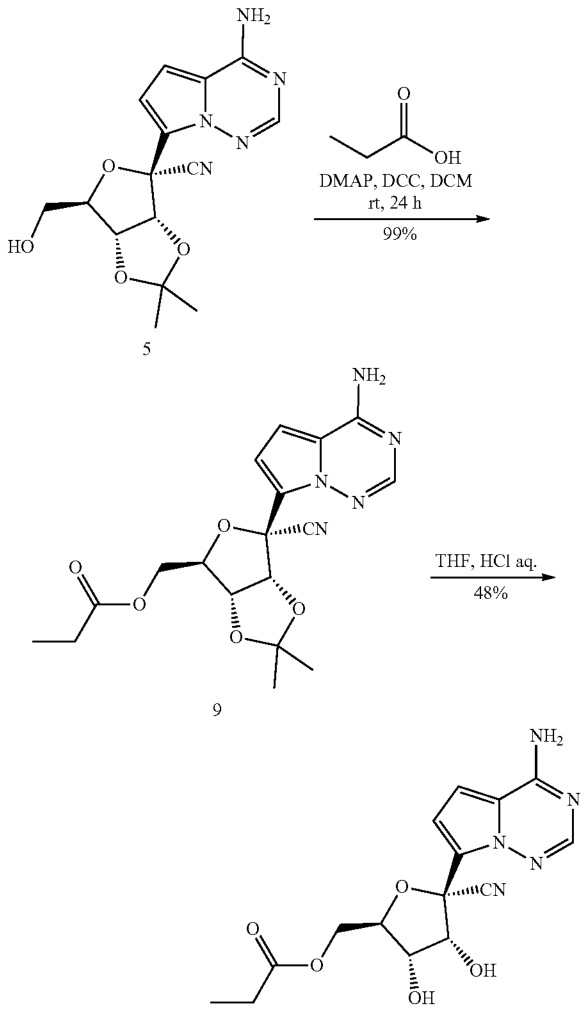

5

9

ATV008

Compound 9 was prepared by the general procedure for compound 7 as described in example 8 with propionic acid instead of isobutyric acid. Compound 9 was obtained as a white solid (1.74 g, 99% yield).

Compound ATV008 was prepared by the general procedure for compound ATV006 as described in example 9 with compound 9 as the starting material instead of compound 7. Compound ATV008 was obtained as a white solid (0.68 g, 48% yield). HPLC purity 98% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.90-6.88 (q, J=4.5 Hz, 2H), 4.87-4.86 (m, 1H), 4.46-4.43 (dd, J=12 Hz, 2.8 Hz, 1H), 4.37-4.36 (m, 1H), 4.31-4.28 (m, 1H), 4.15 (t, J=5.8 Hz, 1H), 2.38-2.28 (m, 2H), 1.08 (t, J=7.5 Hz, 3H); $^{13}$C NMR (150 MHz, $CD_3OD$) δ (ppm): 174.3, 155.8, 146.9, 124.2, 116.5, 116.2, 110.7, 101.1, 82.0, 80.1, 74.2, 70.7, 62.9, 26.7, 7.9.

Example 12. ((2R,3S,4R,5R)-5-(4-aminopyrrolo[2,1-f][1,2,4]triazin-7-yl)-5-cyano-3,4-dihydroxytetrahydrofuran-2-yl)methyl butyrate (ATV009)

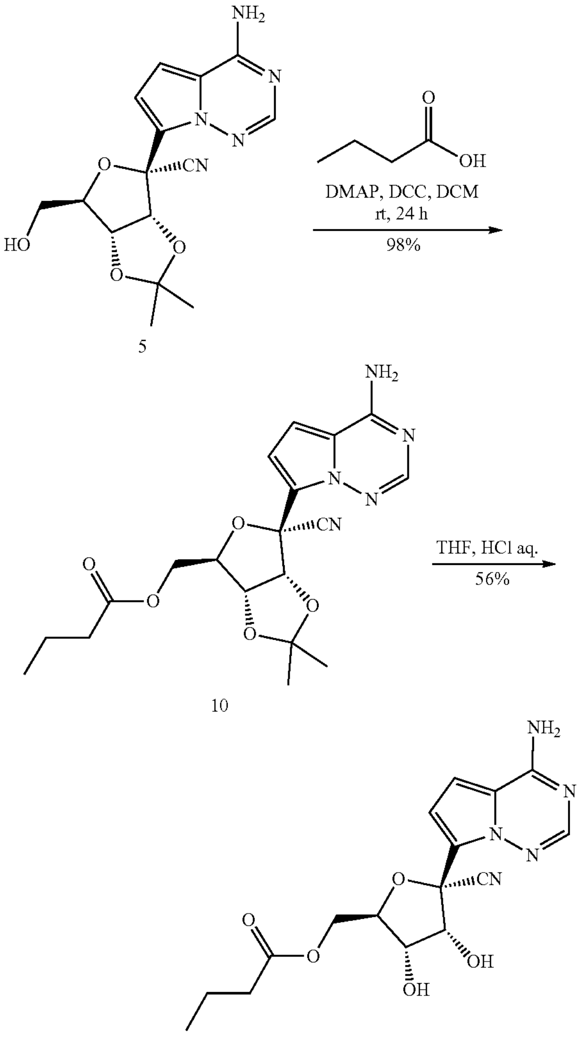

5

10

ATV009

Compound 10 was prepared by the general procedure for compound 7 as described in example 8 with n-butyric acid instead of isobutyric acid. Compound 10 was obtained as a white solid (1.78 g, 98%).

Compound ATV009 was prepared by the general procedure for compound ATV006 as described in example 9 with compound 10 as the starting material instead of compound 7. Compound ATV009 was obtained as a white solid (0.76 g, 56%). HPLC purity 97% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.90-6.88 (q, J=4.5 Hz, 2H), 4.87-4.86 (m, 1H), 4.44-4.42 (dd, J=12 Hz, 2.8 Hz, 1H), 4.37-4.35 (m, 1H), 4.31-4.28 (m, 1H), 4.14 (t, J=5.8 Hz, 1H), 2.32-2.23 (m, 2H), 1.62-1.56 (m, 2H), 0.91 (t, J=7.4 Hz, 3H); $^{13}$C NMR (150 MHz, $CD_3OD$) δ (ppm): 174.3, 155.9, 146.9, 124.3, 116.5, 116.2, 110.7, 101.1, 82.0, 80.1, 74.2, 70.7, 62.8, 35.4, 17.9, 12.5.

Example 13. ((2R,3S,4R,5R)-5-(4-aminopyrrolo[2,1-f][1,2,4]triazin-7-yl)-5-cyano-3,4-dihydroxytetrahydrofuran-2-yl)methyl nonanoate (ATV010)

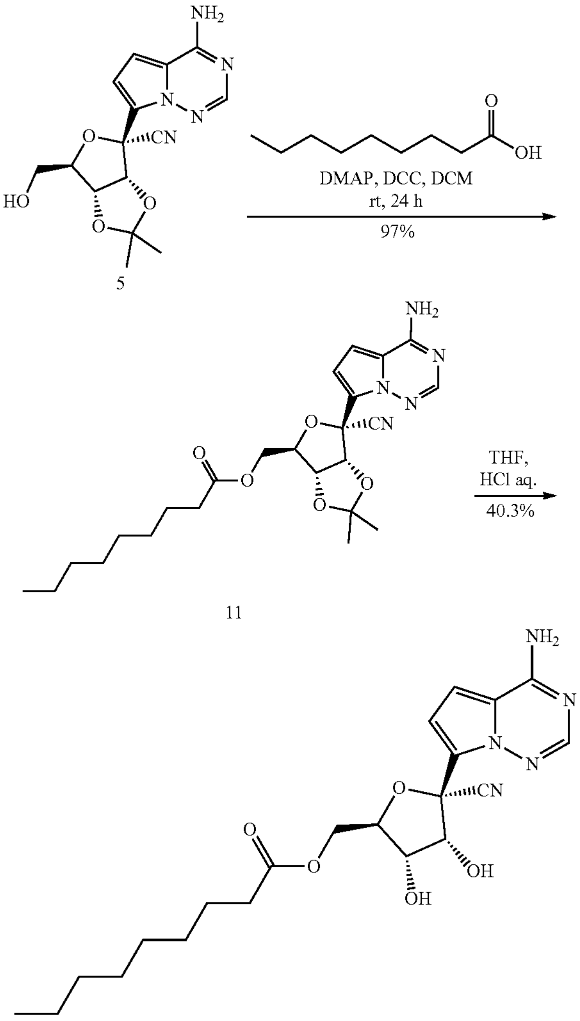

5

11

ATV010

Compound 11 was prepared by the general procedure for compound 7 as described in example 8 with pelargonic acid instead of isobutyric acid. Compound 11 was obtained as a white solid (2.07 g, 97%).

Compound ATV010 was prepared by the general procedure for compound ATV006 as described in example 9 with compound 11 as the starting material instead of compound 7. Compound ATV010 was obtained as a white solid (0.55 g, 40.3%). HPLC purity was 98% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.90-6.88 (q, J=4.5 Hz, 2H), 4.87-4.86 (m, 1H), 4.43-4.41 (dd, J=12 Hz, 2.8 Hz, 1H), 4.37-4.35 (m, 1H), 4.32-4.29 (m, 1H), 4.14 (t, J=5.8 Hz, 1H), 2.38-2.23 (m, 2H), 1.56-1.53 (m, 2H), 1.29-1.27 (m, 10H), 0.87 (t, J=7.0 Hz, 3H). $^{13}$C NMR (150 MHz, $CD_3OD$) δ (ppm): 173.7, 155.9, 146.9, 124.3, 116.5, 116.2, 110.7, 101.1, 82.0, 74.2, 70.7, 62.8, 33.5, 31.5, 28.8, 28.7, 24.6, 22.3.

Example 14. ((2R,3S,4R,5R)-5-(4-aminopyrrolo[2,1-f][1,2,4]triazin-7-yl)-5-cyano-3,4-dihydroxytetrahydrofuran-2-yl)methyl 2-ethylbutanoate (ATV011)

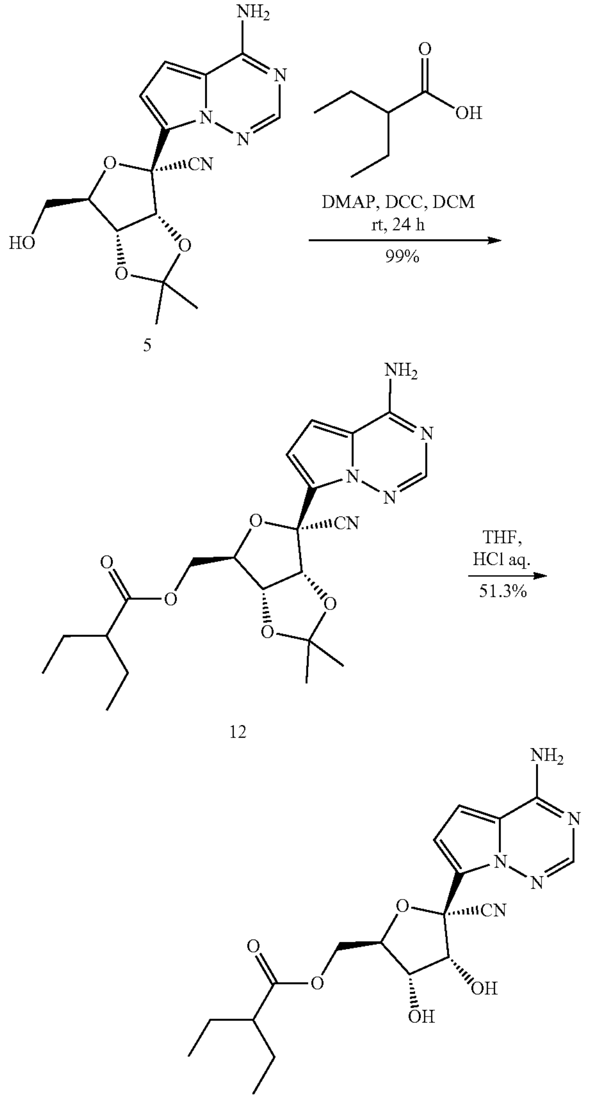

5

12

ATV011

Compound 12 was prepared by the general procedure for compound 7 as described in example 8 with 2-ethyl butyric acid instead of isobutyric acid. Compound 12 was obtained as a white solid (1.94 g, 99%).

Compound ATV011 was prepared by the general procedure for compound ATV006 as described in example 9 with compound 12 as the starting material instead of compound 7. Compound ATV011 was obtained as a white solid (0.70 g, 51.3%). HPLC purity 98.3% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.89 (s, 2H), 4.87-4.86 (m, 1H), 4.39-4.43 (dd, J=12 Hz, 2.8 Hz, 1H), 4.37-4.35 (m, 1H), 4.14 (t, J=5.8 Hz, 1H), 2.38-2.22 (m, 1H), 1.60-1.45 (m, 4H), 0.86-0.82 (m, 6H); $^{13}$C NMR (150 MHz, $CD_3OD$) δ (ppm): 176.1, 155.9, 146.9, 124.3, 116.6, 116.2, 110.7, 101.1, 81.9, 79.9, 74.2, 70.7, 62.8, 48.9, 24.7, 24.6, 10.7, 10.6.

Example 15. ((2R,3S,4R,5R)-5-(4-aminopyrrolo[2,1-f][1,2,4]triazin-7-yl)-5-cyano-3,4-dihydroxytetrahydrofuran-2-yl)methyl cyclopropanecarboxylate (ATV012)

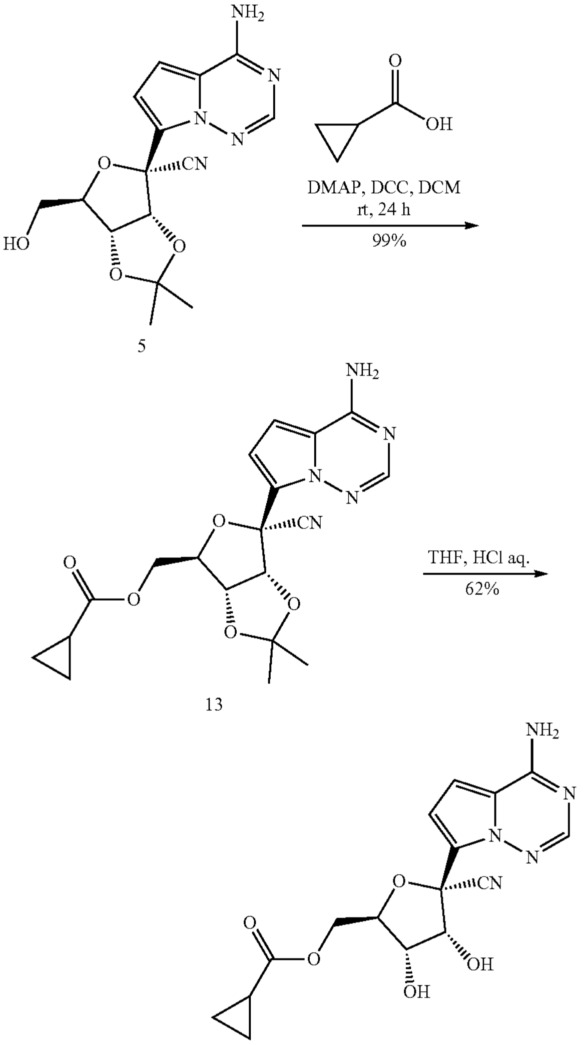

5

13

ATV012

Compound 13 was prepared by the general procedure for compound 7 as described in example 8 with cyclopropanoic acid instead of isobutyric acid. Compound 13 was obtained as a white solid (1.52 g, 99%).

Compound ATV012 was prepared by the general procedure for compound ATV006 as described in example 9 with compound 13 as the starting material instead of compound 7. Compound ATV012 was obtained as a white solid (0.98 g, 62%). HPLC purity 98.3% (OD-3; eluent, n-hexane/isopropanol=80/20; flow rate 0.8 mL/min; temperature 30° C.; wavelength 254 nm; HPLC analysis data are reported in relative area % and were not adjusted to weight %). $^{1}$H NMR (600 MHz, $CD_3OD$) δ (ppm): 7.86 (s, 1H), 6.89 (t, J=4.5 Hz, 2H), 4.87-4.86 (m, 1H), 4.46-4.44 (dd, J=12 Hz, 2.8 Hz, 1H), 4.36-4.34 (m, 1H), 4.29-4.26 (m, 1H), 4.15 (t, J=5.8 Hz, 1H), 1.64-1.60 (m, 1H), 0.92-0.87 (m, 4H); $^{13}C$ NMR (150 MHz, $CD_3OD$) δ (ppm): 174.9, 155.9, 146.9, 124.2, 116.6, 116.2, 110.7, 101.1, 80.2, 80.1, 74.2, 70.6, 63.0, 12.1, 7.5, 7.4.

Example 16. ((2R,3S,4R,5R)-5-(4-aminopyrrolo[2,1-f][1,2,4]triazin-7-yl)-5-cyano-3,4-dihydroxytetrahydrofuran-2-yl)methyl benzoate (ATV013)

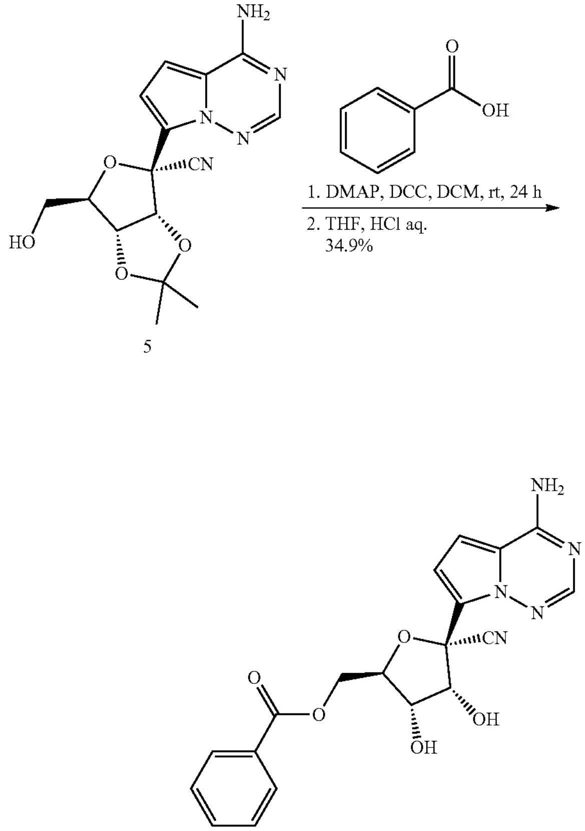

5

ATV013

Compound ATV013 was prepared by the general procedure for compound ATV006 as described in examples 8 and 9 (with benzoic acid instead of isobutyric acid for step 1). Compound ATV013 was obtained as a white solid (0.21 g, 34.9% overall yield). $^{1}H$ NMR (600 MHz, DMSO-$d_6$) δ (ppm): 7.92 (br, 2H), 7.90 (d, J=7.4 Hz, 2H), 7.86 (s, 1H), 7.68 (t, J=7.4 Hz, 1H), 7.52 (t, J=7.7 Hz, 2H), 6.87 (d, J=4.5 Hz, 1H), 6.81 (d, J=4.5 Hz, 1H), 6.36 (d, J=5.9 Hz, 1H), 5.46 (d, J=5.9 Hz, 1H), 4.79 (t, J=5.3 Hz, 1H), 4.61-4.58 (dd, J=12.2 Hz, 2.6 Hz, 1H), 4.45-4.42 (dd, J=12.3 Hz, 4.8 Hz, 1H), 4.39-4.37 (m, 1H), 4.14-4.10 (m, 1H); $^{13}C$ NMR (150 MHz, DMSO-$d_6$) δ (ppm): 166.0, 156.1, 148.4, 134.0, 129.8, 129.7, 129.2, 123.9, 117.4, 117.1, 110.8, 101.3, 81.7, 79.7, 74.5, 70.6, 63.9.

Example 17. ((2R,3S,4R,5R)-5-(4-aminopyrrolo[2,1-f][1,2,4]triazin-7-yl)-5-cyano-3,4-dihydroxytetrahydrofuran-2-yl)methyl cyclohexanecarboxylate (ATV014)

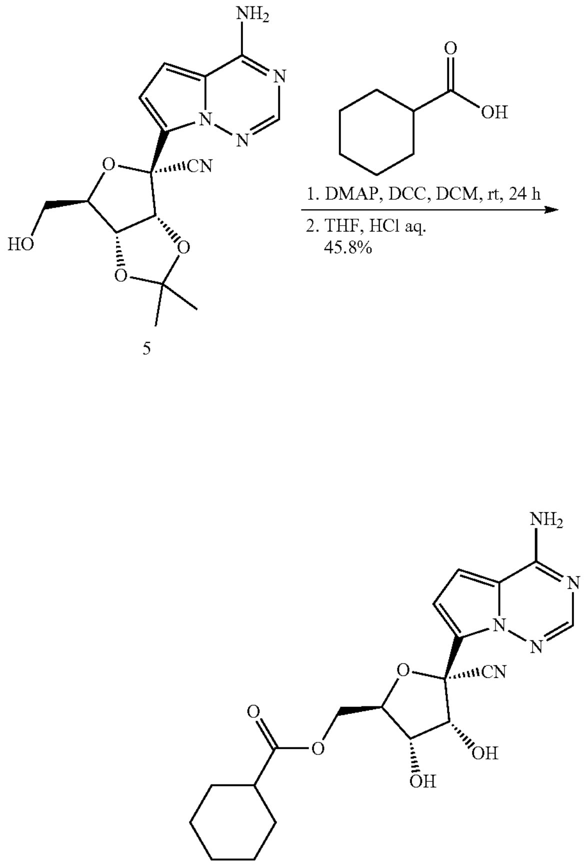

5

ATV014

Compound ATV014 was prepared by the general procedure for compound ATV006 as described in examples 8 and 9 (with cyclohexanecarboxylic acid instead of isobutyric acid for step 1). Compound ATV014 was obtained as a white solid (0.28 g, 45.8% overall yield). $^{1}H$ NMR (600 MHz, DMSO-$d_6$) δ (ppm): 7.92 (s, 1H), 7.86 (br, 1H), 6.92 (d, J=4.5 Hz, 1H), 6.81 (d, J=4.5 Hz, 1H), 6.33 (d, J=5.9 Hz, 1H), 5.38 (d, J=5.9 Hz, 1H), 4.70 (t, J=5.3 Hz, 1H), 4.32-4.29 (dd, J=12.2 Hz, 2.6 Hz, 1H), 4.24-4.21 (m, 1H), 4.16-4.13 (dd, J=12.3 Hz, 4.8 Hz, 1H), 3.98-3.95 (q, J=5.9 Hz, 1H), 2.26-2.22 (m, 1H), 1.75-1.72 (m, 2H), 1.64-1.56 (m, 3H), 1.30-1.12 (m, 5H). $^{13}C$ NMR (150 MHz, DMSO-$d_6$) δ (ppm): 175.34, 156.06, 148.4, 124.0, 117.4, 117.0, 110.7, 101.2, 81.7, 79.4, 74.5, 70.6, 63.0, 42.6, 29.0, 28.9, 25.7, 25.2, 25.1.

Example 18. ((2R,3S,4R,5R)-5-(4-aminopyrrolo[2,1-f][1,2,4]triazin-7-yl)-5-cyano-3,4-dihydroxytetrahydrofuran-2-yl)methyl cyclopentanecarboxylate (ATV015)

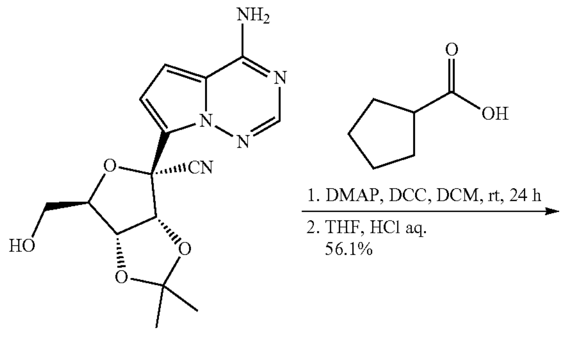

5

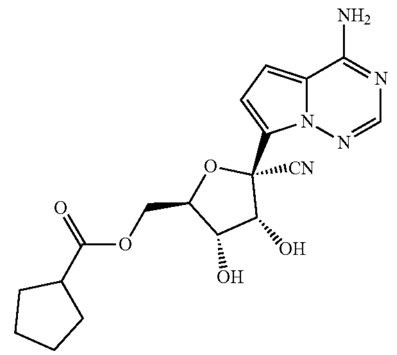

ATV015

Compound ATV015 was prepared by the general procedure for compound ATV006 as described in example 8 and 9 (with cyclopentanecarboxylic acid instead of isobutyric acid for step 1). Compound ATV015 was obtained as a white solid (0.33 g, 56.1% overall yield). $^{1}H$ NMR (600 MHz, $CD_3OD$) δ (ppm): 7.86 (s, 1H), 6.90-6.87 (q, J=4.6 Hz, 2H), 4.85-4.83 (m, 1H), 4.39-4.43 (dd, J=12.1 Hz, 3.1 Hz, 1H), 4.37-4.35 (m, 1H), 4.14 (t, J=5.7 Hz, 1H), 2.75-2.70 (m, 1H), 1.87-1.80 (m, 2H), 1.75-1.53 (m, 6H). $^{13}C$ NMR (150 MHz, $CD_3OD$) δ (ppm): 176.5, 155.9, 146.9, 124.3, 116.5, 116.2, 110.7, 101.1, 82.0, 80.0, 74.3, 70.7, 62.8, 43.5, 29.5, 29.4, 25.3.

Example 19. ((2R,3S,4R,5R)-5-(4-aminopyrrolo[2,1-f][1,2,4]triazin-7-yl)-5-cyano-3,4-dihydroxytetrahydrofuran-2-yl)methyl3,3,3-trifluoropropanoate (ATV016)

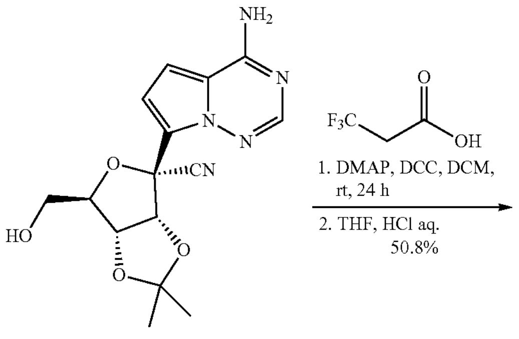

5

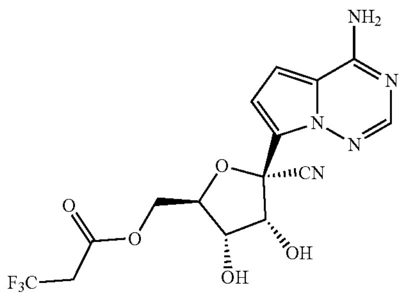

ATV016

Compound ATV016 was prepared by the general procedure for compound ATV006 as described in example 8 and 9 (with 3,3,3-trifluoropropanoic acid instead of isobutyric acid for step 1). Compound ATV016 was obtained as a white solid (0.31 g, 50.8% overall yield). $^{1}H$ NMR (600 MHz, $CD_3OD$) δ (ppm): 7.86 (s, 1H), 6.90-6.88 (q, J=4.6 Hz, 2H), 4.89 (d, J=5.3 Hz, 1H), 4.54-4.50 (m, 1H), 4.42-4.38 (m, 2H), 4.15 (t, J=5.7 Hz, 1H), 3.45-3.35 (m, 2H). $^{13}C$ NMR (150 MHz, $CD_3OD$) δ (ppm): 164.3 (J=4.0 Hz), 155.5, 146.9, 123.8 (q, J=273.6 Hz), 124.1, 116.6, 116.2, 110.8, 101.2, 81.7, 80.2, 74.0, 70.6, 64.1.

Example 20. ((2R,3S,4R,5R)-5-(4-aminopyrrolo[2,1-f][1,2,4]triazin-7-yl)-5-cyano-3,4-dihydroxytetrahydrofuran-2-yl)methyl 3-methylbutanoate (ATV017)

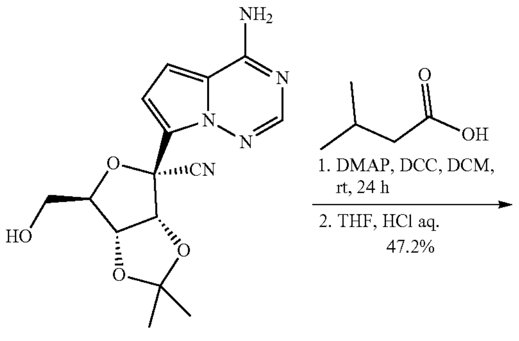

5

-continued

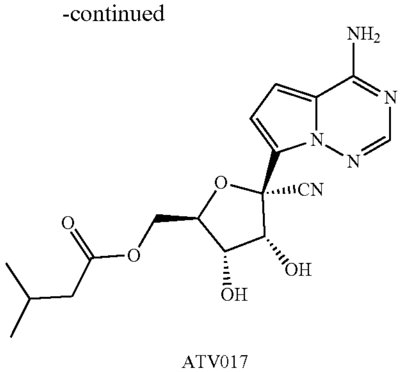

ATV017

Compound ATV017 was prepared by the general procedure for compound ATV006 as described in example 8 and 9 (with 3-methylbutanoic acid instead of isobutyric acid for step 1). Compound ATV017 was obtained as a white solid (0.27 g, 47.2% overall yield). $^1$H NMR (600 MHz, $CD_3OD$) δ (ppm): 7.86 (s, 1H), 6.90-6.88 (q, J=4.6 Hz, 2H), 4.87 (d, J=5.3 Hz, 1H), 4.43-4.40 (m, 1H), 4.39-4.35 (m, 2H), 4.31-4.29 (m, 1H), 4.14 (t, J=5.7 Hz, 1H), 2.18-2.16 (m, 2H), 2.04-1.97 (m, 1H), 0.91-0.90 (q, J=3.2 Hz, 6H). $^{13}$C NMR (150 MHz, $CD_3OD$) δ (ppm): 155.9, 146.9, 124.3, 116.5, 116.2, 110.7, 101.1, 82.0, 80.0, 74.2, 70.7, 70.6, 62.8, 62.7, 42.6, 25.4, 21.3, 21.2.

Example 21. ((2R,3S,4R,5R)-5-(4-aminopyrrolo[2,1-f][1,2,4]triazin-7-yl)-5-cyano-3,4-dihydroxytetrahydrofuran-2-yl)methyl pivalate (ATV018)

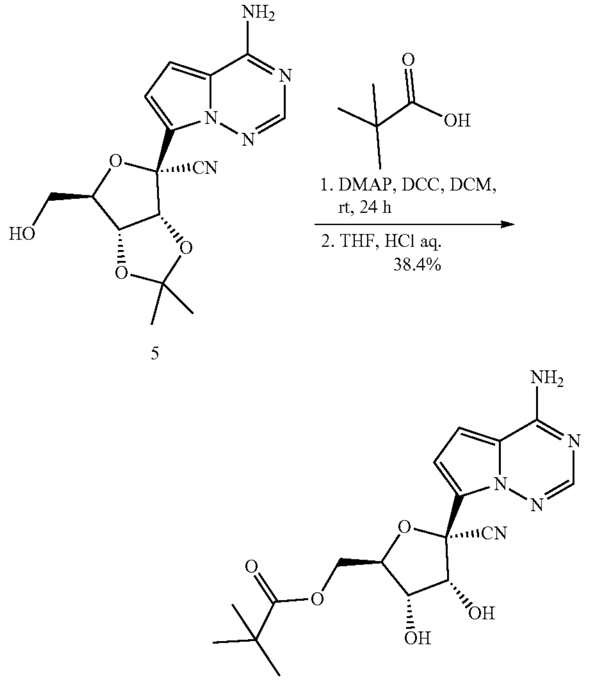

5

ATV018

Compound ATV018 was prepared by the general procedure for compound ATV006 as described in example 8 and 9 (with pivalic acid instead of isobutyric acid for step 1). Compound ATV018 was obtained as a white solid (0.22 g, 38.4% overall yield).

$^1$H NMR (600 MHz, $CD_3OD$) δ (ppm): 7.86 (s, 1H), 6.89-6.87 (q, J=4.6 Hz, 2H), 4.86 (d, J=5.3 Hz, 1H), 4.39-4.36 (m, 2H), 4.32-4.29 (m, 1H), 4.16 (t, J=5.6 Hz, 1H), 1.15 (s, 9H); $^{13}$C NMR (150 MHz, $CD_3OD$) δ (ppm): 155.9, 146.9, 124.3, 116.6, 116.2, 110.7, 101.1, 82.0, 79.9, 74.2, 70.6, 63.0, 38.5, 26.1.

Example 22. ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-D-valinate (Compound 14)

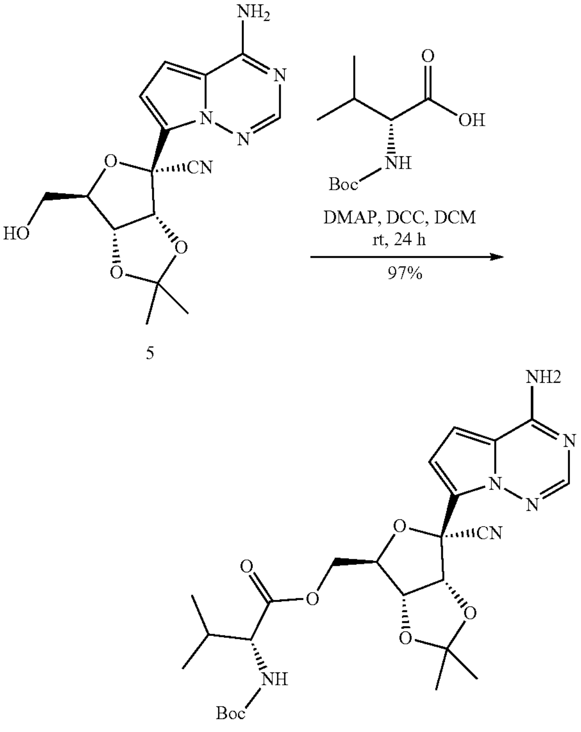

5

14

To a solution of compound 5 (1.80 g, 5.4 mmol), (tert-butoxycarbonyl)-D-valine (1.18 g, 5.4 mmol), 4-dimethylaminopyridine (66.48 mg, 0.54 mmol) in DCM (15 mL) was added dropwise to a solution of dicyclohexylcarbodiimide (1.22 g, 6 mmol) in DCM (5 mL). The mixture was stirred at rt for 24 h. The suspension was filtered and the filtrate was washed with 30 mL of saturated solution of $Na_2CO_3$ and then with 30 mL of an aqueous solution of citric acid (20% w/v). The organic layer was dried with $Na_2SO_4$ and the solvent was removed under reduced pressure. The products were purified by column chromatography (PE/EA=1:1). Compound 14 was isolated as a white solid (2.81 g, 97%). HPLC retention time: 3.293 min (eluent, water/ACN=10/90; flow rate 1 mL/min; wavelength 254 nm). $^1$H NMR (600 MHz, Methanol-$d_4$) δ 7.79 (s, 1H), 6.79 (s, 2H), 5.39 (s, 1H), 4.90 (dd, J=6.5, 3.4 Hz, 1H), 4.51 (q, J=4.1 Hz, 1H), 4.29 (dd, J=12.0, 3.8 Hz, 1H), 4.24 (dd, J=12.1, 5.2 Hz, 1H), 3.77 (d, J=6.0 Hz, 1H), 3.27-3.11 (m, 1H), 1.61 (s, 4H), 1.32 (d, J=2.5 Hz, 9H), 1.24 (s, 3H), 0.73 (dd, J=19.0, 6.8 Hz, 6H); $^{13}$C NMR (151 MHz, MeOD) δ 172.00, 156.84, 155.83, 147.06, 123.47, 116.84, 116.25, 115.65, 110.76, 101.11, 84.49, 82.89, 82.02, 81.17, 79.18, 63.54, 59.24, 53.42, 48.04, 47.91, 47.90, 47.84, 47.76, 47.62, 47.56, 47.48, 47.33, 47.19, 33.37, 30.06, 27.32, 25.35, 25.14, 24.66, 24.14, 18.14, 16.90.

Example 23. ((2R,3S,4R,5R)-5-(4-aminopyrrolo[2,1-f][1,2,4]triazin-7-yl)-5-cyano-3,4-dihydroxytetrahydrofuran-2-yl)methyl D-valinate (ATV019)

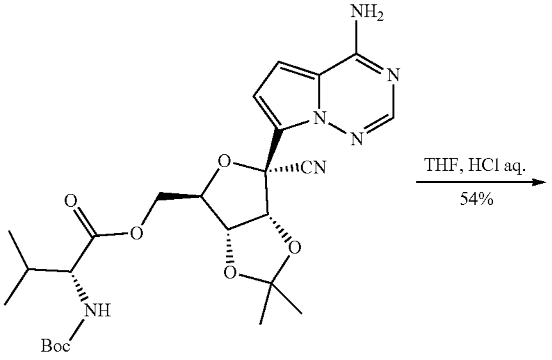

14

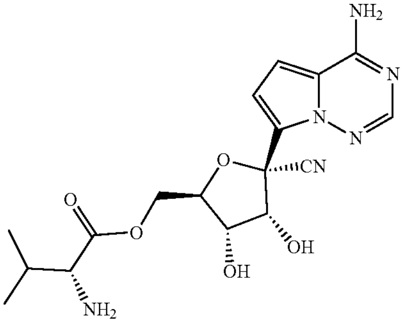

ATV019

Compound 14 (2.50 g, 4.7 mmol) was dissolved in 37% hydrochloric acid aqueous solution (3 mL) and THF (15 mL). After stirring for 6 h, pH was adjusted to 8 with $Na_2CO_3$, the solvent was removed in vacuo, and the residue was purified by silica gel column chromatography (MeOH/EA: V/V=1/20). Compound ATV019 was isolated as a white solid (0.99 g, 54%). $^1H$ NMR (400 MHz, Methanol-$d_4$) δ 7.76 (s, 1H), 6.80 (s, 2H), 4.79 (s, 1H), 4.42-4.24 (m, 3H), 4.08 (d, J=5.5 Hz, 1H), 3.23 (d, J=11.1 Hz, 1H), 1.90-1.76 (m, 1H), 0.82 (d, J=6.9 Hz, 3H), 0.74 (d, J=6.9 Hz, 3H).

Example 24. ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl (tert-butoxycarbonyl)-L-valinate (Compound 15)

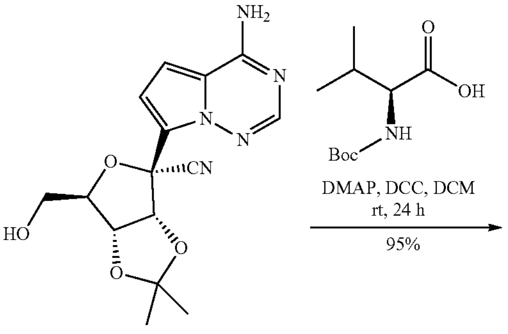

5

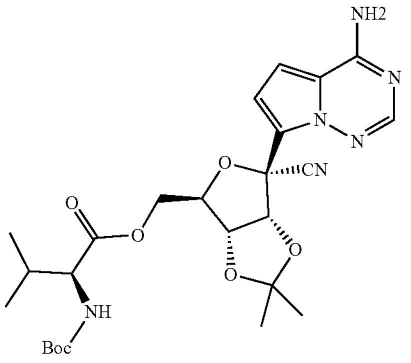

15

Compound 15 was prepared by the general procedure for compound 14 as described in example 22 with (tert-butoxycarbonyl)-L-valine instead of (tert-butoxycarbonyl)-D-valine. Compound 15 was obtained as a white solid (2.28 g, 95%).

Example 25. ((2R,3S,4R,5R)-5-(4-aminopyrrolo[2,1-f][1,2,4]triazin-7-yl)-5-cyano-3,4-dihydroxytetrahydrofuran-2-yl)methyl L-valinate (ATV020)

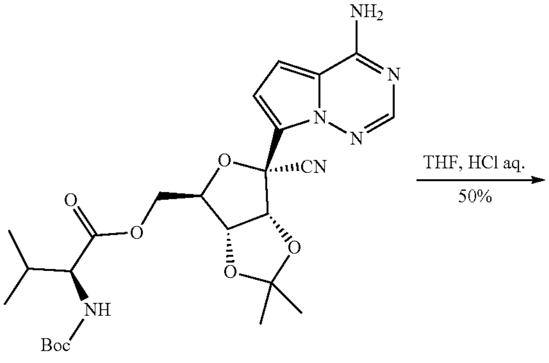

15

-continued

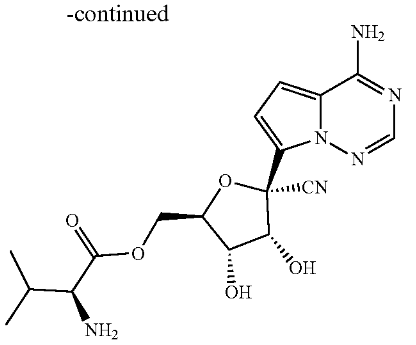

ATV020

Compound ATV020 was prepared by the general procedure for compound ATV019 as described in example 23 with compound 15 as the starting material instead of compound 14. Compound ATV020 was obtained as a white solid (0.85 g, 50%). HPLC retention time: 2.594 min (eluent, water/ACN=10/90; flow rate 0.8 mL/min; wavelength 254 nm). $^1$H NMR (600 MHz, Methanol-$d_4$) δ 7.76 (s, 1H), 6.80 (d, J=1.6 Hz, 2H), 4.81 (d, J=5.3 Hz, 1H), 4.42-4.26 (m, 3H), 4.04 (t, J=5.8 Hz, 1H), 3.25 (d, J=4.9 Hz, 1H), 1.97-1.84 (m, 1H), 0.83 (d, J=6.9 Hz, 3H), 0.79 (d, J=6.9 Hz, 3H); $^{13}$C NMR (151 MHz, MeOD) δ 173.76, 155.85, 146.93, 124.12, 116.62, 116.21, 110.86, 101.11, 81.75, 80.16, 74.04, 70.76, 63.66, 59.27, 31.62, 17.75, 16.46.

Example 26. ((2R,3S,4R,5R)-5-(4-aminopyrrolo[2,1-f][1,2,4]triazin-7-yl)-5-cyano-3,4-dihydroxytetrahydrofuran-2-yl)methyl L-phenylalaninate (ATV021)

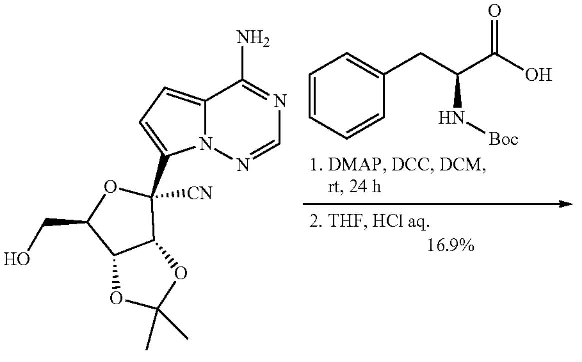

5

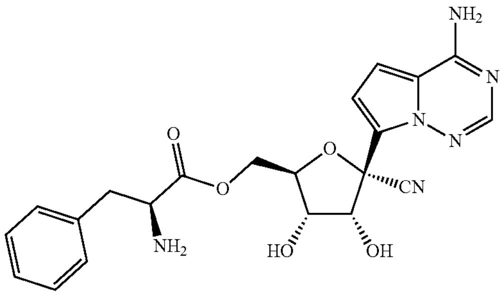

ATV021

Compound ATV021 was prepared by the general procedure for compound ATV019 as described in example 22 and 23 with (tert-butoxycarbonyl)-L-phenylalanine instead of (tert-butoxycarbonyl)-D-valine. Compound ATV021 was obtained as a white solid (0.1 g, 16.9% overall yield). $^1$H NMR (600 MHz, DMSO-$d_6$) δ (ppm): 7.96 (br, 1H), 7.95 (s, 1H), 7.87 (br, 1H), 7.21-7.13 (m, 5H), 6.93 (d, J=4.5 Hz, 1H), 6.81 (d, J=4.5 Hz, 1H), 6.33 (d, J=6.2 Hz, 1H), 5.36 (br, 1H), 4.70 (t, J=5.0 Hz, 1H), 4.28-4.24 (m, 2H), 4.19-4.16 (m, 1H), 3.88 (t, J=5.5 Hz, 1H), 3.57 (t, J=6.7 Hz, 1H), 2.84-2.73 (m, 2H), 1.85 (br, 2H); $^{13}$C NMR (150 MHz, DMSO-$d_6$) δ (ppm): 174.5, 155.4, 147.8, 137.5, 129.0, 127.9, 126.1, 123.4, 116.8, 116.4, 110.1, 100.7, 81.1, 78.9, 73.8, 70.0, 63.1, 55.6, 40.4.

Example 27. ((2R,3S,4R,5R)-5-(4-aminopyrrolo[2,1-f][1,2,4]triazin-7-yl)-5-cyano-3,4-dihydroxytetrahydrofuran-2-yl)methyl D-phenylalaninate (ATV022)

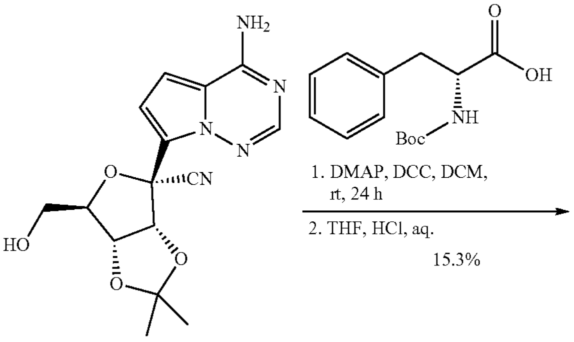

5

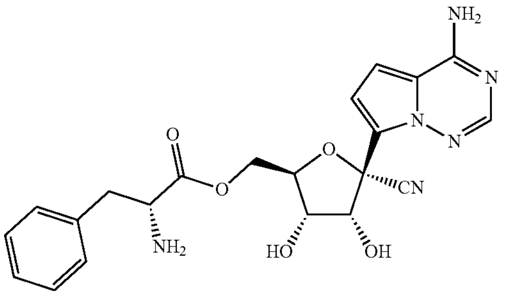

ATV022

Compound ATV022 was prepared by the general procedure for compound ATV019 as described in example 22 and 23 with (tert-butoxycarbonyl)-D-phenylalanine instead of (tert-butoxycarbonyl)-D-valine. Compound ATV022 was obtained as a white solid (0.1 g, 15.3% overall yield). $^1$H NMR (600 MHz, DMSO-$d_6$) δ (ppm): 7.92 (s, 1H), 7.85 (br, 1H), 7.25-7.14 (m, 5H), 6.90 (d, J=4.5 Hz, 1H), 6.80 (d, J=4.5 Hz, 1H), 6.33 (d, J=5.9 Hz, 1H), 5.39 (d, J=5.6 Hz, 1H), 4.71 (t, J=5.3 Hz, 1H), 4.25-4.17 (m, 3H), 3.95-3.94 (m, 1H), 3.56 (t, J=6.7 Hz, 1H), 2.86-2.71 (m, 2H), 1.75 (br, 2H); $^{13}$C NMR (150 MHz, DMSO-$d_6$) δ (ppm): 175.2, 156.1, 148.4, 138.2, 129.7, 128.6, 126.8, 124.0, 117.4, 117.1, 110.8, 101.3, 81.7, 79.5, 74.5, 70.7, 63.9, 56.1.

Example 28. ((2R,3S,4R,5R)-5-(4-aminopyrrolo[2,1-f][1,2,4]triazin-7-yl)-5-cyano-3,4-dihydroxytetrahydrofuran-2-yl)methyl (2S)-2-amino-3-methylpentanoate (ATV023)

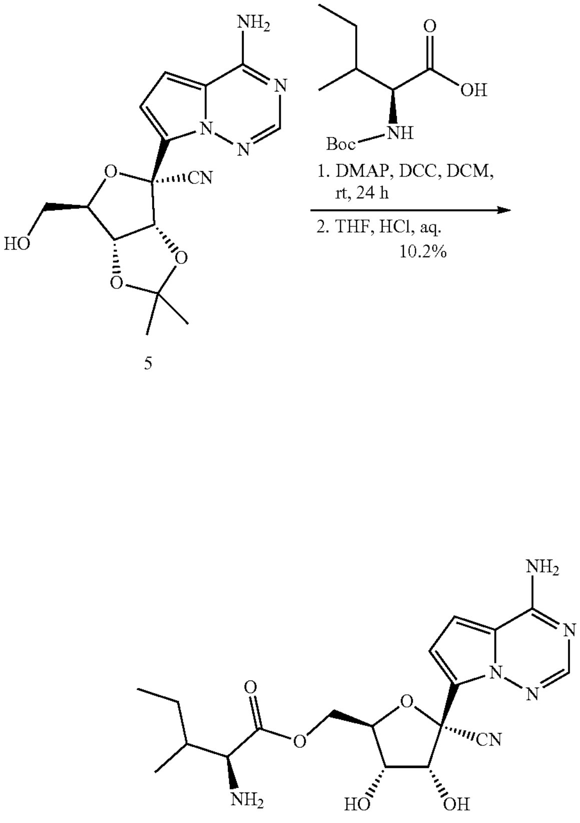

5

ATV023

Compound ATV023 was prepared by the general procedure for compound ATV019 as described in example 22 and 23 with (2S)-2-((tert-butoxycarbonyl)amino)-3-methylpentanoic acid instead of (tert-butoxycarbonyl)-D-valine. Compound ATV023 was obtained as a white solid (0.06 g, 10.2% overall yield). $^{1}H$ NMR (600 MHz, DMSO-$d_6$) δ (ppm): 7.95 (br, 1H), 7.92 (s, 1H), 7.87 (br, 1H), 6.92 (d, J=5.8 Hz, 1H), 6.83 (d, J=5.8 Hz, 1H), 6.35 (br, 1H), 5.40 (br, 1H), 4.73 (d, J=4.6 Hz, 1H), 4.29-4.24 (m, 3H), 3.96 (t, J=5.0 Hz, 1H), 3.18 (d, J=4.2 Hz, 1H), 1.53-1.51 (m, 1H), 1.39-1.32 (m, 1H), 1.11-1.04 (m, 1H), 0.80-0.74 (m, 6H); $^{13}C$ NMR (150 MHz, DMSO-$d_6$) δ (ppm): 175.6, 156.1, 148.4, 124.0, 117.4, 117.0, 110.8, 101.3, 81.6, 79.5, 74.5, 70.7, 63.5, 59.1, 39.1, 24.6, 16.0, 11.8.

Example 29. ((2R,3S,4R,5R)-5-(4-aminopyrrolo[2,1-f][1,2,4]triazin-7-yl)-5-cyano-3,4-dihydroxytetrahydrofuran-2-yl)methyl (2R)-2-amino-3-methylpentanoate (ATV024)

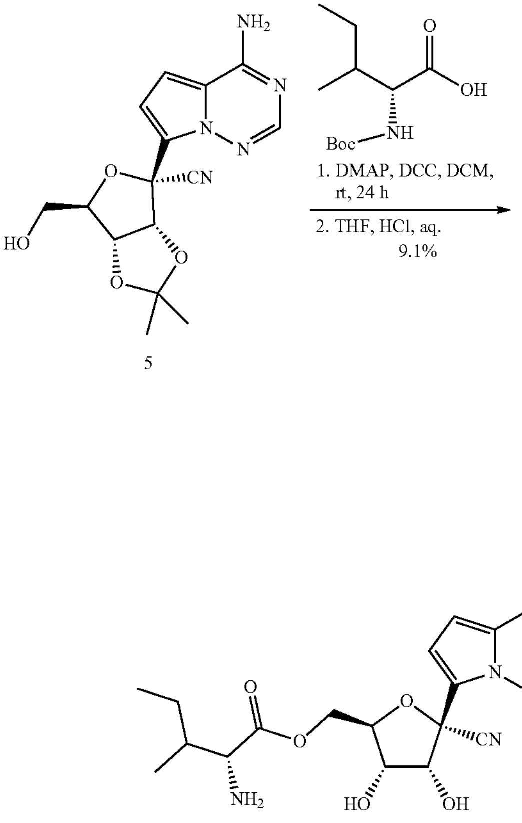

5

ATV024

Compound ATV024 was prepared by the general procedure for compound ATV019 as described in example 22 and 23 with (2R)-2-((tert-butoxycarbonyl)amino)-3-methylpentanoic acid instead of (tert-butoxycarbonyl)-D-valine. Compound ATV024 was obtained as a white solid (0.06 g, 9.1% overall yield). $^{1}H$ NMR (600 MHz, DMSO-$d_6$) δ (ppm): 7.92 (s, 1H), 7.86 (br, 2H), 6.92 (d, J=5.8 Hz, 1H), 6.83 (d, J=5.8 Hz, 1H), 6.33 (d, J=4.7 Hz, 1H), 5.39 (br, 1H), 4.71 (br, 1H), 4.30-4.19 (m, 3H), 3.97 (t, J=5.1 Hz, 1H), 3.15 (d, J=5.3 Hz, 1H), 1.53-1.50 (m, 1H), 1.39-1.34 (m, 1H), 1.11-1.04 (m, 1H), 0.80-0.75 (m, 6H); $^{13}C$ NMR (150 MHz, DMSO-$d_6$, ATV109) δ (ppm): 175.6, 156.1, 148.4, 124.0, 117.4, 117.1, 110.8, 101.3, 81.7, 79.5, 74.5, 70.8, 63.8, 59.1, 39.0, 24.6, 16.1, 11.8.

Example 30. ((2R,3S,4R,5R)-5-(4-amino-5-fluoro-pyrrolo[2,1-f][1,2,4]triazin-7-yl)-5-cyano-3,4-dihydroxytetrahydrofuran-2-yl)methyl isobutyrate (ATV025)

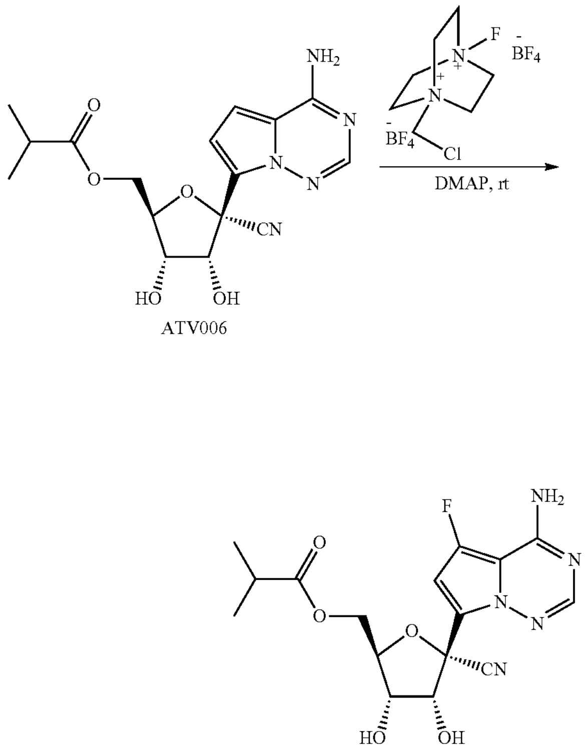

ATV006

ATV025

To a solution of compound ATV006 (1 g, 2.77 mmol) and DMAP (0.34 g, 2.77 mmol) in a solvent system of ACN and water (20 mL, v/v=9:1) was added Selectfluor (N-Fluoro-N'-(chloromethyl)triethylenediamine bis(tetrafluoroborate), 1.4 g, 5.5 mmol). The mixture was stirred at rt. After completion, the solvent was removed under reduced pressure, and the residue was quenched with EA (100 mL). The solution was washed with 30 mL of a saturated solution of $Na_2CO_3$ and then with 30 mL of brine. The organic layer was dried with $Na_2SO_4$, and the solvent was removed under reduced pressure to obtain a brown oil. The crude product was purified by column chromatography (DCM/MeOH=50/1) to give compound ATV025 as an off-white solid (100 mg, 9.5%). $^1H$ NMR (600 MHz, $CD_3OD$) δ (ppm): 7.79 (s, 1H), 6.65 (s, 1H), 4.79 (d, J=5.0 Hz, 1H), 4.40-4.30 (m, 3H), 4.09 (t, J=5.6 Hz, 1H), 2.59-2.54 (m, 1H), 1.14-1.13 (m, 6H); $^{13}C$ NMR (150 MHz, $CD_3OD$) δ (ppm): 176.9, 154.5, 147.6, 144.0, 142.3, 121.0, 115.7, 102.7, 102.5, 97.0, 96.9, 81.9, 79.6, 74.5, 70.5, 62.7, 33.7, 17.9, 17.8; $^{19}F$ NMR (600 MHz, $CD_3OD$) δ (ppm): −160.8.

Example 31. ((3aR,4R,6R,6aR)-6-(4-amino-5-iodopyrrolo[2,1-f][1,2,4]triazin-7-yl)-6-cyano-2,2-dimethyltetrahydrofuro[3,4-d][1,3]dioxol-4-yl) methyl isobutyrate (Compound 16)

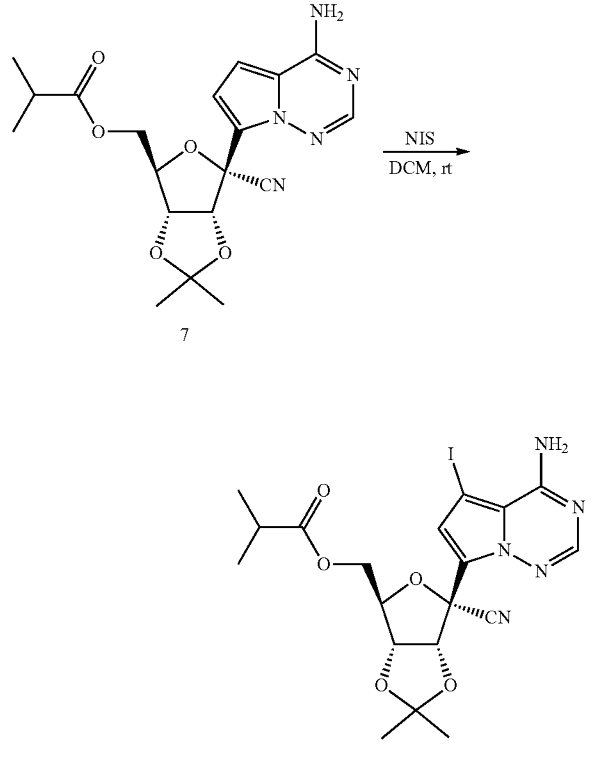

7

16

To a solution of compound 7 (0.5 g, 1.2 mmol) in DCM (10 mL) was added N-Iodosuccinimide (0.28 g, 1.2 mmol). The mixture was stirred at rt. After completion, the solvent was removed under reduced pressure, and the residue was purified by column chromatography (EA/PE=1/2) to give compound 16 as a red solid (350 mg, 53.3%).

Example 32. ((3aR,4R,6R,6aR)-6-(4-aminopyrrolo[2,1-f][1,2,4]triazin-7-yl-5-d)-6-cyano-2,2-dimethyltetrahydrofuro[3,4-d][1,3]dioxol-4-yl)methyl isobutyrate (Compound 17)

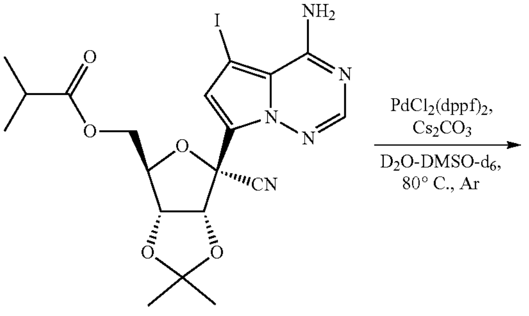

16

-continued

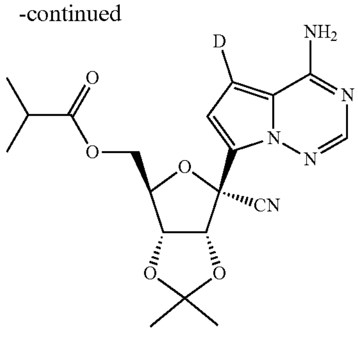

17

To a solution of compound 16 (200 mg, 0.38 mmol) and cesium carbonate (247 mg, 0.76 mmol) in $D_2O$-DMSO-$d_6$ (10 mL, v/v=1:9) was charged with $PdCl_2(dppf)_2$ (32 mg, 0.04 mmol) under argon. The mixture was stirred and heated up to 80° C. After 10 h, the reaction was complete, as monitored by TLC. The reaction was cooled to rt and slowly poured into water (10 mL). The mixture was extracted with EA (30 mL×2). The combined organic layers were washed with water and were concentrated in vacuo to provide a red oil. The crude product was purified by column chromatography (EA/PE=1/2) to give 17 as a pale-red oil (68 mg, 44.7%).

Example 33. ((2R,3S,4R,5R)-5-(4-aminopyrrolo[2,1-f][1,2,4]triazin-7-yl-5-d)-5-cyano-3,4-dihydroxytetrahydrofuran-2-yl)methyl isobutyrate (ATV026)

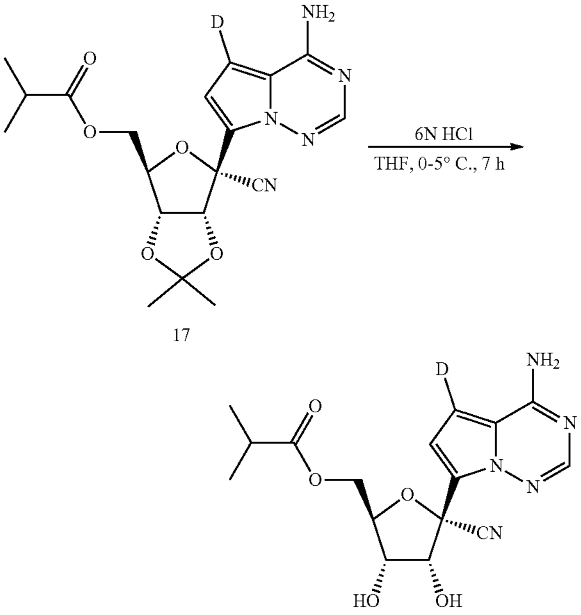

17

ATV026

Compound 17 (68 mg, 0.17 mmol) was dissolved in 6 N hydrochloric acid aqueous solution (1 mL) and THF (1.5 mL). After stirring for 7 h, pH was adjusted to 8 with $Na_2CO_3$, and the solvent was removed in vacuo. The residue was purified by silica gel column chromatography (PE/EA: V/V=1/1). Compound ATV026 was isolated as an off-white solid (38 mg, 61.7% yield). $^1$H NMR (400 MHz, DMSO-$d_6$) δ (ppm): 7.97 (s, 1H), 7.10 (s 1H), 6.51 (br, 2H), 5.34 (d, J=6.7 Hz, 1H), 4.88-4.85 (dd, J=6.7 Hz, 4.2 Hz, 1H), 4.61-4.57 (q, J=4.3 Hz, 1H), 4.43-4.39 (dd, J=12.0 Hz, 4.2 Hz, 1H), 4.28-4.23 (dd, J=12.0 Hz, 5.5 Hz, 1H), 2.59-2.49 (m, 1H), 1.16 (q, J=4.0 Hz, 6H).

Example 34. Inhibitory Effect of Compounds Against SARS-CoV Replicon in HEK293T Cells HEK293T cells were seeded in a 24-well plate. When the cells density was about 40-50%, cells were transfected with SARS-CoV replicon (250 ng). After 6-8 h, the cells are transfected, the supernatant was discarded and replaced with fresh DMEM medium, followed by adding each compound (described in Table 3) to the media with the final concentration of 50 μM, 10 μM, 5 μM, 2 μM, 1 μM, 0.1 μM or 0.01 μM. After 60 h, the supernatant was discarded, and the cell RNAs were isolated with TRIzol reagent. The mRNAs were reverse transcribed into cDNA by PrimeScript RT reagent Kit. The cDNA was amplified by a fast two-step amplification program using SYBR Green Fast qPCR MasterMix to detect subgenome of SARS-CoV N. GAPDH was used to normalize the input samples via the ΔΔCt method. We calculated the inhibitory effects with different concentrations of tested drugs on virus replication and calculated their $IC_{50}$ value. The inhibitory effects of various compounds against SARS-CoV replicons in HEK293T cells are shown in Table 3.

TABLE 3

The inhibitory effects of different compounds against SARS-CoV replicons in HEK293T cells.

| Compound | Inhibition % (10 μM) | $IC_{50}$ (μM) |
|---|---|---|
| GS-441524 | 99.79 | 1.1 |
| ATV001 | 66.75 | NA |
| ATV002 | 60.97 | NA |
| ATV003 | 98.8 | 0.91 |
| ATV004 | 91.76* | NA |
| Intermediate 5 of RDV | 75.94 | NA |
| ATV019 | 98.56 | 0.79 |
| ATV006 | 99.2 | 0.57 |
| ATV020 | 99.21 | 1.3 |
| ATV005 | 73.3 | NA |

Notes
*The test concentration of 5 μM;
NA: data not available

Conclusion: These compounds inhibited the replication of SARS-CoV to varying degrees in HEK293T cells. Among them, the activity of ATV006 is twice that of compound GS-441524, and the activity is significantly improved.

Figure 3:
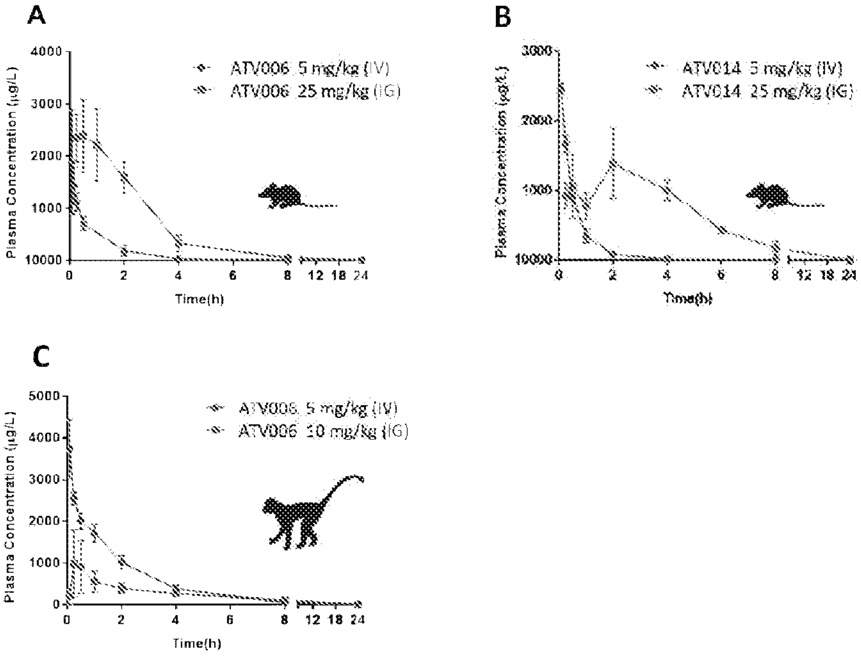
FIG. 3A shows the time-concentration curve of compound ATV006 in a PK study in Sprague-Dawley rats.
FIG. 3B shows the time-concentration curve of compound ATV014 in a PK study in Sprague-Dawley rats.
FIG. 3C shows the time-concentration curve of compound ATV006 in a PK study in and cynomolgus monkeys.

Example 35. Inhibitory Effect of Compounds Against SARS-CoV-2 Replicon in HEK293T Cells The following compound GS-441524, ATV001, ATV002, ATV003, ATV004, ATV005, ATV006, ATV007, ATV008, ATV009, ATV010, ATV011, ATV012, ATV013, ATV014, ATV015, ATV016, ATV017, ATV018, ATV019, ATV020, ATV021, ATV022, ATV023, ATV024, ATV025 or Intermediate 5 of RDV are used as the test compounds, and the operation procedures are described below:

HEK293T cells were seeded in a 24-well plate. When the cells density was about 40-50%, cells were transfected with SARS-CoV-2 replicon (250 ng) and TK (10 ng). After 6-8 h, the cells are transfected, the supernatant was discarded and replaced with fresh DMEM medium, followed by adding each compound (described in Table 1) to the media with the final concentration of 50 μM, 10 μM, 5 μM, 2 μM, 1 μM, 0.1 μM or 0.01 μM. After 60 h, cells were lysed in 200 μL Passive Lysis Buffer (PLB). Each lysate (20 μL) was transferred into 96-well white plate and then mixed with 20 μL Luciferase Assay Reagent II, followed by 20 μL of Stop & Glo solution. The luminescence values of the two-step reaction were recorded using a luminescence detector in Synergy H1 Hybrid Multi-Mode Reader. We calculated the inhibitory effects with different concentrations of tested drugs on virus replication and calculated their $IC_{50}$ value. The inhibitory effects of different compounds against SARS-CoV-2 replicons in HEK293T cells are shown in FIG. 3 and Table 4.

TABLE 4

The inhibitory effects of different compounds against SARS-CoV-2 replicons in HEK293T cells.

| Compound | Inhibition % (10 μM) | $IC_{50}$ (μM) |
|---|---|---|
| GS-441524 | 99.79 | 0.95 |
| ATV001 | NA | >50 |
| ATV002 | NA | >50 |
| ATV003 | 97.56 | 0.83 |
| ATV004 | 97.53 | 0.68 |
| ATV005 | NA | >50 |
| ATV006 | 98.58 | 0.51 |
| ATV007 | 91.57 | NA |
| ATV008 | 98.15 | NA |
| ATV009 | 98.78 | 0.22 |
| ATV010 | 98.99 | 0.32 |
| ATV011 | 98.91 | 0.32 |
| ATV012 | 97.08 | NA |
| ATV013 | 97.67 | 0.50 |
| ATV014 | 98.23 | 0.26 |
| ATV015 | 97.87 | 0.71 |
| ATV016 | 97.23 | 0.83 |
| ATV017 | 97.21 | 0.43 |
| ATV018 | 97.49 | 0.42 |
| ATV019 | 97.17 | 0.97 |
| ATV020 | 99.21 | 2.35 |
| ATV021 | 0 | NA |
| ATV022 | 0 | NA |
| ATV023 | 98.66 | 0.95 |
| ATV024 | 99.10 | 0.86 |
| ATV025 | 97.79 | 0.89 |
| Intermediate 5 of RDV | NA | >50 |

Notes
NA: data not available

Conclusion: These compounds inhibited the replication of SARS-CoV-2 to varying degrees in HEK293T cells. Among them, the antiviral activity of ATV001 and ATV002 is significantly lower than that of GS-441524, while the activity of ATV004, ATV009, ATV010, ATV011, and other compounds are improved. This indicates that the antiviral activity of this series of a compound is not obvious, and the simple ester mono-substitution of the hydroxyl group at the $C_5$ position can significantly increase the antiviral activity.

Figure 2:
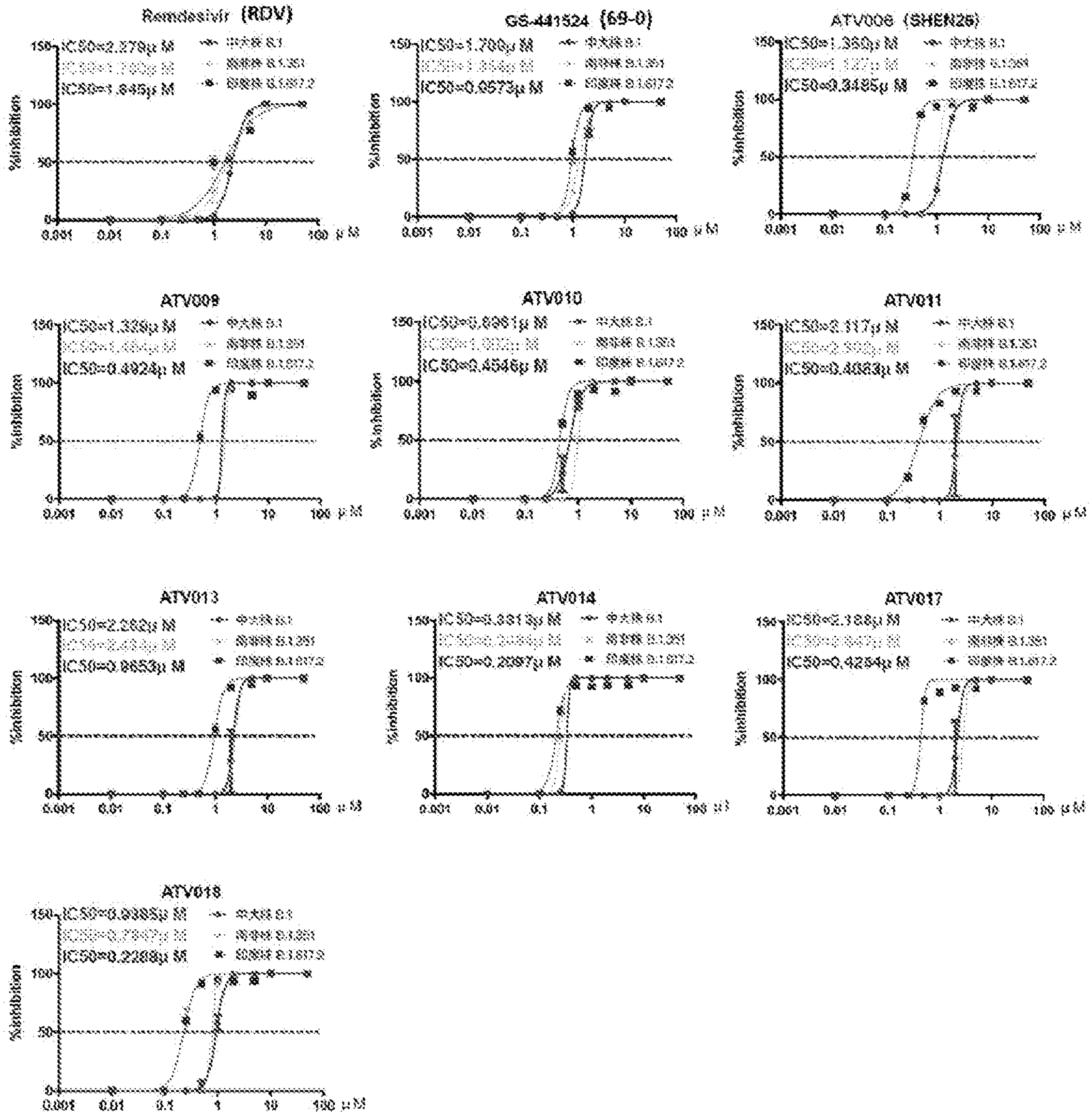
FIG. 2 shows the dose-dependent anti-SARS-CoV-2 effect of compounds including RDV, GS-441524, ATV006, ATV009, ATV010, ATV011, ATV013, ATV014, ATV017, and ATV018 against SARS-CoV-2 and its two variants (B.1, B.1.351 and B.1.617.2) in Vero-E6 cells.

Example 36. Inhibitory Effect of Compounds Against SARS-CoV-2 in Vero-E6 Cells The following compound RDV, GS-441524, ATV006, ATV009, ATV010, ATV011, ATV013, ATV014, ATV017, ATV018 are used as the test compounds, and the operation procedures are described below:

Vero-E6 cells were seeded in a 48-well plate. When the cells density was about 70-80%, the supernatant was discarded and replaced with fresh DMEM medium, followed by adding each compound to the media with the final concentration of 50 μM, M, 5 μM, 2 μM, 1 μM, 0.5 M, 0.25 M, 0.1 μM or 0.01 μM. Cells were infected with SARS-CoV-2 and its two variants (B.1, B.1.351 and B.1.617.2) at a multiplicity of infection (MOI) of 0.05. Antiviral activities were evaluated by quantitative real-time polymerase chain reaction (qRT-PCR) quantification of a viral copy number in the supernatant 48 h post infection. We calculated the inhibitory effects with different concentrations of tested drugs on virus replication and calculated their $IC_{50}$ value. The $IC_{50}$ of different compounds against SARS-CoV-2 in Vero-E6 cells are shown in FIG. 2 and Table 5.

TABLE 5

The inhibitory effects of different compounds against SARS-CoV-2 in Vero-E6 cells.

| Compound | B.1 $IC_{50}$ (μM) | B.1.351 $IC_{50}$ (μM) | B.1.617.2 $IC_{50}$ (μM) |
|---|---|---|---|
| GS-441524 | 2.279 | 1.780 | 1.645 |
| RDV | 1.709 | 1.354 | 0.9573 |
| ATV006 | 1.360 | 1.127 | 0.3485 |
| ATV009 | 1.329 | 1.383 | 0.4924 |
| ATV010 | 0.6961 | 1.002 | 0.4546 |
| ATV011 | 2.117 | 2.302 | 0.4083 |
| ATV013 | 2.262 | 2.434 | 0.9653 |
| ATV014 | 0.3313 | 0.2484 | 0.2097 |
| ATV017 | 2.188 | 2.847 | 0.4284 |
| ATV018 | 0.9385 | 0.7847 | 0.2288 |

Example 37. PK Study of Compound ATV006, ATV014 and GS441526 in Rat

Rat: 16 SPF-grade male SD rats, weighing 180-220 g.

Grouping: SD rats were divided into 4 groups, 4 in each group (3 in each group for ATV014). The information of each group was described below:

ATV006 (IV): rat intravenously received ATV006 at a dose of 5 mg/kg;

ATV006 (IG): rat intragastrically received ATV006 at a dose of 25 mg/kg;

ATV014 (IV): rat intravenously received ATV006 at a dose of 5 mg/kg;

ATV014 (IG): rat intragastrically received ATV006 at a dose of 25 mg/kg;

GS-441524 (IV): rat intravenously received GS-441524 at a dose of 5 mg/kg;

GS-441524 (IG): rat intragastrically received GS-441524 at a dose of 25 mg/kg.

Compound AVT006, ATV014 or GS-441524 was administered intragastrically or intravenously. After administration, 0.3 mL of the jugular blood was taken at 0.083, 0.16 0.25, 0.5, 2, 3, 4, 8, 24 and 48 h for the iv group, and 0.25, 0.5, 1, 2, 3.0, 4, 6, 8, 24 and 48 h for the ig group, respectively. Samples were centrifuged under 4000 rpm/min for 10 min at 4° C. The supernatants (plasma) were collected and stored at −20° C. for future analysis. For plasma drug concentration analysis, an aliquot of 50 μL each plasma sample was treated with 100 μL of 90% methanol-water solution and 600 μL of 50% acetonitrile-methanol solution. The samples were centrifuged under 1200 rpm for 10 min and filtered through 0.2 μm membrane filters. The drug concentration in each sample was tested by HPLC/MS. Analytes were separated on a InertSustain AQ-C18HP column (3.0 mmx 50 mm, 3.0 μm, GL) using Waters UPLC/XEVO TQ-S. The pharmacokinetic parameters were calculated using DAS (Drug and Statistics) 3.0 software. The time-concentration curve was plotted using GraphPad Prism 6 software. The results were shown in Table 6-8 and FIG. 3A-B.

TABLE 6

PK parameter of ATV006 in SD rats (analyzed GS-441524, average ± SD, n = 4)

| PK parameter | | ATV006 | ATV006 |
|---|---|---|---|
| parameter | unit | (IV) | (IG) |
| $AUC_{(0-t)}$ | μg/L*h | 1843.1 ± 463.1 | 7334.9 ± 1428.1 |
| $AUC_{(0-\infty)}$ | μg/L*h | 1867.2 ± 469.1 | 7569.2 ± 1230.6 |
| $t_{1/2}$ | h | 10.25 ± 3.15 | 16.18 ± 17.65 |
| $T_{max}$ | h | 0.08 ± 0.0 | 0.38 ± 0.14 |
| $C_{max}$ | ng/mL | 1887.8 ± 1003.1 | 2715.4 ± 240.3 |
| F | % | / | 79.59 ± 15.5 |

TABLE 7

PK parameter of ATV014 in SD rats (analyzed GS-441524, average ± SD, n = 3)

| PK parameter | | ATV006 | ATV006 |
|---|---|---|---|
| parameter | unit | (IV) | (IG) |
| $AUC_{(0-t)}$ | μg/L*h | 3015.06 ± 156.96 | 7398.72 ± 78.07 |
| $AUC_{(0-\infty)}$ | μg/L*h | 3036.30 ± 158.66 | 7470.18 ± 189.98 |
| $t_{1/2}$ | h | 1.65 ± 0.92 | 1.94 ± 0.65 |
| $T_{max}$ | h | 0.08 ± 0.0 | 2.67 ± 1.15 |
| $C_{max}$ | ng/mL | 2466.44 ± 73.54 | 1427.20 ± 438.46 |
| F | % | / | 49.08 ± .52 |

TABLE 8

PK parameter of GS-441524 in SD rats (analyzed GS-441524, average ± SD, n = 4)

| PK parameter | | GS-441524 | GS-441524 |
|---|---|---|---|
| parameter | unit | (IV) | (IG) |
| $AUC_{(0-t)}$ | μg/L*h | 3443.5 ± 460.6 | 3896 ± 1795.7 |
| $AUC_{(0-\infty)}$ | μg/L*h | 3478.8 ± 455.5 | 3913.5 ± 1778.2 |
| $t_{1/2}$ | h | 12.69 ± 7.34 | 6.85 ± 6.76 |
| $T_{max}$ | h | 0.08 ± 0.0 | 0.75 ± 0.29 |
| $C_{max}$ | ng/mL | 2384.6 ± 282.4 | 1071.7 ± 147.2 |
| F | % | / | 22.63 ± 10.43 |

Conclusion: As shown in Table 6-8 and FIG. 3A-B, the bioavailability of ATV006 (IG), ATV014 (IG), GS-441524 (IG) in rats was 79.59% (calculated by its metabolite GS-441524), 49.08% (calculated by its metabolite GS-441524), and 22.63%, respectively. These data indicated the bioavailability of ATV006 and ATV014 was significantly improved as compared to GS-441524.

Example 38. PK Study of Compound ATV006 in Cynomolgus Monkeys

Three male cynomolgus monkeys weighing 3-5 kg were used for the pharmacokinetic study. Compound AVT006 was administered intragastrically with the dose of 10 mg/kg on day 1. After administration, the blood samples for plasma were collected from a jugular vein from each monkey over 48 hours. The plasma samples (1 mL) were obtained at predose, and 0.083, 0.25, 0.5, 1, 2, 4, 8, 24 and 48 h postdose. After recovery for three days, compound AVT006 was administered intravenously with a dose of 5 mg/kg at day 5. The blood samples for plasma were collected from a jugular vein from each monkey over 48 hours. 1 mL plasma samples were obtained at predose, and 0.083, 0.25, 0.5, 1, 2, 4, 8, 24 and 48 h postdose. Samples were treated with anticoagulant EDTA-$K_2$ and centrifuged under 2000 g for 10 min at 4° C. The supernatants (plasma) were collected and stored at −65° C. for future analysis. The drug concentration in each sample was tested by Watson LIMS 7.5 SP1 HPLC/MS. The pharmacokinetic parameters were calculated using WinNonlin 6.3 software. The time-concentration curve was plotted using GraphPad Prism 6 software, and the data was presented in Table 9 and FIG. 3C.

TABLE 9

PK parameter of compound ATV006 in cynomolgus monkeys (analyzed both ATV006 and GS-441524, average ± SD, n = 3)

| PK parameter | | ATV006 (IV, analyzed | ATV006 (IV, analyzed | ATV006 (IG, analyzed |
|---|---|---|---|---|
| parameter | unit | GS-441524) | ATV006) | GS-441524) |
| $AUC_{(0-t)}$ | μg/L*h | 5960 ± 490 | 19.4 ± 5.35 | 3560 ± 245 |
| $AUC_{(0-\infty)}$ | μg/L*h | 6050 ± 562 | 19.6 ± 5.43 | 3620 ± 288 |
| $t_{1/2}$ | h | 1.78 ± 0.597 | 0.0691 ± 0.00743 | 4.08 ± 0.939 |
| $T_{max}$ | h | 0.0833 ± 0.0 | 0.0833 ± 0.0 | 1.5 ± 2.2 |
| $C_{max}$ | ng/mL | 3730 ± 7091 | 132 ± 37.4 | 1080 ± 651 |
| F | % | / | / | 30.08 ± 0.041 |

Conclusion: As shown in FIG. 3C and Table 9, compound ATV006 was quickly metabolized into the active metabolite GS-441524. The bioavailability of compound ATV006 was 30%, as analyzed by GS-441524. The bioavailability of GS-441524 was 8.3%, as reported by NIH OpenData Portal. In conclusion, compound ATV006 exhibited a significantly improved bioavailability in both rat and non-human primates.

Example 39: In Vivo Efficacy of Compound ATV006 in Murine Hepatitis Virus (MHV-A59)

Mice: SPF-grade male BALB/c mice, 100, weighing 18-22 g.

Operation: The experimental mice were infected with MHV-A59 nasal drops and randomly divided into ten groups (n=10 each). The information of each group is described as follows:

Group A: Control group
Group B1: ATV006 50 mg/kg (IG)
Group B2: ATV006 20 mg/kg (IG)
Group B3: ATV006 10 mg/kg (IG)
Group B4: ATV006 5 mg/kg (IG)
Group B5: ATV006 2 mg/kg (IG)
Group B6: RDV 20 mg/kg (IG)
Group B7: GS-441524 50 mg/kg (IG)
Group C: Not infected
Group D: Not infected, ATV006 50 mg/kg (IG)

Figure 4:
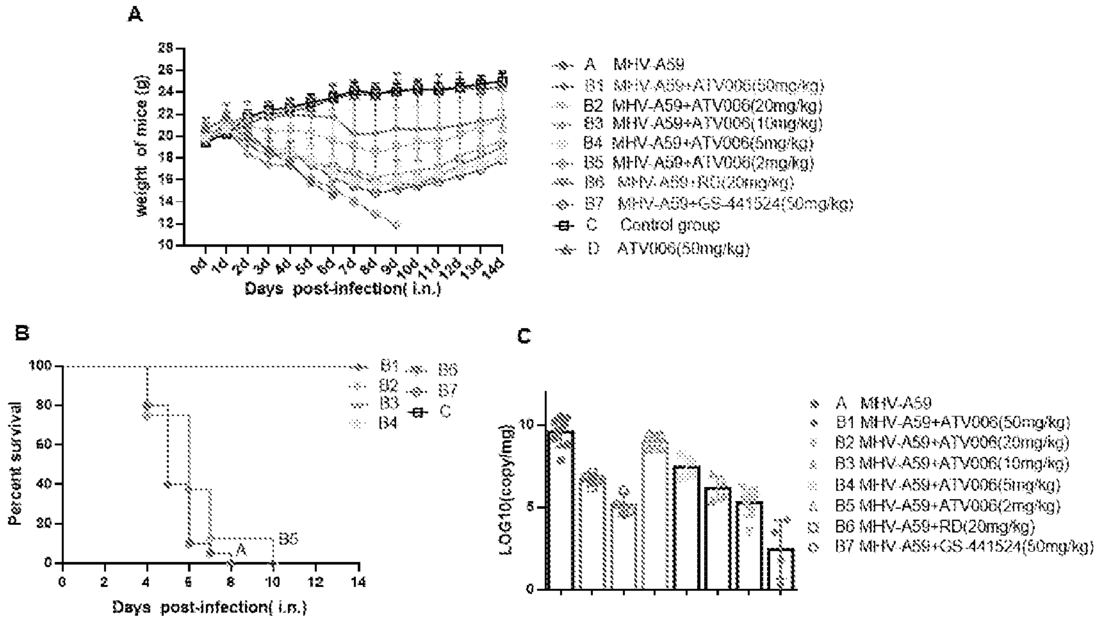
FIG. 4A shows the efficacy results of compound ATV006 against mouse hepatitis virus (MHV-A59) in vivo by the bodyweight change of mice in 10 groups.
FIG. 4B shows the efficacy results of compound ATV006 against mouse hepatitis virus (MHV-A59) in vivo by the survival status.
FIG. 4C shows the efficacy results of compound ATV006 against mouse hepatitis virus (MHV-A59) in vivo by the viral titer of the liver 72 hours after viral infection.

The mice were monitored daily for disease symptoms, including body weight, clinical symptoms, and death, for 14 days. Record the body weight changes of mice in each treatment group after virus infection (FIG. 4A) and survival curves (FIG. 4B). The fluorescence quantitative PCR method was used to determine the virus titer in mouse liver 72 hours after virus infection (FIG. 4C).

Conclusion: It can be seen from the results in FIG. 3 that the compound ATV006 has better antiviral activity in vivo, as compared with GS-441524 and RDV. The reasons are as follows:

Compound ATV006 (except 2 mg/kg) can avoid the death and weight loss of mice at low doses, and the dose required is less than that of GS-441524 (FIGS. 4A and 4B).

Compound ATV006 can significantly inhibit the replication of the virus in the liver (FIG. 4C).

The mice treated with 2 mg/kg of compound ATV006 (Group B5) began to die on day 4 after infection. By day 10 after infection, the mortality rate was 100%, and the median death rate was 6 days. Compared with the virus model control group (group A), the mortality rate was significantly different (p=0.0291). This result shows that compound ATV006 can still exhibit a positive effect in prolonging the survival time of animals at an ultra-low dose of 2 mg/kg.

Example 40: In Vivo Efficacy of Compound ATV006 in SARS-CoV-2

Mice: SPF-grade male C57BL/6 hACE2 humanized mice, 18, weighing 18-22 g.

In our pilot study, hACE2 transgenic mice were intranasally inoculated with SARS-CoV-2 ($2\times10^5$ plaque forming units (PFU) virus per mouse) and were treated with vehicle (control), ATV006 (500 mg/kg, IG, once daily), or ATV006 (250 mg/kg, IG, once daily) starting at 2 h prior to virus inoculation (FIG. 5A) and continuing until 4 days post-infection.

Figure 5:
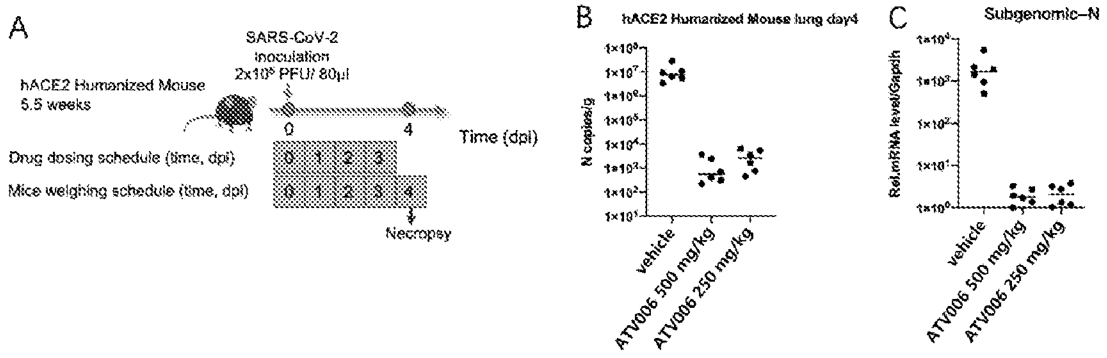
FIG. 5A Schematic of the experiment viral infection in hACE2 humanized mice.
FIG. 5B shows the in vivo anti-SARS-CoV-2 efficacy of compound ATV006 in SARS-CoV-2 in hACE2 humanized and Ad5-hACE2 mouse model by viral titers in the lung (analysis of N gene).
FIG. 5C shows the in vivo anti-SARS-CoV-2 efficacy of compound ATV006 in SARS-CoV-2 in hACE2 humanized and Ad5-hACE2 mouse model by viral titers in the lung (analysis of sub-N gene).

At 4 dpi, we evaluated the abundance of mouse lung tissue genome (N gene) and subgenomic viral RNA (subgenomic N) by qPCR. The amount of viral genome and viral subgenome in the drug-treated group was significantly lower than that in the control group (FIGS. 5B and 5C).

Mice: SPF-grade male C57BL/6 K18-hACE2 mice, 6, weighing 18-22 g.

Mice were inoculated intranasally with $1\times10^4$ PFU virus (B.1.617.2 variants) per mouse and were then treated with vehicle (control), ATV006 (250 mg/kg, IG, once daily) starting at 2 h prior to virus inoculation (FIG. 6A) and continuing until 3 days post-infection.

Figure 6:
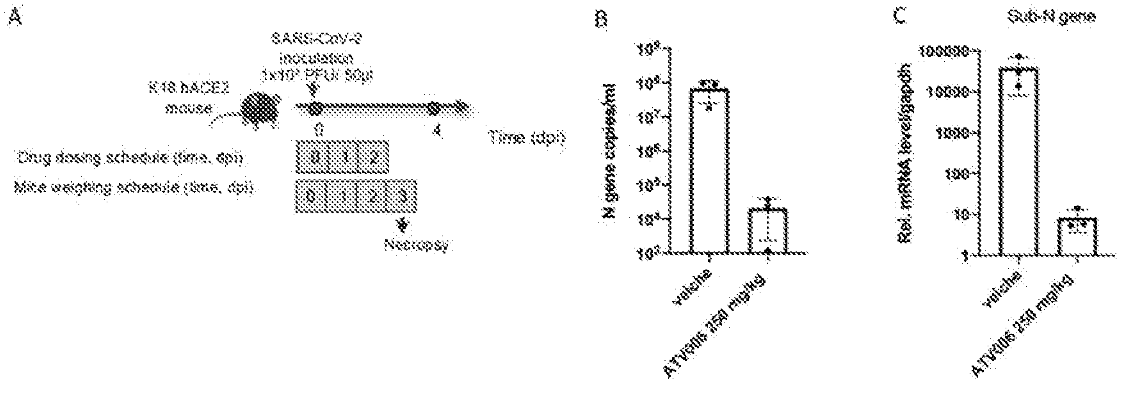
FIG. 6A Schematic of the experiment viral infection in K18 hACE2 mouse model.
FIG. 6B shows the in vivo anti-SARS-CoV-2 efficacy of compound ATV006 in SARS-CoV-2 in K18 hACE2 mouse model by viral titers in the lung (analysis of N gene).
FIG. 6C shows the in vivo anti-SARS-CoV-2 efficacy of compound ATV006 in SARS-CoV-2 in K18 hACE2 mouse model by viral titers in the lung (analysis of sub-N gene).

At 3 dpi, we evaluated the abundance of mouse lung tissue genome (N gene) and subgenomic viral RNA (subgenomic N) by qPCR. The amount of viral genome and viral subgenome in the drug-treated group was significantly lower than that in the control group (FIGS. 6B and 6C).

Conclusion: Our results show that intragastric administration of ATV006 can effectively inhibit the replication of SARS-CoV-2 and B.1.617.2 variant in two mouse models, and they represent the potential of ATV006 an orally available anti-SARS-CoV-2 drug.

All patents, publications, and references cited herein are hereby fully incorporated by reference. In case of conflict between the present disclosure and incorporated patents, publications, and references, the present disclosure should control.

The invention claimed is:

1. A compound of Formula (I):

(I)

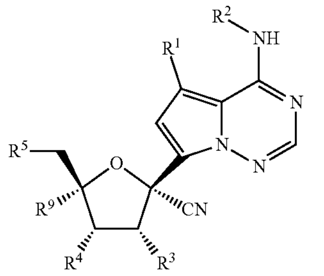

or a pharmaceutically acceptable salt thereof, or a pharmaceutically acceptable form thereof, wherein:

$R^1$ is H, For D;

$R^2$ is H, OH or $R^6$;

each of $R^3$ and $R^4$ is OH;

$R^5$ is H, D, $R^6$, $R^7$, —$OR^6$, —$OR^7$, —$NH_2$, —$NHR^6$, —$NHR^7$, —$NR^7R^8$, SH, —$SR^7$, —$SSR^7$, $SeR^7$, L-amino acid ester, or D-amino acid ester;

$R^6$ is —C(═O)$R^7$, —C(═O)$OR^7$, —C(═O)$NHR^7$, —C(═O)$NR^7R^8$, —$CH_2OC$(═O)$OR^7$, —$CH_2OC$(═O)$NHR^7$, —$CH_2OC$(═O)$NR^7R^8$, —C(═O)$SR^7$, —C(═S)$R^7$, —S(═O)$R^7$ or —S(═O)$_2R^7$;

each of $R^7$ and $R^8$ is independently a substituted or non-substituted $C_1$-$C_{10}$ alkyl, a substituted or non-substituted $C_3$-$C_{10}$ cycloalkyl, a substituted or non-substituted $C_3$-$C_{10}$ cycloalkenyl, a substituted or non-substituted $C_3$-$C_{10}$ cycloalkynyl, a substituted or non-substituted $C_2$-$C_{10}$ enyl, a substituted or non-substituted $C_2$-$C_{10}$ alkynyl, a substituted or non-substituted $C_6$-$C_{20}$ aryl, a substituted or non-substituted $C_3$-$C_{20}$ heterocyclyl, a substituted or non-substituted $C_6$-$C_{20}$ aralkyl, or a deuterium substitute of any of them;

$R^9$ is H or F.

2. The compound according to claim 1, or a pharmaceutically acceptable salt thereof, wherein the substituted or non-substituted $C_1$-$C_{10}$ alkyl is a substituted or non-substituted $C_1$-$C_5$ alkyl, a substituted or non-substituted $C_2$-$C_4$ alkyl, or a substituted or non-substituted $C_2$-$C_3$ alkyl; and/or wherein the substituted or non-substituted $C_3$-$C_{10}$ cycloalkyl is a substituted or non-substituted $C_3$-$C_6$ cycloalkyl, a substituted or non-substituted $C_4$-$C_{10}$ cycloalkyl, a substituted or non-substituted $C_4$-$C_8$ cycloalkyl, a substituted or non-substituted $C_4$-$C_6$ cycloalkyl, or a substituted or non-substituted $C_5$-$C_6$ cycloalkyl; and/or wherein the substituted or non-substituted $C_3$-$C_{10}$ cycloalkenyl is a substituted or non-substituted $C_3$-$C_{10}$ cycloalkenyl, a substituted or non-substituted $C_4$-$C_{10}$ cycloalkenyl, a substituted or non-substituted $C_4$-$C_8$ cycloalkenyl, a substituted or non-substituted $C_4$-$C_6$ cycloalkenyl, or a substituted or non-substituted $C_5$-$C_6$ cycloalkenyl; and/or the substituted or non-substituted $C_6$-$C_{20}$ aryl is selected from the group consisting a substituted or non-substituted $C_6$-$C_{12}$ aryl, or a substituted or non-substituted $C_6$-$C_{10}$ aryl; and/or the substituted or non-substituted $C_3$-$C_{20}$ heterocyclyl is selected from the group consisting a substituted or non-substituted $C_4$-$C_{10}$ heterocyclyl, a substituted or non-substituted $C_4$-$C_6$ heterocyclyl, a substituted or non-substituted $C_4$-$C_5$ heterocyclyl.

3. The compound according to claim 1, or a pharmaceutically acceptable salt thereof, wherein the substituted group is a methyl, ethyl, phenyl, indole, pyrrole, amino, halogen, sulfhydryl or thiol-methyl substitution.

4. The compound according to claim 1, or a pharmaceutically acceptable salt thereof, wherein $R^5$ is —$OR^6$, L-amino acid ester, or D-amino acid ester; or wherein $R^5$ is —$OR^6$; or wherein $R^5$ is —$OR^6$ and $R^6$ is —$C(=O)R^7$.

5. The compound according to claim 1, wherein the compound of Formula (I) is selected from a compound of Formula (II), or a pharmaceutically acceptable salt thereof, or a pharmaceutically acceptable form thereof:

(II)

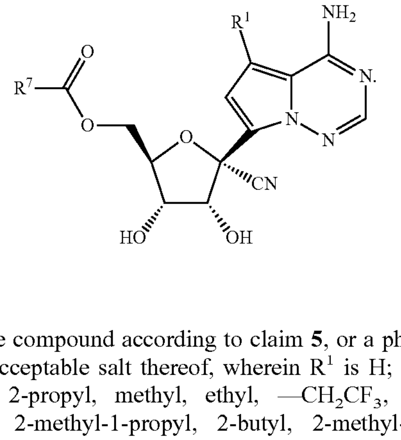

6. The compound according to claim 5, or a pharmaceutically acceptable salt thereof, wherein $R^1$ is H; and $R^7$ is phenyl, 2-propyl, methyl, ethyl, —$CH_2CF_3$, 1-propyl, 1-butyl, 2-methyl-1-propyl, 2-butyl, 2-methyl-2-propyl, 1-amyl, 3-amyl, 2-methyl-2-butyl, 3-methyl-2-butyl, 3-methyl-1-butyl, 2-methyl-1-butyl, 1-hexyl, 2-hexyl, 3-hexyl, 2-methyl-2-amyl, 3-methyl-2-amyl, 4-methyl-2-amyl, 3-methyl-3-amyl, 2-methyl-3-amyl, 2, 3-dimethyl-2-butyl, 3, 3-dimethyl-2-butyl, 3, 3-dimethyl-2-butyl, octyl, naphthalene, tetrahydro-2H-pyranyl and 1-methylpiperidyl; or $R^7$ is selected from cyclopropyl, cyclobutyl, cyclopentyl, cyclohexyl, cycloheptyl or cyclooctyl.

7. The method according to claim 1, wherein the compound of Formula (I) is:

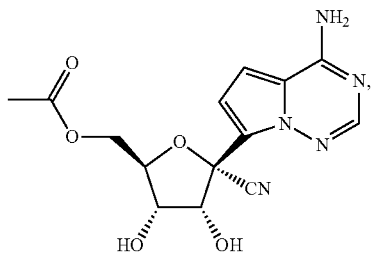

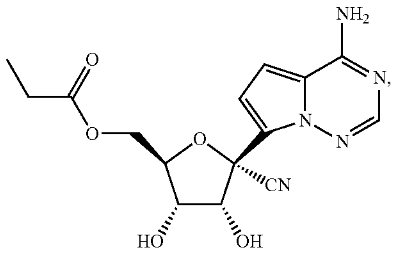

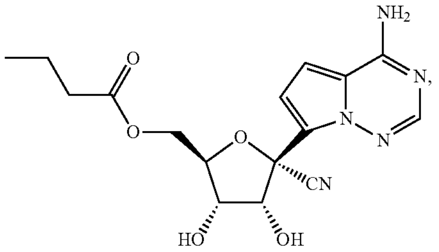

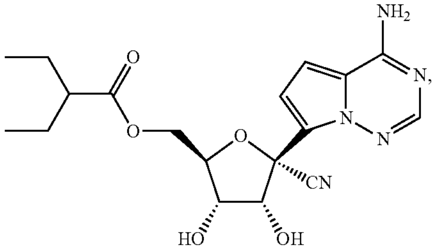

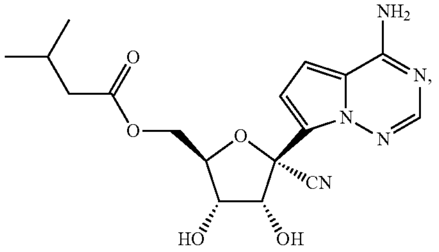

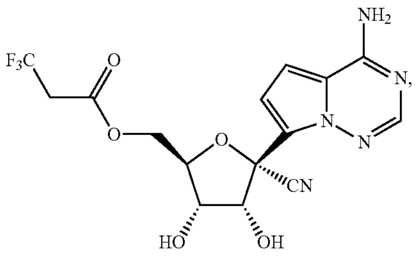

-continued
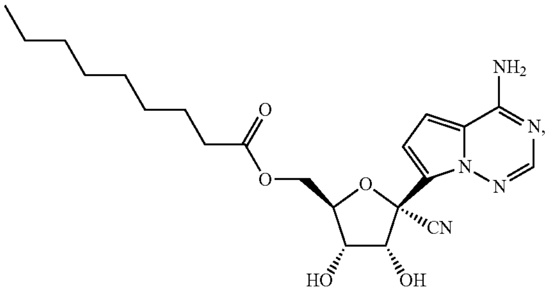
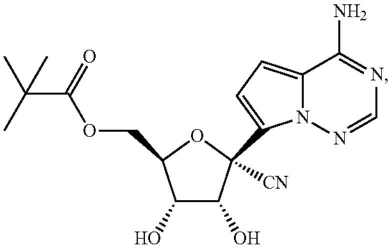
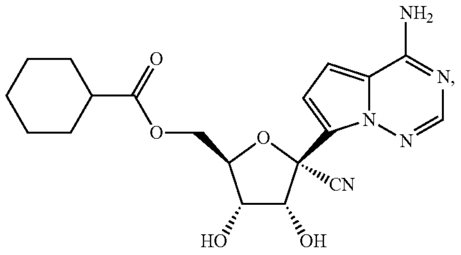
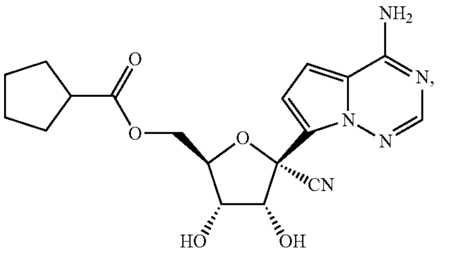
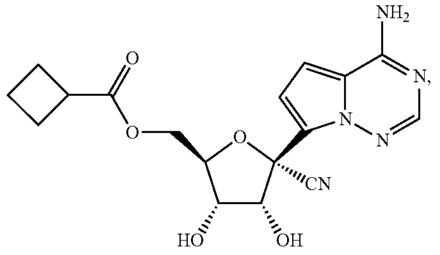
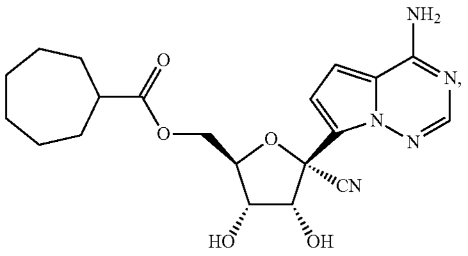
-continued
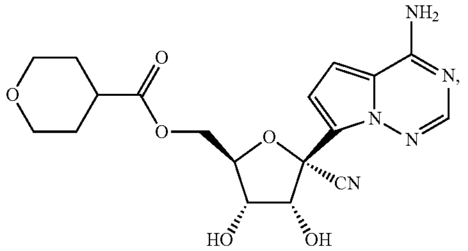
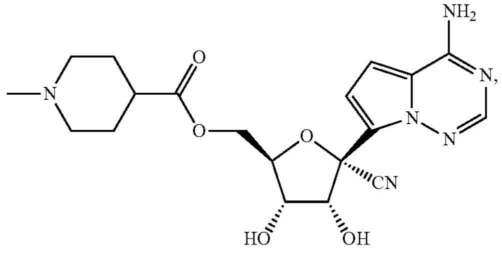
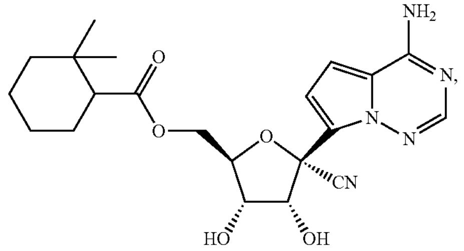
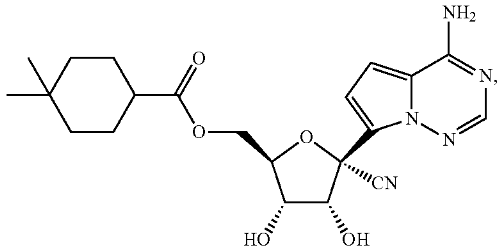
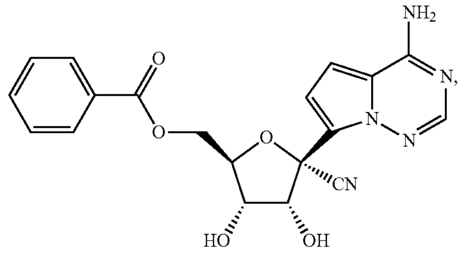
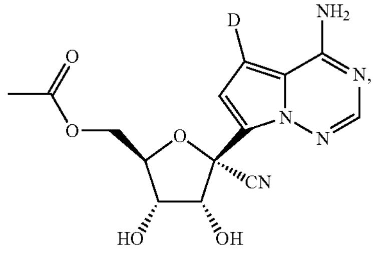

-continued
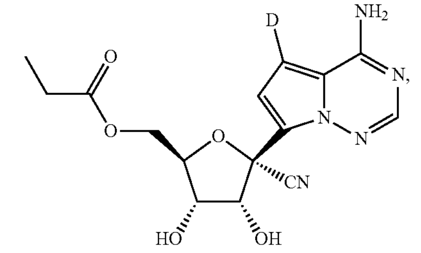
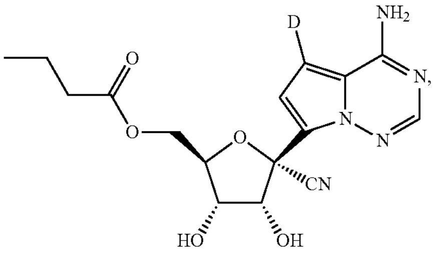
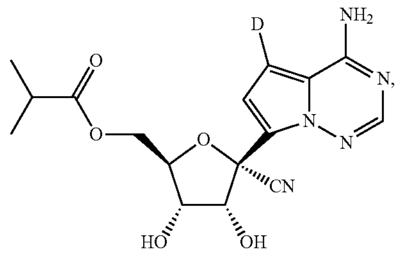
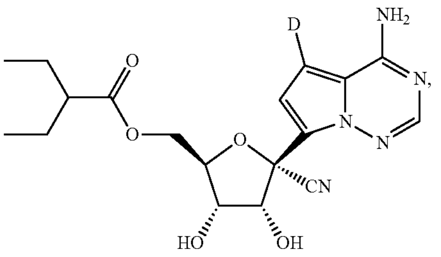
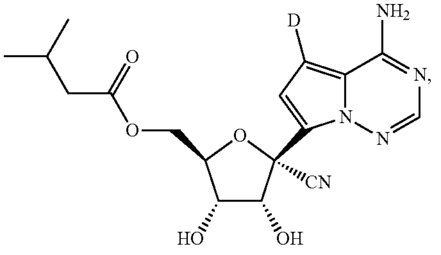
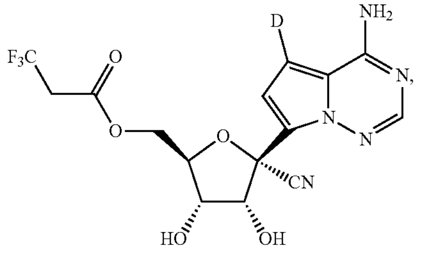
-continued
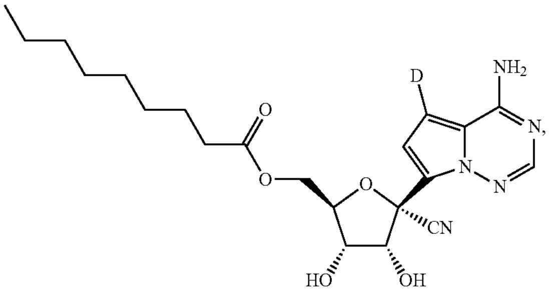
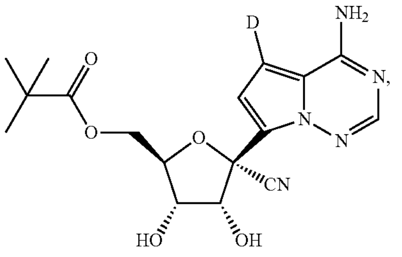
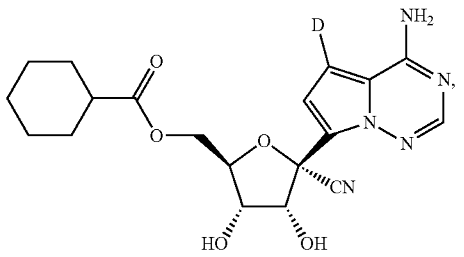
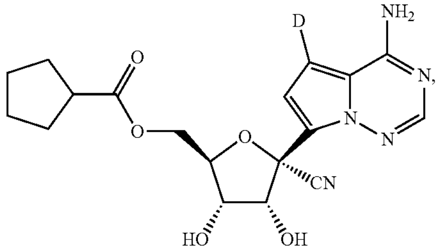
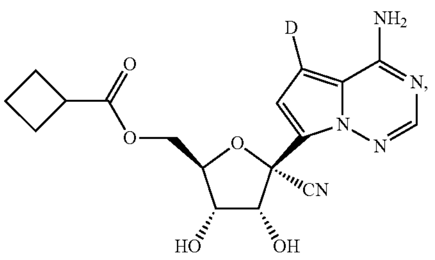
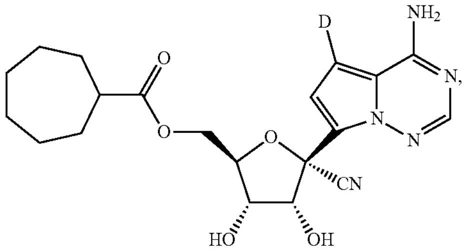

-continued
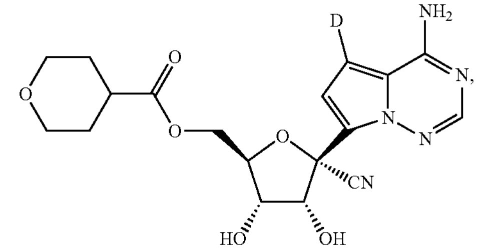
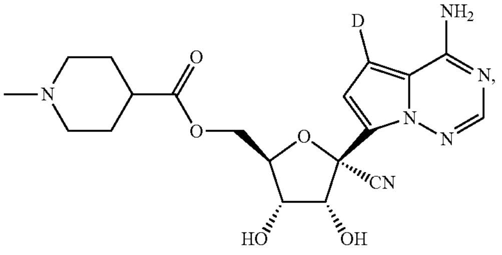
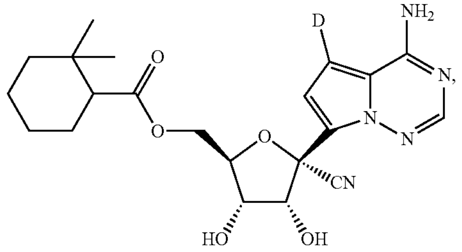
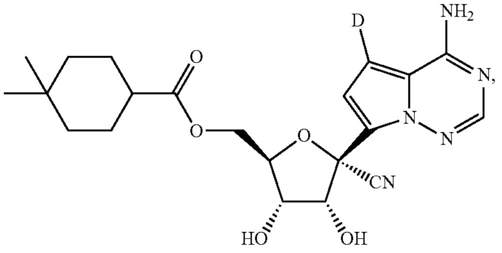
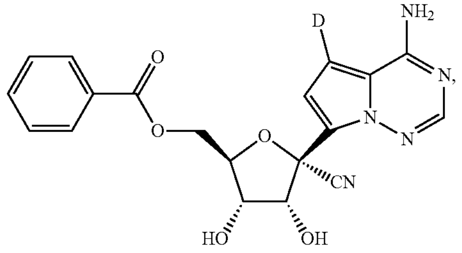
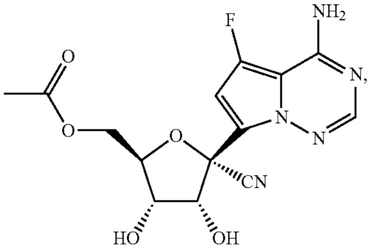
-continued
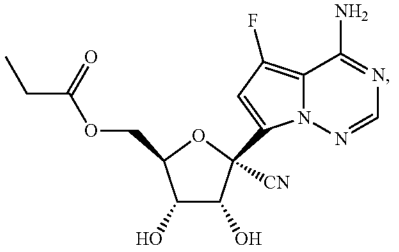
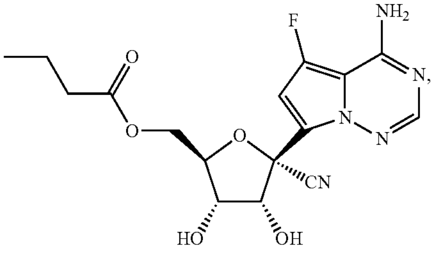
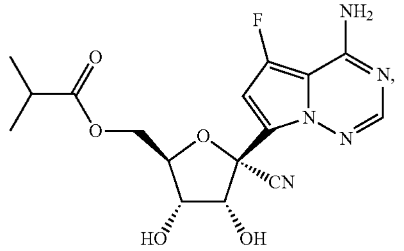
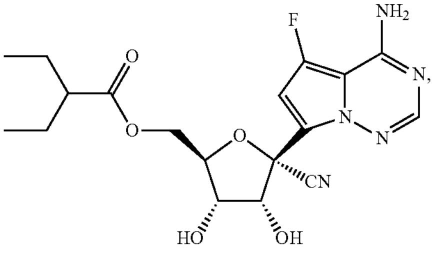
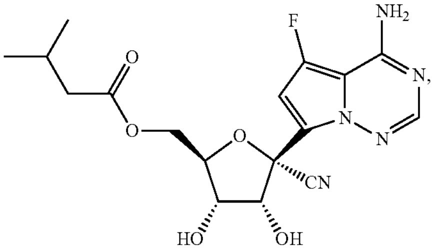
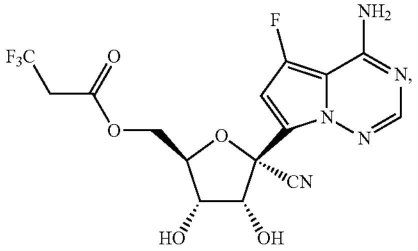

-continued
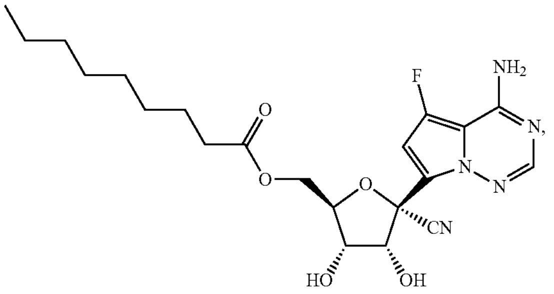
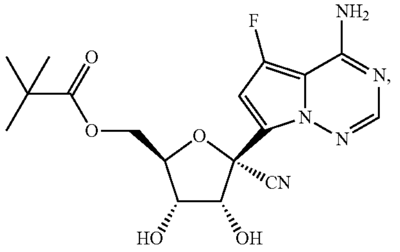
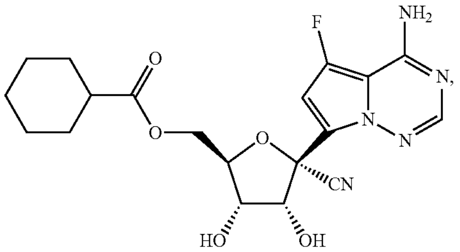
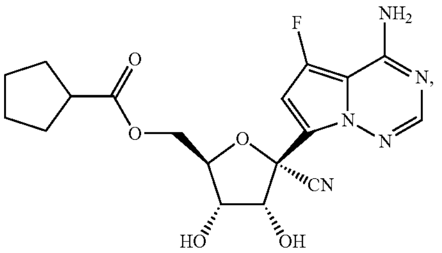
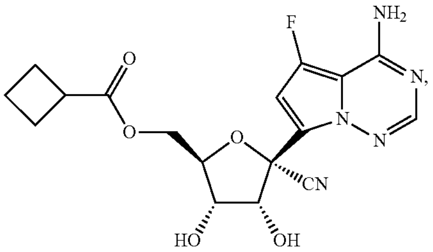
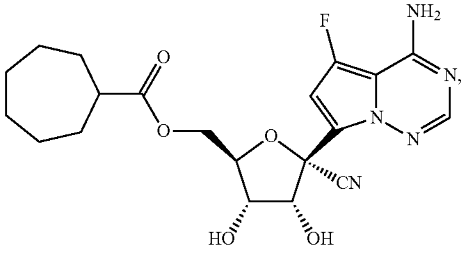
-continued
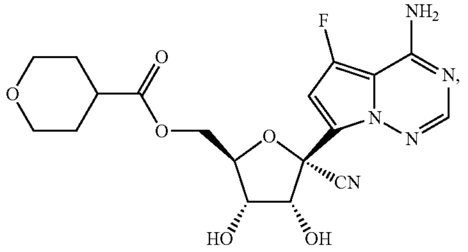
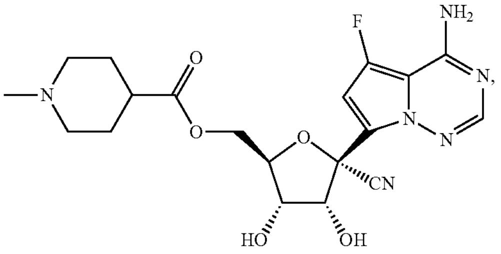
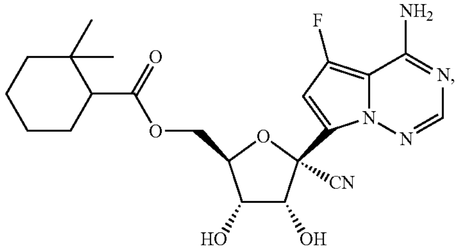
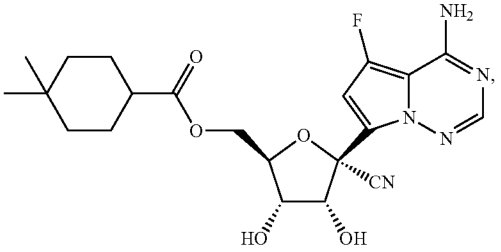
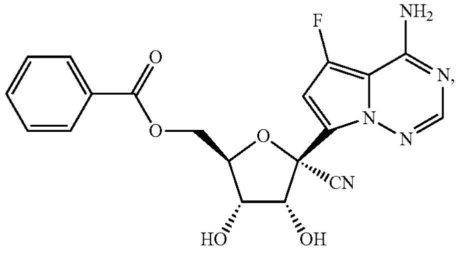
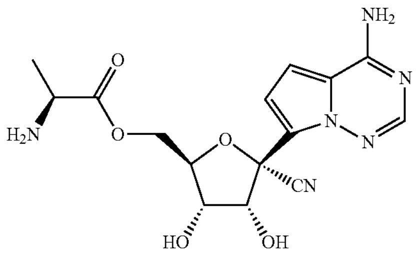

-continued
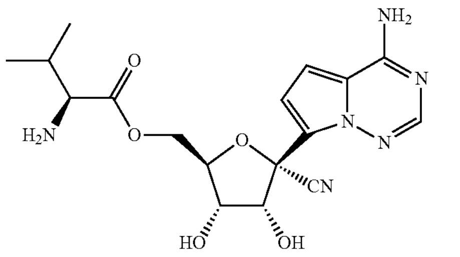
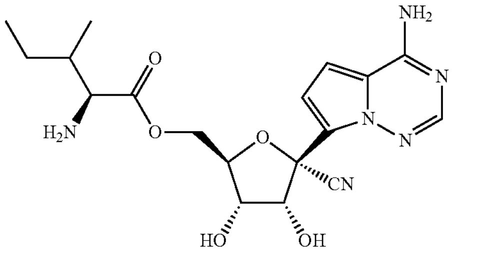
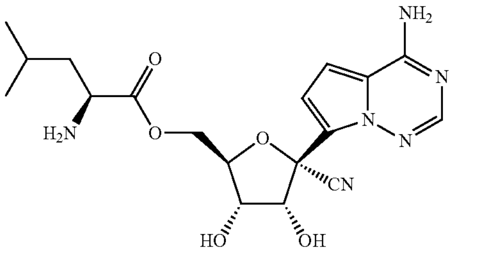
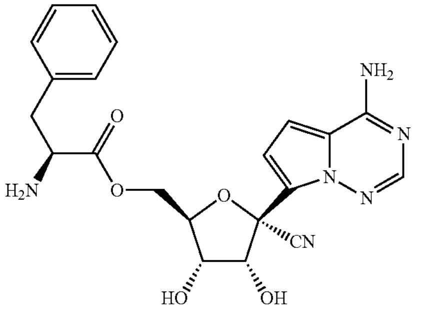
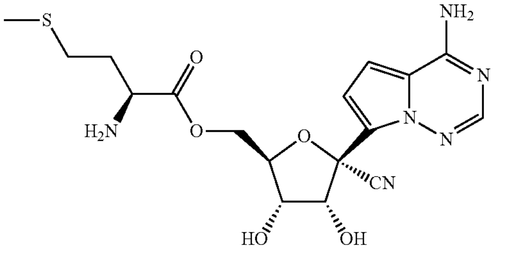
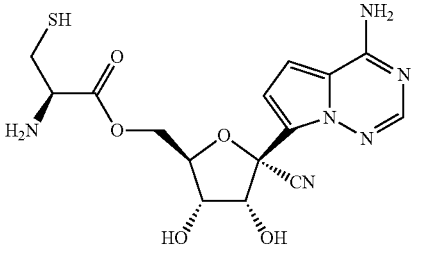
-continued
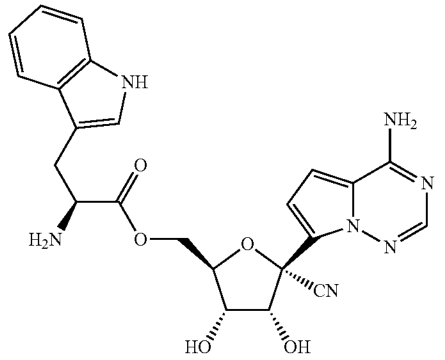
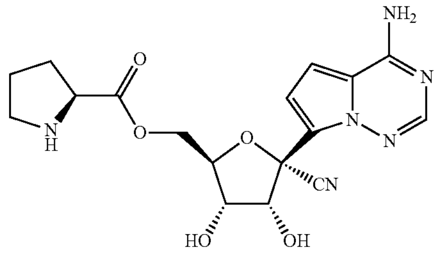
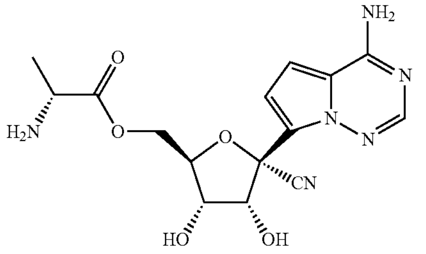
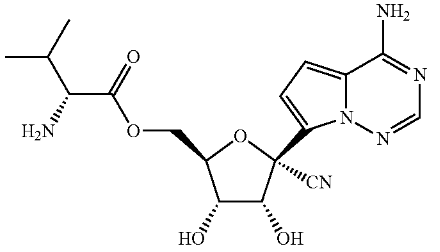
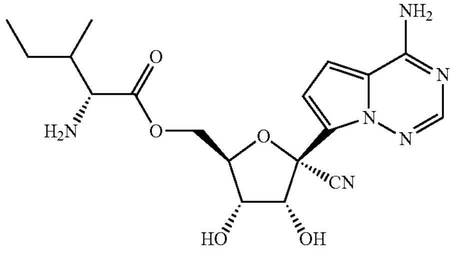
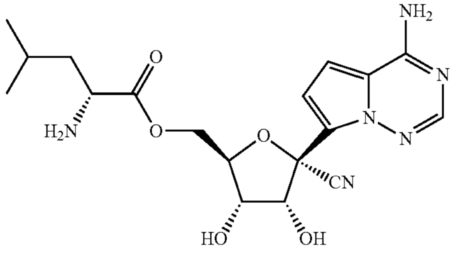

-continued

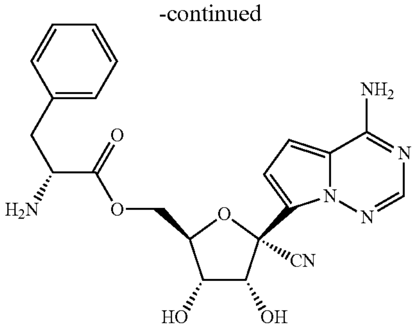

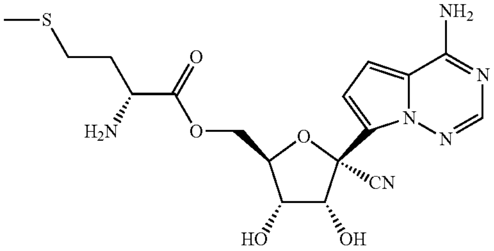

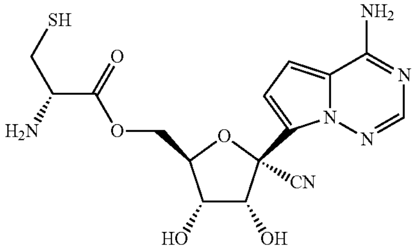

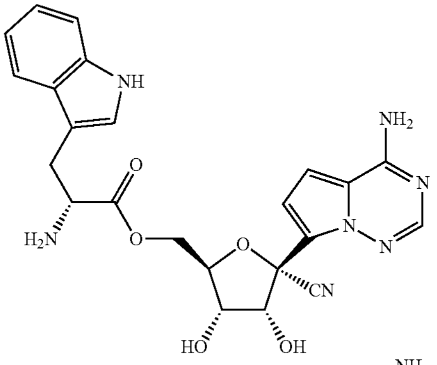

or

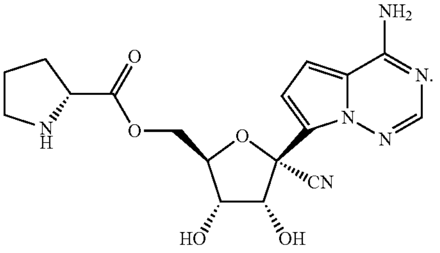

8. The compound of claim 1, wherein the pharmaceutically acceptable form of the compound comprises a racemate, an enantiomer, a tautomer, a polymorph, a pseudo polymorph, an amorphous form, a hydrate, or a solvate.

9. A pharmaceutical composition comprising the compound of claim 1 or a pharmaceutically acceptable salt thereof, and a pharmaceutically acceptable carrier or excipient.

10. A method of preventing, mitigating, or treating a coronavirus infection or a cytopathic effect resulting from the replication or reproduction of a coronavirus variant comprising administering an effective amount of the compound of claim 1, or a pharmaceutically acceptable salt thereof to a subject in need thereof, wherein the coronavirus infection comprises fever, cough, sore throat, pneumonia, acute respiratory infection, severe acute respiratory infection, hypoxic respiratory failure, acute respiratory distress syndrome, sepsis, or septic shock, wherein the coronavirus is SARS-COV-2 or a variant thereof, and wherein the SARS-COV-2 variant comprises an Alpha variant having a lineage of B.1.1.7, a Beta variant having a lineage of B.1.351, B.1.351.2, or B.1.351.3, a Delta variant having a lineage of B.1.617.2, AY.1, AY.2, or AY.3, a Gamma variant having a lineage of P.1, P.1.1, or P.1.2, an Eta variant having a lineage of B.1.525, a Theta variant having a lineage of P.3, a Kappa variant having a lineage of B.1.617.1, a Lambda variant having a lineage of C.37 or a sub-lineage thereof.

11. A method for detecting a coronavirus or a homologous variant thereof comprising administering an effective amount of the compound of claim 1, or a pharmaceutically acceptable salt thereof to a subject in need thereof, wherein the coronavirus is SARS-COV-2 or a variant thereof, and wherein the SARS-COV-2 variant comprises an Alpha variant having a lineage of B.1.1.7, a Beta variant having a lineage of B.1.351, B.1.351.2, or B.1.351.3, a Delta variant having a lineage of B.1.617.2, AY.1, AY.2, or AY.3, a Gamma variant having a lineage of P.1, P.1.1, or P.1.2, an Eta variant having a lineage of B.1.525, a Theta variant having a lineage of P.3, a Kappa variant having a lineage of B.1.617.1, a Lambda variant having a lineage of C.37 or a sub-lineage thereof.

12. The method of claim 10, wherein the compound or its pharmaceutically acceptable salt thereof is provided to human or non-human animals, wherein the non-human animal subject is bovine, equine, sheep, pig, canine, cat, rodent, primate, bird, or fish.

13. A method of preventing, mitigating, or treating a coronavirus infection or a cytopathic effect resulting from the replication or reproduction of a coronavirus variant comprising administering an effective amount of the pharmaceutical composition of claim 9 to a subject in need thereof, wherein the coronavirus infection comprises fever, cough, sore throat, pneumonia, acute respiratory infection, severe acute respiratory infection, hypoxic respiratory failure, acute respiratory distress syndrome, sepsis, or septic shock, wherein the coronavirus is SARS-COV-2 or a variant thereof, and wherein the SARS-COV-2 variant comprises an Alpha variant having a lineage of B.1.1.7, a Beta variant having a lineage of B.1.351, B.1.351.2, or B.1.351.3, a Delta variant having a lineage of B.1.617.2, AY.1, AY.2, or AY.3, a Gamma variant having a lineage of P.1, P.1.1, or P.1.2, an Eta variant having a lineage of B.1.525, a Theta variant having a lineage of P.3, a Kappa variant having a lineage of B.1.617.1, a Lambda variant having a lineage of C.37 or a sub-lineage thereof.

14. A method for detecting a coronavirus or a homologous variant thereof comprising administering an effective amount of the pharmaceutical composition of claim 9 to a subject in need thereof, wherein the coronavirus is SARS-COV-2 or a variant thereof, and wherein the SARS-COV-2 variant comprises an Alpha variant having a lineage of B.1.1.7, a Beta variant having a lineage of B.1.351, B.1.351.2, or B.1.351.3, a Delta variant having a lineage of B.1.617.2, AY.1, AY.2, or AY.3, a Gamma variant having a lineage of P.1, P.1.1, or P.1.2, an Eta variant having a lineage of B.1.525, a Theta variant having a lineage of P.3, a Kappa variant having a lineage of B.1.617.1, a Lambda variant having a lineage of C.37 or a sub-lineage thereof.

15. The method of claim 13, wherein the pharmaceutical composition is provided to human or non-human animals, wherein the non-human animal subject is bovine, equine, sheep, pig, canine, cat, rodent, primate, bird, or fish.

* * * * *